United States Patent [19]
Kataoka et al.

[11] Patent Number: 5,990,346
[45] Date of Patent: Nov. 23, 1999

[54] PROSTAGLANDINS AND PROCESSES FOR PRODUCTION THEREOF

[75] Inventors: Kenichiro Kataoka, Tokyo; Toru Minoshima, Yamaguchi; Tatsuki Shiota, Tokyo; Takaharu Tsutsumi, Tokyo; Takahiko Hada, Tokyo; Hiroko Tanaka, Tokyo; Takuya Morita, Tokyo; Noriaki Endo, Tokyo, all of Japan

[73] Assignee: Teijin Limited, Osaka, Japan

[21] Appl. No.: 08/793,486

[22] PCT Filed: Jun. 17, 1996

[86] PCT No.: PCT/JP96/01662

§ 371 Date: Feb. 26, 1997

§ 102(e) Date: Feb. 26, 1997

[87] PCT Pub. No.: WO97/01534

PCT Pub. Date: Jan. 16, 1997

[30] Foreign Application Priority Data

Jun. 26, 1995 [JP] Japan .................................. 7-159189
Dec. 15, 1995 [JP] Japan .................................. 7-327085

[51] Int. Cl.⁶ .................. C07C 405/00; C07C 69/74; A61K 31/557
[52] U.S. Cl. .................. 562/503; 549/422; 554/117; 554/214; 560/121; 514/573
[58] Field of Search .................. 562/503; 435/63; 549/422; 554/117, 214; 560/121; 514/573

[56] References Cited

U.S. PATENT DOCUMENTS 4,363,817 12/1982 Biddlecom .............................. 424/311

OTHER PUBLICATIONS

CA 125:114386, May 1996.
CA 123:339525, Jul. 1995.
CA122:274094, Apr. 1992.
XA 115:214847, Apr. 1991.

*Primary Examiner*—Paula K. Hutzell
*Assistant Examiner*—Timothy A. Worrall
*Attorney, Agent, or Firm*—Sughrue, Mion, Zinn, Macpeak & Seas, PLLC

[57] ABSTRACT

A prostaglandin having formula (I), (II), or (III):

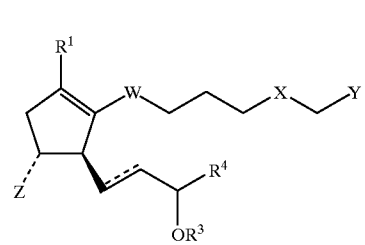

(I)

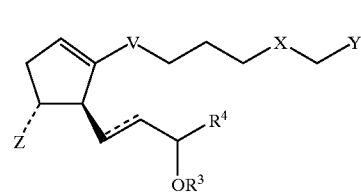

(II)

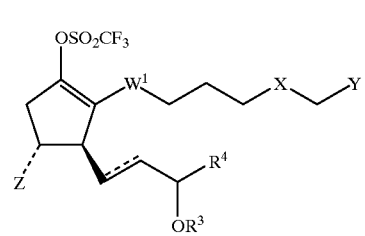

(III)

a process of production thereof, and inhibitors of cell migration caused by chemokines containing (I) or (II) as an active ingredient.

13 Claims, No Drawings

PROSTAGLANDINS AND PROCESSES FOR PRODUCTION THEREOF

TECHNICAL FIELD

The present invention relates to novel prostaglandins having a cell migration inhibitory activity and useful as pharmaceuticals, processes for production of the same, intermediates useful in their synthesis, and medicines containing the same.

BACKGROUND ART

Prostaglandin derivatives have various biological activities such as inhibition of platelet aggregation, a vasodilating activity lowering the blood pressure, suppression of the secretion of gastric acids, smooth muscle constriction, cytoprotection, and digresis and are useful for the treatment or prevention of cardiac infarction, angia, arteriosclerosis, hypertension, duodenal ulcers, oxytocia, abortion, etc.

Among these prostaglandin derivatives, as $\Delta^8$ type prostaglandin derivatives, there have been known the prostaglandin $E_1$ affines of enol butyric acid esters of prostaglandin $E_1$ (see Japanese Unexamined Patent Publication (Kokai) No. 5-213862).

On the other hand, it has been disclosed that 7-thiaprostaglandin $E_1$ derivatives have a platelet aggregation inhibitory activity, hypotensive activity, and vasodilating activity and thereby an anti-thrombosis, anti-anginia, anti-cardiac infarction, anti-arteriosclerosis, and malignant tumor metathesis preventing activity and have an anti-tumor activity (see Japanese Unexamined Patent Publication (Kokai) No. 53-68753, Japanese Unexamined Patent Publication (Kokai) No. 58-110562, Japanese Unexamined Patent Publication (Kokai) No. 59-29661, Japanese Unexamined Patent Publication (Kokai) No. 60-185761, and Japanese Unexamined Patent Publication (Kokai) No. 61-204163). Further, these 7-thiaprostaglandin $E_1$ derivatives are known to have effectiveness in the neuropathy in diabetes (see Japanese Unexamined Patent Publication (Kokai) No. 64-52721). Further, it has been reported that 7-thiaprostaglandin $E_1$ derivatives have an activity suppressing thickening of the veins and an activity inhibiting migration of smooth muscle cells (see WO95/00150) and an activity inhibiting migration of THP-1 cells (see Japanese Unexamined Patent Publication (Kokai) No. 7-188025).

Corresponding enol ester derivatives ($\Delta^8$ type prostaglandin derivatives) are known for the 7-thiaprostaglandin $E_1$ derivatives as well. These have been reported as having an activity suppressing thickening of veins and an activity inhibiting migration of THP-1 cells (see WO/19340).

The enol ester derivatives of these (7-thia)prostaglandin $E_1$ derivatives have enol ester portions which easily hydrolyzed in the body due to the action of esterase and other enzymes and are believed to change to (7-this)prostaglandin $E_1$ derivatives (9-oxo type). Therefore, these enol ester derivatives may be considered prodrugs of (7-thia) prostaglandin $E_1$ derivatives.

The $\Delta^8$ type prostaglandins of the present invention differ from these enol ester derivatives in that they are compounds in which substituents not easily decomposed by the action of enzymes etc. are introduced at the 9-position. The inventors studied various compounds which were chemically stable in this way and further exhibited bioactivity in the $\Delta^8$ state and, as a result, found that these compounds have an inhibitory activity on cell migration caused by chemokines and thereby reached the present invention.

On the other hand, it has been reported that $\Delta^8$ type prostaglandin derivatives have a luteal recessive activity and an abortive activity (see DE3125271 or Japanese Unexamined Patent Publication (Kokai) No. 58-4763). The $\Delta^8$-type prostaglandin derivatives shown here, however, are just derivatives where the 9-position substituent is hydrogen and the 7-position is methylene. It was not known at all that the compounds of the present invention have an inhibitory activity on the cell migration caused by chemokines.

DISCLOSURE OF INVENTION

The problems to be solved by the present invention are to provide novel prostaglandins inhibiting cell migration caused by chemokines, for example, monocyte chemotactic protein MCP-1MCAF and useful as medicines for the treatment of arteriosclerosis, diabetic angiopathy, etc.

Here, "CHEMOKINES" (also known as "INTERCRINES") is the general name for the polypeptide inflammatory/immunocontrol factors produced from the active macrophages of the lymph tissue or inflamed portions, white blood cells, etc., having a molecular weight of approximately 10 Kd, having four cysteines, basic, and exhibiting heparin bonding. Their main activity is activity causing cell migration. Interleukin-8, MIP-1$\alpha$/$\beta$ (abbreviation for Macrophage Inflammatory Protein-1$\alpha$/$\beta$), MCP-1 (abbreviation for Monocyte Chemotactic Protein-1), etc. fall under this category. Involvement in various chronic/acute inflammatory diseases is suggested in this cytokine family (see for example, MICHIEL, D. (1993), BIOTECHNOLOGY, vol. 11, p. 739, OPPENHEIM, J. J. et al., (1991), Annual Review of IMMUNOLOGY, vol. 9, pp. 617–648, NEOTE, K. et al., (1993), CELL, pp. 415–425, SCHALL, T. J. (1991), CYTOKINE, vol. 3, pp. 165–183, etc.) Among these, monocyte chemotatic protein MCP-1 (also known as MCAF (abbreviation for MACROPHAGE CHEMOTACTIC AND ACTIVATING FACTOR) are produced from T-lympocytes, macrophages, smooth muscle cells, fibroblasts, vascular endothelial cells, etc. along with various stimuli and have migration activity with respect to monocytes, activated T-cells, and natural killer cells. In diseases in which monocyte/macrophage cells and/or activated T-cells and natural killer cells are closely involved in the advance of the diseases, for example, resterosis or reocclusion occurring after trauma to the intima of arteries in angioplasty etc., stenosis or occlusion due mainly to formation of atherosclerosis at the coronary artery or carotid artery, arteriosclerosis occurring in heart transplants, rejection of organ transplants, rheumatoid arthritis, glomerular nephritis, and diabetic microangiopathy, the chemokine induces the accumulation of the monocyte/macrophage and/or activated T cells and natural killer cells in the blood into the lesions, and activates the accumulated monocyte/macrophages etc.. Therefore, it is strongly suggested that MCP-1 is deeply involved in the occurrence and progression of these lesions (see for example, LEONARD, E. J. and YOSHIMURA, T. (1990), IMMUNOLOGY TODAY, vol. 11, pp. 97–101, NELKEN, N. A. et al., THE JOURNAL OF CLINICAL INVESTIGATION (1991), vol. 88, pp. 1121–1127, KOCH, A. E. et al., E. JOURNAL OF CLINICAL INVESTIGATION (1992), vol. 90, pp. 772–779, HANAZAWA, S. et al., (1993) THE JOURNAL OF BIOLOGICAL CHEMISTRY, vol. 268, pp. 9626–9532, GRAVES, D. T. et al., AMERICAN JOURNAL OF PATHOLOGY (1992), vol. 140, pp. 9–14, EDGINGTON, S. M., BIO/TECHNOLOGY (1993), vol. 11, pp. 676–681, ADAMS, D. H. et al., IMMUNOLOGICAL REVIEWS (1993), vol. 134, pp. 5–19, CARR, M. W. et al., (1994)

PROC. NATL. ACAD. SCI., USA, vol. 91, pp. 3652–3656, ALLAVENA, P. et al., (1994), EUROPEAN JOURNAL OF IMMUNOLOGY, vol. 24, pp. 3233–3236, etc.). Drugs which inhibit the migration of cells caused by MCP-1MCAF are expected to be useful as drugs for the treatment and/or prevention of restenosis or reocclusion occurring after trauma to the intima of arteries in angioplasty etc., stenosis or occlusion caused primarily by formation of atherosclerosis in the coronary artery or carotid artery etc., arteriosclerosis occurring in heart transplants, diabetic angiopathy, glomerular nephritis, rheumatoid arthritis, osteoarthritis, or rejection of organ transplants, etc.

The present inventors engaged in intensive studies on the possibility of novel prostaglandins inhibiting cell migration caused by chemokines and, as a result, found that the prostaglandins of the present invention are powerful inhibitors of cell migration caused by chemokines, for example, monocyte chemotactic protein MCP-1/MCAF, and thus completed the present invention.

That is, in accordance with the present invention, there is provided a prostaglandin which is a compound having the following formula (I):

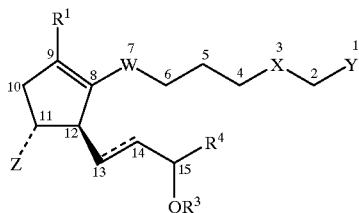
(I)

an enantiomer thereof, or any mixtures of the enantiomers thereof at any ratio.

In formula (I) italicized small numbers are based on numbering of a prostanoic acid, $R^1$ indicates a $C_1$ to $C_{10}$ straight chain or branched alkyl group, $C_1$ to $C_8$ cycloalkyl group, cyano group, formyl group, carboxyl group, ($C_1$ to $C_5$ alkyl)oxycarbonyl group, $C_2$ to $C_7$ alkanoyl group, or a $C_1$ to $C_5$ alkyl group substituted with (a) halogen atom(s) or substituted or unsubstituted phenyl group(s), Z indicates a hydrogen atom or $OR^2$, $R^2$ and $R^3$ are the same or different and indicate a hydrogen atom, tri($C_1$ to $C_7$ hydrocarbon)silyl group, or group forming an acetal bond with the oxygen atom of a hydroxy group, $R_4$ indicates a $C_1$ to $C_8$ straight chain or branched alkyl group, $C_2$ to $C_8$ straight chain or branched alkenyl group, $C_2$ to $C_8$ straight chain or branched alkynyl group, substituted or unsubstituted phenyl group, substituted or unsubstituted $C_3$ to $C_8$ cycloalkyl group, further, a straight chain or branched ($C_1$ to $C_5$ alkyl group, $C_2$ to $C_5$ alkenyl group, or $C_2$ to $C_5$ alkynyl group) substituted with a ($C_1$ to $C_5$ alkoxy group, substituted or unsubstituted phenyl group, substituted or unsubstituted phenoxy group, substituted or unsubstituted $C_3$ or $C_8$ cycloalkyl group, or substituted or unsubstituted heterocyclic group), Y indicates a $C_1$ to $C_5$ straight chain or branched alkyl group or $CO_2R^5$, $R^5$ indicates a hydrogen atom, $C_1$ to $C_{10}$ straight chain or branched alkyl group, $C_2$ to $C_{10}$ straight chain or branched alkenyl group, or one equivalent cation, X indicates a methylene group or oxygen atom, W indicates a sulfur atom or a sulfynyl group or methylene group, and the mark $=$ indicates a double bond or single bond.

In accordance with the present invention, there is further provided a prostaglandin which is a compound having the formula (II):

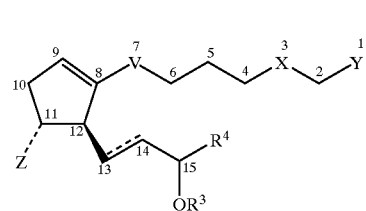
(II)

an enantiomer thereof or any mixtures of the enantiomers thereof at any ratio.

In the formula (II), italicized small numbers are based on numbering of prostanoic acids, V indicates a sulfur atom or sulfinyl group and $R^3$, $R^4$, X, Y, Z, and the mark $=$ have the same definitions as explained in the above formula (I).

In accordance with the present invention, there is further provided a prostaglandin which is a compound having the formula (III):

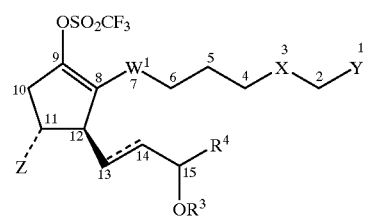
(III)

an enantiomer thereof, or any mixtures of enantiomers thereof at any ratio.

In the formula (III), italicized small numbers are based on numbering of prostanoic acids, $W^1$ indicates a sulfur atom or methylene group, and $R^3$, $R^4$, X, Y, Z, and the mark $=$ have the same definitions as explained in the above formula (I).

BEST MODE FOR CARRYING OUT THE INVENTION

In the prostaglandins of the above formula (I), $R^1$ indicates a $C_1$ to $C_{10}$ straight chain or branched alkyl group, $C_3$ to $C_8$ cycloalkyl group, formyl group, carboxyl group, ($C_1$ to $C_5$ alkyl)oxycarbonyl group, $C_2$ to $C_7$ alkanoyl group (number of carbon atoms includes carbonyl carbon, same below) or a $C_1$ to $C_5$ alkyl group substituted with (a) halogen atom(s) or substituted or unsubstituted phenyl group(s).

As preferable examples of the $C_1$ to $C_{10}$ straight chain or branched alkyl group, a methyl group, ethyl group, propyl group, isopropyl group, butyl group, isobutyl group, sec-butyl group, tert-butyl group, pentyl group, isopentyl group, neopentyl group, hexyl group, 3,3-dimethylbutyl group, heptyl group, octyl group, nonyl group, decyl group, etc. may be mentioned.

As preferable examples of the $C_3$ to $C_8$ cycloalkyl group, a cyclopropyl group, cyclopentyl group, cyclohexyl group, cyclohexenyl group, cycloheptyl group, cyclooctyl group, etc. may be mentioned.

As preferable examples of the ($C_1$ to $C_5$ alkyl) oxycarbonyl group, a methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, etc. may be mentioned.

As preferable examples of the $C_2$ to $C_7$ alkanoyl group, an acetyl group, propionyl group, butyryl group, isobutyryl group, valeryl group, isovaleryl group, pivaroyl group, etc. may be mentioned.

As preferable examples of the alkyl group of the substituted $C_1$ to $C_5$ alkyl group with the halogen atom(s) or substituted or unsubstituted phenyl group(s), the $C_1$ to $C_5$ alkyl groups among the preferable examples of the above-mentioned $C_1$ to $C_{10}$ straight chain or branched alkyl group may be mentioned as preferable examples.

As the halogen atom serving as a substituent bonding with the $C_1$ to $C_5$ alkyl group, a fluorine atom or chlorine atom may be mentioned. One or more of these halogen atoms may be substituted at any position of the $C_1$ to $C_5$ alkyl group. One or more of the substituted or unsubstituted phenyl groups serving as the substituent bonding with the $C_1$ to $C_5$ alkyl group may be substituted at any position of the $C_1$ to $C_5$ alkyl group. As the substituent of the phenyl group, (a) $C_1$ to $C_5$ alkyl group(s) or halogen atom(s) may be mentioned as preferable examples. As the $C_1$ to $C_5$ alkyl group serving as the substituent bonding with the phenyl group, the above preferable examples of the $C_1$ to $C_{10}$ alkyl group where there are 1 to 5 carbon atoms may be mentioned. One or more of these alkyl groups may be bonded at any position of the phenyl group. As the halogen atom serving as the substituent bonding with the phenyl group, a fluorine atom or chlorine atom may be mentioned as preferable examples. One or more of these halogen atoms may be substituted at any position of the phenyl group. In the case of plural substituents, any combination of the illustrated substituents may be used. Among these, a methyl group is particularly preferred as $R^1$.

In the prostaglandins of the above formula (I), Z indicates a hydrogen atom or $OR^2$.

In the prostaglandins having the above formula (I), $R^2$ and $R^3$ may be the same or different and indicate a hydrogen atom, tri($C_1$ to $C_7$ hydrocarbon)silyl group, or group forming an acetal bond with the oxygen atom of a hydroxy group. As preferable examples of the tri($C_1$ to $C_7$ hydrocarbon)silyl group, a trimethylsilyl group, tert-butyldimethylsilyl group, or other tri($C_1$ to $C_4$ alkyl)silyl group, tert-butyldiphenylsilyl group or other diphenyl($C_1$ to $C_4$)alkylsilyl group, tribenzylsilyl group, etc. may be mentioned. Further, as preferable examples of the group forming an acetal bond with the oxygen atom of a hydroxy group, a methoxymethyl group, 1-ethoxyethyl group, 2-methoxy-2-propyl group, 2-ethoxy-2-propyl group, (2-methoxyethoxy)methyl group, benzyloxymethyl group, 2-tetrahydropyranyl group, 2-tetrahydrofuranyl group, 6,6-dimethyl-3-oxa-2-oxobicyclo[3.1.0]hexan-4-yl group, etc. may be mentioned. Among these, as $R^2$ and $R^3$, a hydrogen atom or tert-butyldimethylsilyl group is particularly preferred and as Z a hydrogen atom or hydroxy group is preferred.

In the prostaglandins having the above formula (I), $R^4$ indicates a $C_1$ to $C_8$ straight chain or branched alkyl group, $C_2$ to $C_8$ straight chain or branched alkenyl group, $C_2$ to $C_8$ straight chain or branched alkynyl group, substituted or unsubstituted phenyl group, substituted or unsubstituted $C_3$ to $C_8$ cycloalkyl group, or a ($C_1$ to $C_5$ alkoxy group, substituted or unsubstituted phenyl group, substituted or unsubstituted phenoxy group, substituted or unsubstituted $C_3$ to $C_{10}$ cycloalkyl group, or substituted or unsubstituted heterocyclic group) substituted straight chain or branched ($C_1$ to $C_5$ alkyl group, $C_2$ to $C_5$ alkenyl group, or $C_2$ to $C_5$ alkynyl group).

As preferable examples of the $C_1$ to $C_8$ straight chain or branched alkyl group, a methyl group, ethyl group, propyl group, butyl group, pentyl group, hexyl group, heptyl group, octyl group, 1-methyl-1-butyl group, 2-methylhexyl group, 2-hexyl group, and 1,1-dimethylpentyl group may be mentioned.

As preferable examples of the $C_2$ to $C_8$ straight chain or branched alkenyl group, an allyl group, 3-butenyl group, 2-butenyl group, 4-pentenyl group, and 2-pentenyl group may be mentioned.

As preferable examples of the $C_2$ to $C_8$ straight chain or branched alkynyl group, an ethynyl group, 2-propynyl group, 1-propynyl group, 2-butynyl group, 3-butynyl group, 3-hexynyl group, and 1-methyl-3-hexynyl group may be mentioned.

Further, as preferable examples of the substituent in the case where $R^4$ is a substituted phenyl group, a hydroxyl group, $C_2$ to $C_7$ alkanoyloxy group, $C_1$ to $C_4$ alkyl group, $C_1$ to $C_4$ alkoxy group, cyano group, nitro group, carboxyl group, ($C_1$ to $C_6$ alkyl)oxycarbonyl group, etc. may be mentioned. One or more of these substituents may be substituted at any position of the phenyl group. In the case of plural substituents, any combination of the illustrated substituents may be used.

As preferable examples of the $C_1$ to $C_5$ alkoxy group serving as a substituent in the ($C_1$ to $C_5$ alkoxy group, substituted or unsubstituted phenyl group, substituted or unsubstituted phenoxy group, substituted or unsubstituted $C_3$ to $C_8$ cycloalkyl group, or substituted or unsubstituted heterocyclic group) substituted straight chain or branched ($C_1$ to $C_5$ alkyl group, $C_2$ to $C_5$ alkenyl group, or $C_2$ to $C_5$ alkynyl group), a methoxy group, ethoxy group, propoxy group, isopropoxy group, butoxy group, tert-butoxy group, hexyloxy group, etc. may be mentioned. As preferable examples of the $C_3$ to $C_8$ cycloalkyl group serving as the substituent, the preferred examples of the cycloalkyl groups of the above-mentioned $R^1$ may be mentioned. As preferable examples of the heterocyclic group serving as the substituent, a thienyl group, furanyl group, imidazolyl group, pyridyl group, pyrazynyl group, etc. may be mentioned. Among these substituents, a phenyl group, phenoxy group, cycloalkyl group, or heterocyclic group may further be substituted. As preferable examples of the substituent in this case, halogen atom, hydroxyl group, $C_2$ to $C_7$ acyloxy group, halogen atom-substitutable $C_1$ to $C_4$ alkyl group, halogen atom-substitutable $C_1$ to $C_4$ alkoxy group, cyano group, nitro group, carboxyl group, ($C_1$ to $C_6$)alkoxycarbonyl group, etc. may be mentioned. These substituents may be substituted at any of the ortho, meta, and para positions on the phenyl group. Further, any combination of a plurality of substituents may be used for the substitution.

As the straight chain or branched $C_1$ to $C_5$ alkyl group, $C_2$ to $C_5$ alkenyl group, and $C_2$ to $C_5$ alkynyl, a methyl group, ethyl group, propyl group, isopropyl group, butyl group, isobutyl group, sec-butyl group, tert-butyl group, pentyl group, allyl group, 3-butenyl group, 2-butenyl group, 4-pentenyl group, 2-pentenyl group, ethynyl group, 2-propynyl group, 1-propynyl group, 2-butynyl group, 3-butynyl group, etc. may be mentioned. The above substituent may be bonded at any position of the $C_1$ to $C_5$ alkyl group, $C_2$ to $C_5$ alkenyl group, or $C_2$ to $C_5$ alkynyl group.

Among these, as $R^4$, a $C_3$ to $C_8$ straight chain or branched alkyl group, substituted or unsubstituted $C_3$ to $C_{10}$ cycloalkyl group, or substituted or unsubstituted phenyl group-substituted straight chain or branched $C_1$ to $C_5$ alkyl group is preferred, in particular, a pentyl group, 2-methylhexyl group, cyclohexyl group, and substituted or unsubstituted benzyl group are particularly preferred.

In the prostaglandins of the above formula (I), Y indicates a $C_1$ to $C_5$ straight chain or branched alkyl group or $CO_2R^5$. $R^5$ indicates a hydrogen atom, $C_1$ to $C_{10}$ straight chain or branched alkyl group, or $C_2$ to $C_{10}$ straight chain or branched alkenyl group or one equivalent of cations.

Here, as the $C_1$ to $C_5$ straight chain or branched alkyl group serving as Y, a methyl group, ethyl group, propyl group, isopropyl group, butyl group, isobutyl group, sec-butyl group, tert-butyl group, pentyl group, etc. may be mentioned.

When $R^5$ indicates a $C_1$ to $C_{10}$ straight chain or branched alkyl group or $C_2$ to $C_{10}$ straight chain or branched alkenyl group, as preferable examples of the $C_1$ to $C_{10}$ straight chain or branched alkyl group, a methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group, etc. may be mentioned. Further, as preferable examples of the $C_2$ to $C_{10}$ straight chain or branched alkenyl group, a vinyl group, allyl group, 3-butenyl group, 2-butenyl group, 4-pentenyl group, 2-pentenyl group, prenyl group (3-methyl-2-butenyl group), 2,4-hexadienyl group, 2,6-octadienyl group, etc. may be mentioned.

As preferable examples of the one equivalent cation, $NH_4^-$, tetramethylammonium, monomethylammonium, dimethylammonium, trimethylammonium, benzylammonium, phenetylammonium, morpholinium cations, monoethanolammonium, piperidinium cations, and other ammonium cations; $Na^+$, $K^+$, and other alkali metal cations; ½ $Ca^{2+}$, ½ $Mg^{2+}$, ½ $Zn^{2+}$, ⅓ $Al^{3+}$, and other bivalent or trivalent metal cations etc. may be mentioned. Among these, as $R^5$, a hydrogen atom or methyl group is particularly preferred.

In the prostaglandins having the above formula (I), X indicates a methylene group or oxygen atom. Among these, as X, a methylene group is preferred.

In the prostaglandins having the above formula (I), W indicates a sulfur atom or sulfinyl group or methylene group. Among these, as W, a sulfur atom is most preferred.

In the prostaglandins having the above formula (I), the mark $=$ indicates a double bond or single bond. Among these, one where the mark $=$ indicates a double bond is most preferred.

Further, the compounds having the above formula (I) wherein the configuration of the substituent bonded on the cyclopentenone ring is the configuration derived from natural prostaglandin are particularly useful stereoisomers, but the present invention also includes their enantiomers, that is, stereoisomers having the following formula (I)ent.:

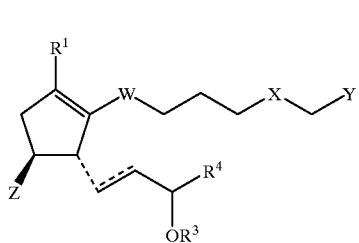

(I) ent.

wherein, $R^1$, $R^3$, $R^4$, W, X, Y, Z, and the mark $=$ have the same definitions as explained above or any mixture thereof at any ratio. Further, since an $OR^3$ or $R^4$ substituted carbon is an asymmetric carbon atom, there are two types of optical isomers. Either of these optical isomers or any mixture thereof at any ratio are also included.

As preferable specific examples of the prostaglandins having the above formula (I) of the present invention, the compounds shown below may be mentioned.

01) (11R,12R,13E,15S)-11,15-dihydroxy-9-methylprosta-8,13-dienoic acid 02) (11R,12R,13E,15S)-11,15-dihydroxy-9-ethylprosta-8,13-dienoic acid 03) (11R,12R,13E,15S)-11,15-dihydroxy-9-propylprosta-8,13-dienoic acid 04) (11R,12R,13E,15S)-11,15-dihydroxy-9-isopropylprosta-8,13-dienoic acid 05) (11R,12R,13E,15S)-11,15-dihydroxy-9-butylprosta-8,13-dienoic acid 06) (11R,12R,13E,15S)-11,15-dihydroxy-9-isobutylprosta-8,13-dienoic acid 07) (11R,12R,13E,15S)-11,15-dihydroxy-9-sec-butylprosta-8,13-dienoic acid 08) (11R,12R,13E,15S)-11,15-dihydroxy-9-tert-butylprosta-8,13-dienoic acid 09) (11R,12R,13E,15S)-11,15-dihydroxy-9-pentylprosta-8,13-dienoic acid 10) (11R,12R,13E,15S)-11,15-dihydroxy-9-cyclopropylprosta-8,13-dienoic acid 11) (11R,12R,13E,15S)-11,15-dihydroxy-9-neopentylprosta-8,13-dienoic acid 12) (11R,12R,13E,15S)-11,15-dihydroxy-9-hexylprosta-8,13-dienoic acid 13) (11R,12R,13E,15S)-11,15-dihydroxy-9-(3,3-dimethylbutyl)prosta-8,13-dienoic acid 14) (11R,12R,13E,15S)-11,15-dihydroxy-9-heptylprosta-8,13-dienoic acid 15) (11R,12R,13E,15S)-11,15-dihydroxy-9-octylprosta-8,13-dienoic acid 16) (11R,12R,13E,15S)-11,15-dihydroxy-9-cyclohexylprosta-8,13-dienoic acid 17) (11R,12R,13E,15S)-11,15-dihydroxy-9-decylprosta-8,13-dienoic acid 18) (11R,12R,13E,15S)-11,15-dihydroxy-9-cyanoprosta-8,13-dienoic acid 19) (11R,12R,13E,15S)-11,15-dihydroxy-9-formylprosta-8,13-dienoic acid 20) (11R,12R,13E,15S)-11,15-dihydroxy-9-carboxyprosta-8,13-dienoic acid 21) (11R,12R,13E,15S)-11,15-dihydroxy-9-methoxycarbonylprosta-8,13-dienoic acid 22) (11R,12R,13E,15S)-11,15-dihydroxy-9-ethoxycarbonylprosta-8,13-dienoic acid 23) (11R,12R,13E,15S)-11,15-dihydroxy-9-propoxycarbonylprosta-8,13-dienoic acid 24) (11R,12R,13E,15S)-11,15-dihydroxy-9-isopropoxycarbonylprosta-8,13-dienoic acid 25) (11R,12R,13E,15S)-11,15-dihydroxy-9-butoxycarbonylprosta-8,13-dienoic acid 26) (11R,12R,13E,15S)-11,15-dihydroxy-9-tert-butoxycarbonylprosta-8,13-dienoic acid 27) (11R,12R,13E,15S)-11,15-dihydroxy-9-pentyloxycarbonylprosta-8,13-dienoic acid 28) (11R,12R,13E,15S)-11,15-dihydroxy-9-acetylprosta-8,13-dienoic acid 29) (11R,12R,13E,15S)-11,15-dihydroxy-9-propionylprosta-8,13-dienoic acid 30) (11R,12R,13E,15S)-11,15-dihydroxy-9-butyrylprosta-8,13-dienoic acid 31) (11R,12R,13E,15S)-11,15-dihydroxy-9-isobutyrylprosta-8,13-dienoic acid 32) (11R,12R,13E,15S)-11,15-dihydroxy-9-valerylprosta-8,13-dienoic acid 33) (11R,12R,13E,15S)-11,15-dihydroxy-9-isovalerylprosta-8,13-dienoic acid 34) (11R,12R,13E,15S)-11,15-dihydroxy-9-pivaroylprosta-8,13-dienoic acid 35) (11R,12R,13E,15S)-11,15-dihydroxy-9-trifluoromethylprosta-8,13-dienoic acid 36) (11R,12R,13E,15S)-11,15-dihydroxy-9-trichloromethylprosta-8,13-dienoic acid 37) (11R,12R,13E,15S)-11,15-dihydroxy-9-fluoromethylprosta-8,13-dienoic acid 38) (11R,12R,13E,15S)-11,15-dihydroxy-9-chloromethylprosta-8,13-dienoic acid 39) (11R,12R,13E,15S)-11,15-dihydroxy-9-phenethylprosta-8,13-dienoic acid 40) (11R,12R,13E,15S)-11,15-dihydroxy-9-(3-phenylpropyl)prosta-8,13-dienoic acid 41) (11R,12R,13E,15S)-11,15-dihydroxy-9-(4-phenylbutyl)prosta-8,13-dienoic acid 42) (11R,12S,13E,15S)-11,15-dihydroxy-9-methyl-7-thiaprosta-8,13-dienoic acid 43) (11R,12S,13E,15S)-11,15-dihydroxy-9-ethyl-7-thiaprosta-8,13-dienoic acid 44) (11R,12S,13E,15S)-11,15-dihydroxy-9-cyclopropyl-7-thiaprosta-8,13-dienoic acid 45) (11R,12S,13E,15S)-11,15-dihydroxy-9-(3,3-dimethylbutyl)-7-thiaprosta-8,13-dienoic acid 46) (11R,12S,13E,15S)-11,15-dihydroxy-9-cyano-7-thiaprosta-8,13-dienoic acid 47) (11R,12S,13E,15S)-11,15-dihydroxy-9-formyl-7-thiaprosta-8,13-dienoic acid 48) (11R,12S,13E,15S)-11,15-dihydroxy-9-carboxy-7-thiaprosta-8,13-dienoic acid 49) (11R,12S,13E,15S)-11,15-dihydroxy-9-methoxycarbonyl-7-thiaprosta-8,13-dienoic acid 50) (11R,12S,13E,15S)-11,15-dihydroxy-9-acetyl-7-thiaprosta-8,13-dienoic acid 51) (11R,12S,13E,15S)-11,15-dihydroxy-9-trifluoromethyl-7-thiaprosta-8,13-dienoic acid 52) (11R,12S,13E,15S)-11,15-dihydroxy-9-phenethyl-7-thiaprosta-8,13-dienoic acid 53) (11R,12R,13E,15S,17R)-11,15-dihydroxy-9,17,20-trimethylprosta-8,13-dienoic acid 54) (11R,12R,13E,15S,17R)-11,15-dihydroxy-9-pentyl-17,20-dimethylprosta-8,13-dienoic acid 55) (11R,12R,13E,15S,17R)-11,15-dihydroxy-9-cyano-17,20-dimethylprosta-8,13-dienoic acid 56) (11R,12R,13E,15S,17R)-11,15-dihydroxy-9-formyl-17,20-dimethylprosta-8,13-dienoic acid 57) (11R,12R,13E,15S,17R)-11,15-dihydroxy-9-methoxycarbonyl-17,20-dimethylprosta-8,13-dienoic acid 58) (11R,12R,13E,15S,17R)-11,15-dihydroxy-9-acetyl-17,20-dimethylprosta-8,13-dienoic acid 59) (11R,12R,13E,15S,17R)-11,15-dihydroxy-9-trifluoromethyl-17,20-dimethylprosta-8,13-dienoic acid 60) (11R,12R,13E,15S,17R)-11,15-dihydroxy-9-cyclopropyl-17,20-dimethylprosta-8,13-dienoic acid 61) (11R,12S,13E,15S,17R)-11,15-dihydroxy-9,17,20-trimethyl-7-thiaprosta-8,13-dienoic acid 62) (11R,12S,13E,15S,17R)-11,15-dihydroxy-9-pentyl-17,20-dimethyl-7-thiaprosta-8,13-dienoic acid 63) (11R,12S,13E,15S,17R)-11,15-dihydroxy-9-(3,3-dimethylbutyl)-17,20-dimethyl-7-thiaprosta-8,13-dienoic acid 64) (11R,12S,13E,15S,17R)-11,15-dihydroxy-9-cyano-17,20-dimethyl-7-thiaprosta-8,13-dienoic acid 65) (11R,12S,13E,15S,17R)-11,15-dihydroxy-9-formyl-17,20-dimethyl-7-thiaprosta-8,13-dienoic acid 66) (11R,12S,13E,15S,17R)-11,15-dihydroxy-9-methoxycarbonyl-17,20-dimethyl-7-thiaprosta-8,13-dienoic acid 67) (11R,12S,13E,15S,17R)-11,15-dihydroxy-9-acetyl-17,20-dimethyl-7-thiaprosta-8,13-dienoic acid 68) (11R,12S,13E,15S,17R)-11,15-dihydroxy-9-trifluoromethyl-17,20-dimethyl-7-thiaprosta-8,13-dienoic acid 69) (11R,12S,13E,15S,17R)-11,15-dihydroxy-9-phenethyl-17,20-dimethyl-7-thiaprosta-8,13-dienoic acid 70) (11R,12R,13E,15S)-11,15-dihydroxy-9-methyl-16-phenyl-17,18,19,20-tetranolprosta-8,13-dienoic acid 71) (11R,12R,13E,15S)-11,15-dihydroxy-9-pentyl-16-phenyl-17,18,19,20-tetranolprosta-8,13-dienoic acid 72) (11R,12R,13E,15S)-11,15-dihydroxy-9-cyano-16-phenyl-17,18,19,20-tetranolprosta-8,13-dienoic acid 73) (11R,12R,13E,15S)-11,15-dihydroxy-9-formyl-16-phenyl-17,18,19,20-tetranolprosta-8,13-dienoic acid 74) (11R,12R,13E,15S)-11,15-dihydroxy-9-methoxycarbonyl-16-phenyl-17,18,19,20-tetranolprosta-8,13-dienoic acid 75) (11R,12R,13E,15S)-11,15-dihydroxy-9-acetyl-16-phenyl-17,18,19,20-tetranolprosta-8,13-dienoic acid 76) (11R,12R,13E,15S)-11,15-dihydroxy-9-trifluoromethyl-16-phenyl-17,18,19,20-tetranolprosta-8,13-dienoic acid 77) (11R,12R,13E,15S)-11,15-dihydroxy-9-phenethyl-16-phenyl-17,18,19,20-tetranolprosta-8,13-dienoic acid 78) (11R,12S,13E,15S)-11,15-dihydroxy-9-methyl-16-phenyl-17,18,19,20-tetranol-7-thiaprosta-8,13-dienoic acid 79) (11R,12S,13E,15S)-11,15-dihydroxy-9-pentyl-16-phenyl-17,18,19,20-tetranol-7-thiaprosta-8,13-dienoic acid 80) (11R,12S,13E,15S)-11,15-dihydroxy-9-cyano-16-phenyl-17,18,19,20-tetranol-7-thiaprosta-8,13-dienoic acid 81) (11R,12S,13E,15S)-11,15-dihydroxy-9-formyl-16-phenyl-17,18,19,20-tetranol-7-thiaprosta-8,13-dienoic acid 82) (11R,12S,13E,15S)-11,15-dihydroxy-9-methoxycarbonyl-16-phenyl-17,18,19,20-tetranol-7-thiaprosta-8,13-dienoic acid 83) (11R,12S,13E,15S)-11,15-dihydroxy-9-acetyl-16-phenyl-17,18,19,20-tetranol-7-thiaprosta-8,13-dienoic acid 84) (11R,12S,13E,15S)-11,15-dihydroxy-9-trifluoromethyl-16-phenyl-17,18,19,20-tetranol-7-thiaprosta-8,13-dienoic acid 85) (11R,12S,13E,15S)-11,15-dihydroxy-9-phenethyl-16-phenyl-17,18,19,20-tetranol-7-thiaprosta-8,13-dienoic acid 86) (11R,12S,13E,15S)-11,15-dihydroxy-9-cyclopropyl-16-phenyl-17,18,19,20-tetranol-7-thiaprosta-8,13-dienoic acid 87) (12R,13E,15S)-15-hydroxyl-9-methyl-16-phenyl-17,18,19,20-tetranol-7-thiaprosta-8,13-dienoic acid 88) (11R,12S,15R)-11,15-dihydroxy-9-methyl-16-phenyl-17,18,19,20-tetranol-7-thiaprosta-8-enoic acid 89) (11R,12S,13E,15S)-11,15-dihydroxy-9-trifluoromethyl-16-phenyl-17,18,19,20-tetranol-7-thiaprosta-8,13-dienoic acid 90) (11R,12S,13E,15S)-11,15-dihydroxy-9-methyl-16-phenyl-17,18,19,20-tetranol-3-oxa-7-thiaprosta-8,13-dienoic acid 91) (11R,12R,13E,15S)-11,15-dihydroxy-9-methyl-16-phenyl-17,18,19,20-tetranolprosta-8,13-dienoic acid 92) (11R,12S,13E,15S)-11,15-dihydroxy-9-methyl-16-phenyl-17,18,19,20-tetranol-3-oxa-7-sulfinylprosta-8,13-dienoic acid 93) (11R,12S,13E,15R,16S)-11,15-dihydroxy-9,16-dimethyl-16-phenyl-17,18,19,20-tetranol-3-oxa-7-thiaprosta-8,13-dienoic acid 94) (11R,12S,13E,15R,16R)-11,15-dihydroxy-9,16-dimethyl-16-phenyl-17,18,19,20-tetranol-3-oxa-7-thiaprosta-8,13-dienoic acid 95) (12R,13E,15R)-15-hydroxy-9,16-dimethyl-16-phenyl-17,18,19,20-tetranol-3-oxa-7-thiaprosta-8,13-dienoic acid 96) (12R,13E,15S)-15-hydroxy-9-methyl-16-phenyl-17,18,19,20-tetranol-3-oxa-7-thiaprosta-8,13-dienoic acid 97) (12R,13E,15S)-15-hydroxy-9-methyl-16-cyclohexyl-17,18,19,20-tetranol-3-oxa-7-thiaprosta-8,13-dienoic acid 98) (12R,15R)-15-hydroxy-9-methyl-16-phenyl-17,18,19,20-tetranol-3-oxa-7-thiaprosta-8-ene acid 99) (12R,15R)-15-hydroxy-9-methyl-15-cyclohexyl-16,17,18,19,20-pentanol-3-oxa-7-thiaprosta-8-enoic acid 100) (12R,13E,15S)-15-hydroxy-9-methyl-18-phenyl-19,20-dinol-3-oxa-7-thiaprosta-8,13-dienoic acid 101) (12R,13E,15S,17R)-15-hydroxy-9,17,20-trimethyl-3-oxa-7-thiaprosta-8,13-dienoic acid 102) (12R,13E,15S)-15-hydroxy-9-methyl-16-(2-thienyl-17,18,19,20-tetranol-3-oxa-7-thiaprosta-8,13-dienoic acid 103) (12R,13E,15R)-15-hydroxy-9-methyl-16-phenoxy-17,18,19,20-tetranol-3-oxa-7-thiaprosta-8,13-dienoic acid 104) (12R,13E,15S)-15-hydroxy-9-methyl-3-oxa-7-thiaprosta-8,13-dien-17-inoic acid 105) (12R,13E,15S,17E)-15-hydroxy-9,17-dimethyl-3-oxa-7-thiaprosta-8,13,17-trienoic acid 106) (12R,13E,15R)-15-hydroxy-9-methyl-15-phenyl-16,17,18,19,20-pentanol-3-oxa-7-thiaprosta-8,13-dienoic acid 107) (12R,13E,15R)-15-hydroxy-9-methyl-16-ethoxy-17,18,19,20-tetranol-3-oxa-7-thiaprosta-8,13-dienoic acid 108) (12R,13E,15S)-15-hydroxy-9-methyl-16-(3-chlorophenyl)-17,18,19,20-tetranol-3-oxa-7-thiaprosta-8,13-dienoic acid 109) (12R,13E,15R,16E)-15-hydroxy-9-methyl-17-(3-hydroxylphenyl)-18,19,20-trinol-3-oxa-7-thiaprosta-8,13,16-trienoic acid 110) (12R,13E,15S)-15-hydroxy-9-methyl-16-(3-methylphenyl)-17,18,19,20-tetranol-3-oxa-7-thiaprosta-8,13-dienoic acid 111) (12R,13E,15R)-15-hydroxy-9-methyl-15-(3-cyanophenyl)-16,17,18,19,20-pentanol-3-oxaprosta-8,13-dienoic acid 112) (12R,13E,15R)-15-hydroxy-9-methyl-15-(3-methoxyphenyl)-16,17,18,19,20-pentanol-3-oxaprosta-8,13-dienoic acid 113) (12R,13E,15R)-15-hydroxy-9-methyl-15-(4-hydroxylphenyl)-16,17,18,19,20-pentanol-3-oxaprosta-8,13-dienoic acid 114) (12R,13E,15R)-15-hydroxy-9-methyl-15-(3-acetoxyphenyl)-16,17,18,19,20-pentanol-3-oxaprosta-8,13-dienoic acid 115) (12R,13E,15R)-15-hydroxy-9-methyl-15-(3-nitrophenyl)-16,17,18,19,20-pentanol-3-oxaprosta-8,13-dienoic acid 116) (12R,13E,15R)-15-hydroxy-9-methyl-15-(3-carboxyphenyl)-16,17,18,19,20-pentanol-3-oxaprosta-8,13-dienoic acid 117) (12R,13E,15R)-15-hydroxy-9-methyl-15-(2-methoxycarbonylphenyl)-16,17,18,19,20-pentanol-3-oxaprosta-8,13-dienoic acid 118) (12R,13E,15R)-15-hydroxy-9-methyl-15-(4-imidazolyl)-16,17,18,19,20-pentanol-3-oxaprosta-8,13-dienoic acid 119) (12R,13E,15S)-15-hydroxy-9-methyl-16-(3-trifluoromethylphenyl)-17,18,19,20-tetranol-3-oxaprosta-8,13-dienoic acid 120) (12R,13E,15S)-15-hydroxy-9-methyl-16-(3-acetoxyphenyl)-17,18,19,20-tetranol-3-oxaprosta-8,13-dienoic acid 121) (12R,13E,15S)-15-hydroxy-9-methyl-16-[4-(2-chloroethoxy)phenyl]-17,18,19,20-tetranol-3-oxa-7-thiaprosta-8,13-dienoic acid 122) (12R,13E,15S)-15-hydroxy-9-methyl-16-(4-cyanophenyl)-17,18,19,20-tetranol-3-oxa-7-thiaprosta-8,13-dienoic acid 123) (12R,13E,15S)-15-hydroxy-9-methyl-16-(3-carboxyphenyl)-17,18,19,20-tetranol-3-oxa-7-thiaprosta-8,13-dienoic acid 124) (12R,13E,15S)-15-hydroxy-9-methyl-16-(4-nitrophenyl)-17,18,19,20-tetranol-3-oxa-7-thiaprosta-8,13-dienoic acid 125) (12R,13E,15S)-15-hydroxy-9-methyl-16-(4-methoxycarbonylphenyl)-17,18,19,20-tetranol-3-oxa-7-thiaprosta-8,13-dienoic acid 126) (12R,13E,15S)-15-hydroxy-9-methyl-16-(3-pyridyl)-17,18,19,20-tetranol-3-oxa-7-thiaprosta-8,13-dienoic acid 127) (12R,13E,15S)-15-hydroxy-9-methyl-16-(2-furanyl)-17,18,19,20-tetranol-3-oxa-7-thiaprosta-8,13-dienoic acid 128) Enantiomers of the compounds of 01) to 127)

129) Methyl esters of the compounds of 01) to 127)

130) Ethyl esters of the compounds of 01) to 127)

131) Butyl esters of the compounds of 01) to 127)

132) Allyl esters of the compounds of 01) to 127)

133) Sodium salts of the compounds of 01) to 127)

134) Compounds of the compounds of 01) to 127) where the carboxyl group (portion shown by Y) is substituted by a methyl group 135) Ethers of the compounds of 01) to 127) where the hydroxy groups (11-position and 15-position) are protected by a tert-butyldimethylsilyl group and/or trimethylsilyl group and/or 2-tetrahydropyranyl group etc. may be mentioned, but the invention is not limited to these. Further, optical isomers of the hydroxy group (15-position) portion of the ω chain of the compounds of 01) to 135) and all of their enantiomers may be mentioned.

On the other hand, in the prostaglandins of the above formula (II), V indicates a sulfur atom or sulfinyl group. As a preferable example, a sulfur atom may be mentioned. As specific examples of $R^3$, $R^4$, X, Y, Z, and the mark --, those mentioned as specific examples of $R^3$, $R^4$, X, Y, Z, and the mark -- in the above formula (I) may be mentioned as they are. Further, as preferable examples of these, those the same as in the case of the above formula (I) may be mentioned.

Further, the compounds of the above formula (II) wherein the configuration of the substituent bonded on the cyclopentenone ring is the configuration derived from natural prostaglandin are particularly useful stereoisomers, but the present invention also includes their enantiomers, that is, stereoisomers having the following formula (II)ent.:

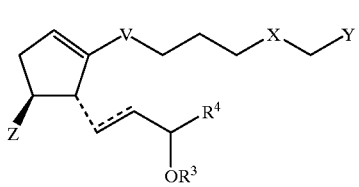

(II) ent.

wherein, $R^3$, $R^4$, V, X, Y, Z, and the mark -- have the same definitions as explained above, or any mixture thereof at any ratio. Further, since an $OR^3$ or $R^4$ substituted carbon is an asymmetric carbon, there are two types of optical isomers. Either of these optical isomers or any mixtures thereof at any ratio are also included.

As preferable specific examples of the prostaglandins having the above formula (II) of the present invention, the compounds shown below may be mentioned:

201) (11R,12S,13E,15S)-11,15-dihydroxy-7-thiaprosta-8,13-dienoic acid 202) (11R,12S,13E,15S,17R)-11,15-dihydroxy-17,20-dimethyl-7-thiaprosta-8,13-dienoic acid 203) (11R,12S,13E,15S)-11,15-dihydroxy-16-phenyl-17,18,19,20-tetranol-7-thiaprosta-8,13-dienoic acid 204) (11R,12S,13E,15S)-11,15-dihydroxy-16-phenyl-17,18,19,20-tetranol-7-sulfinylprosta-8,13-dienoic acid 205) (12R,13E,15R)-15-hydroxy-16-(4-chlorophenyl)-16-methyl-17,18,19,20-tetranol-3-oxa-7-thiaprosta-8,13-dienoic acid 206) (12R,15R)-15-hydroxy-16-(4-nitrophenyl)-17,18,19,20-tetranol-3-oxa-7-thiaprosta-8-ene acid 207) Enantiomers of the compounds of 201) to 206)

208) Methyl esters of the compounds of 201) to 206)

209) Ethyl esters of the compounds of 201) to 206)

210) Butyl esters of the compounds of 201) to 206)

211) Allyl esters of the compounds of 201) to 206)

212) Sodium salts of the compounds of 201) to 206)

213) Compounds of the compounds of 201) to 206) where the carboxyl group (portion shown by Y) is substituted by a methyl group 214) Ethers of the compounds of 201) to 206) where the hydroxy groups (11-position and 15-position) are protected by a tert-butyldimethylsilyl group and/or trimethylsilyl group and/or 2-tetrahydropyranyl group etc. may be mentioned, the present invention is not limited thereto. Further, optical isomers of the hydroxy group (15-position) portion of the ω chain of the compounds of 201) to 214) and all of their enantiomers may be mentioned.

Further, in the prostaglandins having the above formula (III), $W^1$ indicates a sulfur atom or methylene group, as a preferable example of which a sulfur atom may be mentioned. As specific examples of $R^3$, $R^4$, X, Y, Z, and the mark --, those mentioned as specific examples of $R^3$, $R^4$, X, Y, Z, and the mark -- in the above formula (I) may be mentioned. Further, as preferable examples thereof, the same ones as in the case of the above formula (I) may be mentioned.

Further, the compounds having the above formula (III) wherein the configuration of the substituent bonded on the cyclopentenone ring is the configuration derived from natural prostaglandin are particularly useful stereoisomers, but the present invention also includes their enantiomers, that is, stereoisomers having the following formula (III)ent.:

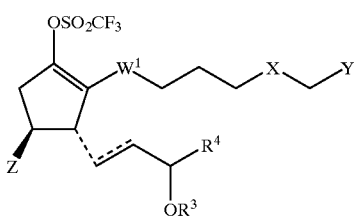

(III) ent.

wherein, $W^1$, $R^3$, $R^4$, X, Y, Z, and the mark -- have the same definitions as explained above, or any mixture thereof at any ratio. Further, since an $OR^3$ or $R^4$ substituted carbon is an asymmetric carbon, there are two types of optical isomers. Either of these optical isomers or any mixture thereof at any ratio are also included.

As preferable specific examples of the prostaglandins having the above formula (III) according to the present invention, the compounds shown below may be mentioned.

301) (11R,12R,13E,15S)-9-trifluoromethanesulfonyloxy-11,15-dihydroxyprosta-8,13-dienoic acid 302) (11R,12R,13E,15S,17R)-9-trifluoromethanesulfonyloxy- 11,15-dihydroxy-17,20-dimethylprosta-8,13-dienoic acid 303) (11R,12R,13E,15S)-9-trifluoromethanesulfonyloxy-11,15-dihydroxy-16-phenyl-17,18,19,20-tetranolprosta-8,13-dienoic acid 304) (11R,12S,13E,15S)-9-trifluoromethanesulfonyloxy-11,15-dihydroxy-7-thiaprosta-8,13-dienoic acid 305) (11R,12S,13E,15S,17R)-9-trifluoromethanesulfonyloxy-11,15-dihydroxy-17,20-dimethyl-7-thiaprosta-8,13-dienoic acid 306) (11R,12S,13E,15S)-9-trifluoromethanesulfonyloxy-11,15-dihydroxy-16-phenyl-17,18,19,20-tetranol-7-thiaprosta-8,13-dienoic acid 307) (11R,12S,13E,15S)-9-trifluoromethanesulfonyloxy-11,15-dihydroxy-16-phenyl-17,18,19,20-tetranol-3-oxa-7-thiaprosta-8,13-dienoic acid 308) (12R,13E,15S)-9-trifluoromethanesulfonyloxy-15-hydroxy-16-phenyl-17,18,19,20-tetranol-3-oxa-7-thiaprosta-8,13-dienoic acid 309) (12R,13E,15S)-9-trifluoromethanesulfonyloxy-15-hydroxy-16-phenyl-17,18,19,20-tetranol-7-thiaprosta-8,13-dienoic acid 310) (12R,13E,15S)-9-trifluoromethanesulfonyloxy-15-hydroxy-16-phenyl-17,18,19,20-tetranol-prosta-8,13-dienoic acid 311) Enantiomers of the compounds 301) to 310)

312) Methyl esters of the compounds 301) to 310)

313) Ethyl esters of the compounds 301) to 310)

314) Butyl esters of the compounds 301) to 310)

315) Allyl esters of the compounds 301) to 310)

316) Sodium salts of the compounds 301) to 310)

317) Compounds of the compounds 301) to 310) where the carboxyl group (portion shown by Y) is substituted by a methyl group 318) Ethers of the compounds 301) to 310) where the hydroxy groups (11-position and 15-position) are protected by a tert-butyldimethylsilyl group and/or trimethylsilyl group and/or 2-tetrahydropyranyl group etc. may be mentioned, but the present invention is not limited to these. Further, optical isomers of the hydroxy group (15-position) portion of the ω chain of the compounds of 301) to 318) and all of their enantiomers may be mentioned.

Further, the process of production of the prostaglandins according to the present invention having the above formulas (I), (II), and (III) is included in the present invention. That is, it comprises effecting a reaction between an organocopper compound prepared from an organolithium compound having the formula (IV):

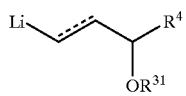

(IV)

wherein, $R^4$ has the same definition as explained above, and $R^{31}$ indicates a tri($C_1$ to $C_7$ hydrocarbon)silyl group or group forming an acetal bond with the oxygen atom of a hydroxy group and an organocopper compound prepared from a copper reagent having the formula:

CuQ wherein, Q indicates a 1-hexynyl group, 1-pentynyl group, or cyano group, and a 2-cyclopentenone having the formula (V):

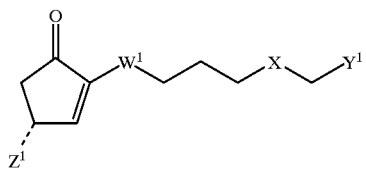

(V)

wherein, $Z^1$ indicates a hydrogen atom or $OR^{21}$, $R^{21}$ indicates a tri($C_1$ to $C_7$ hydrocarbon)silyl group or group forming an acetal bond with the oxygen atom of a hydroxy group, $Y^1$ indicates a $C_1$ to $C_5$ straight chain or branched alkyl group or $CO_2R^{51}$, $R^{51}$ indicates a $C_1$ to $C_{10}$ straight chain or branched alkyl group or $C_2$ to $C_{10}$ straight chain or branched alkenyl group, and $W^1$ and X have the same definitions as explained above] or its enantiomer or a mixture thereof at any ratio, then, further, causing a reaction with an sulfonimide acid having the formula (VI):

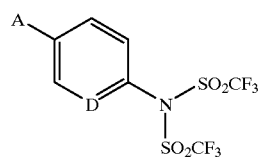

(VI)

wherein, A indicates a hydrogen atom or chlorine atom and D indicates a nitrogen atom or methine group to obtain the synthetic intermediate having the formula (VII):

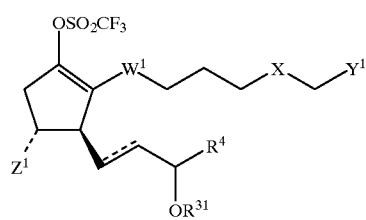

(VII)

wherein, $R^{31}$, $R^4$, $W^1$, X, $Y^1$, $Z^1$, and the mark -- have the same definitions as explained above, or its enantiomer or any mixture thereof at any ratio.

The synthetic process of the synthetic intermediate compound (VII) including the synthesis of the compound (III) may be illustrated as in scheme 1.

Scheme 1

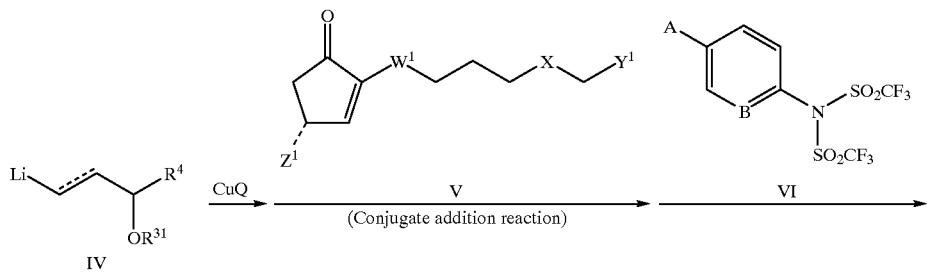

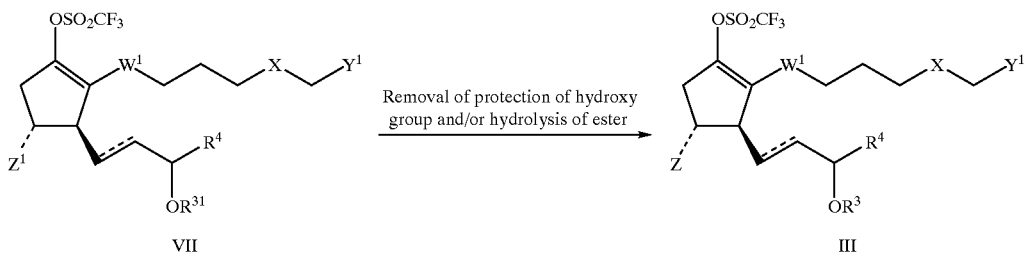

Removal of protection of hydroxy group and/or hydrolysis of ester

VII → III in which scheme, $R^3$, $R^{31}$, $R^4$, $W^1$, X, $Y^1$Y, $Z^1$, Z, A, D, and the mark $=$ have the same definitions as explained above.

In Scheme 1, if the starting material is made a racemate, since the synthesis proceeds stereospecifically with the intermediate as a mixture of the compound of the scheme and its enantiomers, if one of the compounds of the above formula (IV) or the above formula (V) is optically active, it is possible to separate it at a suitable stage (any stage of Scheme 1 or any stage in the synthesis of the compound (I) or compound (II) from the compound (III) so as to isolate the individual stereoisomers as pure products.

In the conjugate addition reaction of the first step of the method according to the present invention (Scheme 1), if, together with the organocopper compound, a trivalent organophosphorus compound, for example, trialkylphosphine (e.g., triethylphosphine, tributylphosphine, etc.), trialkylphosphate (e.g., trimethyl-phosphate, triethylphosphate, triisobutylphosphate, tributylphosphate, etc.), hexamethylphosphorus triamide, or triphenylphosphine is used, the conjugate addition reaction will proceed more smoothly. In particular, tributylphosphine or hexamethylphosphorus triamide is preferably used.

The process according to the present invention comprises effecting a reaction in the presence of an aprotonic inert organic solvent between an organolithium compound having the above formula (IV) and an organocopper compound prepared from CuQ, wherein Q has the same definition as explained above and a 2-cyclopentenone having the above formula (V), then effecting a reaction with the sulfonimide having the above formula (VI).

A 2-cyclopentenone and organocopper compound react equimolarly stoichiochemically, but usually 0.5 to 5.0, preferably 0.8 to 2.0, particularly preferably 1.0 to 1.5 moles of an organocopper compound are used based upon 1 mole of a 2-cyclopentenone.

The conjugate addition reaction of the 2-cyclopentenone and organocopper compound is carried out at a temperature range of −100° C. to 50° C., particularly preferably −78° C. to 0° C. The reaction time differs depending upon the reaction temperature, but usually it is sufficient to effect the reaction for about 1 hour at −78° C. to −20° C.

The reaction intermediate obtained by a conjugate addition reaction of a 2-cyclopentenone and organocopper compound reacts stoichiochemically equimolarly with sulfonimide, but usually the reaction is carried out under conditions giving an excess of sulfonimide. That is, the reaction is performed using 1.0 to 10.0, preferably 1.0 to 5.0 moles of sulfonimide based upon 1 mole of 2-cyclopentenone.

The reaction between the reaction intermediate obtained by a conjugate addition reaction of a 2-cyclopentenone and organocopper compound and the sulfonimide is carried out at a temperature of −30° C. to 50° C., particularly preferably −30° C. to 30° C. or so. The reaction time differs depending upon the reaction temperature, but usually it is sufficient to carry out the reaction for about 15 minutes at 0° C. to 20° C.

This reaction is carried out in the presence of an inert aprotonic organic solvent which is liquid under the reaction temperature and does not react with the reaction reagents. As the aprotonic inert organic solvent, for example, saturated hydrocarbons such as pentane, hexane, heptane, cyclohexane, aromatic hydrocarbons such as benzene, toluene, xylene, ether type solvents such as diethylether, tetrahydrofuran, dioxane, dimethoxyethane, diethylene glycol dimethylether, and also other so-called aprotonic polar solvents such as hexamethylphospholicamide (HMP), N,N-dimethylformamide (DMF), N,N-dimethylacetoamide (DMA), dimethylsulfoxide (DMSO), sulforan, N-methylpyridone may be mentioned. Any mixture of the two or more types of these solvents may be used. Further, as the aprotonic inert organic solvent, the inert solvent used to prepare the organocopper compound may be used as it is. That is, in this case, the reaction may be carried out by adding into a reaction system used for preparing the organocopper compound a 2-cyclopentenone. The amount of the organic solvent used need only be an amount sufficient for the smooth progress of the reaction. Normally, 1 to 100 times the volume of the starting material, preferably 2 to 20 times, is used.

As explained above, it is possible to make a trivalent organophosphorus compound be present at the time of preparation of the organocopper compound and possible to add to that system a 2-cyclopentenone to perform the reaction. As a result, a compound (VII) of the compound having the above formula (III) where the hydroxy group is protected and the $R^5$ portion is an ester is obtained.

The process of production according to the present invention uses a reaction which proceeds stereospecifically, so compounds having the configuration of the above formula (III) are obtained from starting materials having the configuration of the above formula (V) and compounds having the configuration of the following formula (VII)ent.:

(VII) ent.

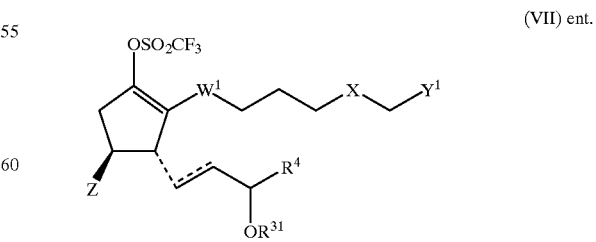

wherein $R^{31}$, $R^4$, $W^1$, X, $Y^1$, $Z^1$, and the mark $=$ are the same as in the above formula are obtained from the enantiomers having the above formula (V).

After the reaction, the resultant product is separated from the reaction solution and purified by an ordinary means such as extraction, washing, chromatography, or any combinations thereof.

The compound (VII) obtained by the above method wherein the hydroxy group is protected and the $COOR^5$ portion serving as Y is an ester may, optionally, have the protection removed or be subjected to hydrolysis. The protecting group ($R^{21}$ and/or $R^{31}$) of the hydroxy group may be removed by, when the protecting group is a group forming an acetal bond together with the oxygen atom of the hydroxy group, by using, for example, acetic acid, a p-toluenesulfonic acid pyridinium salt, or cation ion exchange resin as a catalyst and using for example, water, tetrahydrofuran, dioxane, acetone, acetonitrile, etc. as a reaction solution. The reaction is normally performed at a temperature range of $-78°$ C. to $50°$ C. for 10 minutes to 3 days or so. Further, when the protecting group is a tri($C_1$ to $C_7$ hydrocarbon)silyl group, for example, the protecting group may be removed under similar conditions using acetic acid, p-toluenesulfonic acid pyridinium salt, tetrabutylammonium fluoride, cesium fluoride, hydrofluoric acid, or hydrogenfluoride-pyridine as a catalyst.

In the case of a compound where the protecting group is removed and the water solubility is high, the ester of the compound where the $COOR^5$ portion is an ester may be hydrolyzed by effecting a reaction using or example lipase, esterase, or other enzyme in water or a solvent containing water at a temperature range of $-10°$ C. to $60°$ C. for 10 minutes to 24 hours.

Further, as shown below, it is possible to derive from a compound having the above formula (VII) a compound of the above formula (I) or (II) by various reactions using a palladium catalyst.

The prostaglandin of the present invention having the above formula (I) where $R^1$ is a $C_1$ to $C_{10}$ straight chain or branched alkyl group, cyano group, or halogen- or substituted or unsubstituted phenyl group-substituted $C_1$ to $C_5$ alkyl group may be produced by effecting coupling in an inert gas atmosphere in the presence of a palladium catalyst between a compound having the above formula (VII) or its enantiomer or any mixture of the enantiomers at any ratio and an organoboron compound having the following formula (VIII):

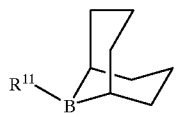

(VIII)

wherein, $R^{11}$ indicates a $C_1$ to $C_{10}$ straight chain or branched alkyl group or $C_1$ to $C_5$ alkyl group substituted with (a) halogen atom(s) or substituted or unsubstituted phenyl group(s).

an organoaluminum compound having $R^{12}{}_3Al$ wherein, $R^{12}$ indicates a $C_1$ to $C_{10}$ straight chain or branched alkyl group or a substituted or unsubstituted phenyl group-substituted $C_1$ to $C_5$ alkyl group, an organozinc compound having $R^{13}ZnI$ wherein, $R^{13}$ indicates a $C_1$ to $C_{10}$ straight chain or branched alkyl group or a fluorine atom-substituted $C_1$ to $C_5$ alkyl group, an organotin compound of $R^{14}SnBu_3$ wherein, $R^{14}$ indicates a $C_1$ to $C_{10}$ straight chain or branched alkyl group or a substituted or unsubstituted phenyl group-substituted $C_1$ to $C_5$ alkyl group, or a cyanide having LCN wherein, L indicates a sodium atom or a potassium atom to obtain a compound having the following formula (I-1):

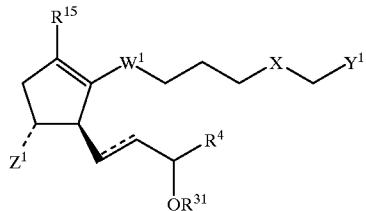

(I-1)

wherein, $R^{15}$ indicates a $C_1$ to $C_{10}$ straight chain or branched alkyl group, cyano group, or halogen atom- or substituted or unsubstituted phenyl group-substituted $C_1$ to $C_5$ alkyl group and $R^{31}$, $R^4$, $W^1$, X, $Y^1$, $Z^1$, and the mark -- have the same definitions as explained above, its enantiomer or any mixture thereof at any ratio and, optionally, by removing the protection and/or performing a hydrolysis reaction.

The synthesis process of the prostaglandins according to the present invention having the above formula (I) where $R^1$ indicates a $C_1$ to $C_{10}$ straight chain or branched alkyl group, cyano group, or halogen- or substituted or unsubstituted phenyl group-substituted $C_1$ to $C_5$ alkyl group, if illustrated from the compound (VII), becomes as shown in Scheme 2:

Scheme 2

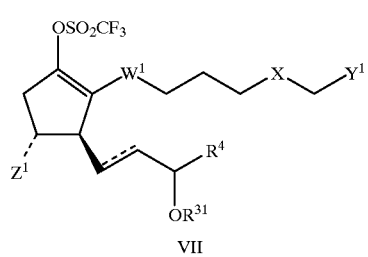 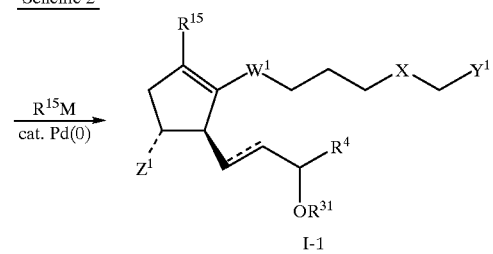

VII          I-1

-continued

Removal of protection from hydroxyl group and/or hydrolysis of ester →

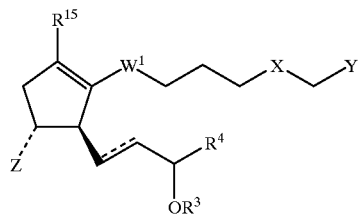

in which scheme, $R^{15}M$ indicates a compound having the above formula (VIII), $R^{12}{}_3Al$, $R^{13}ZnI$, $R^{14}SnBu_3$, or LCN. $R^{11}$, $R^{12}$, $R^{13}$, $R^{14}$, $R^{15}$, $R^3$, $R^{31}$, $R^4$, $W^1$, X, Y, $Y^1$, Z, $Z^1$, and the mark -- have the same definitions as explained above.

In the coupling reaction of the first step of the method according to the present invention (Scheme 2), as the palladium catalyst, a 0-valent or bivalent complex may be used. For example, tris(benzylidenacetone)dipalladium (0), bis[1,2-bis(diphenylphosphino)ethane]palladium (0), tetrakistriphenylphosphinepalladium (0), palladium acetate, bistriphenylphosphinepalladium(II)acetate, bistriphenylphosphinepalladium(II)chloride, etc. may be mentioned. To reduce the amount of the palladium complex required to end the reaction, it is sometimes better to add to the reaction system phosphine or another ligand. In particular, with a palladium complex where there is no phosphine ligand in the complex such as tris(dibenzylidenacetone)dipalladium(0) or palladium acetate, in many cases the reaction is performed adding a ligand to the reaction system. As the ligand added, triphenylphosphine, diphenylphosphinoethane, tributylphosphine, triethylphosphine, triethylphosphate, etc. may be mentioned. The amount of the palladium complex usable for the reaction is 0.1 to 50 mol % based upon the substrate compound (VII). The amount of addition in the case of adding a ligand is 0.2 to 8 equivalents or so based upon the palladium.

The coupling reaction of the first step is performed in the presence of an organic solvent. An inert aprotonic organic solvent which is liquid under the reaction temperature and does not react with the reaction reagents is used. As this aprotonic inert organic solvent, for example, aromatic hydrocarbons such as pentane, hexane, heptane, cyclohexane, or other saturated hydrocarbon, benzene, toluene, xylene, ether solvents such as diethylether, tetrahydrofuran, dioxane, dimethoxyethane, diethylene glycol dimethylether, or other so-called aprotonic polar solvents such as hexamethylphospholicamide (HMP), N,N-dimethylformamide (DMF), N,N-dimethylacetoamide (DMA), dimethylsulfoxide (DMSO), sulforan, N-methylpyrrolidone may be mentioned. Two or more types of solvents may be also used as a mixture together. The amount of the organic solvent used need only be such that the reaction is smoothly proceeded. Normally, 1 to 100 times, preferably 2 to 20 times, of the organic solvent, based upon the volume of the starting material is used.

The coupling reaction of the first step is performed using an organoboron compound, organoaluminum compound, organozinc compound, organotin compound, or cyan compound. These need only be stoichiochemically equimolar with the substrate compound (VII), but in actuality 0.5 to 10.0 equivalents are used. Preferably 1.0 to 5.0 equivalents are used. The coupling reaction of the first step is carried out at a reaction temperature of about 0 to 100° C., preferably, 15 to 70° C.

Note that when using an organoboron compound to carry out the coupling reaction, it is necessary to place a base such as tripotassium phosphate, sodium hydroxide, sodium ethoxide, lithium hydroxide, sodium hydrogencarbonate in the system. This base need only be stoichiochemically equimolar with the substrate compound (VII), but practically 0.5 to 10.0 equivalents are used. Preferably 1.0 to 5.0 equivalents are used. As a result, the compound having the above formula (I-1) is obtained.

After the reaction, the resultant product is separated from the reaction solution and refined by a means such as the removal of catalyst by Florisil or Celite filtration, extraction, washing, chromatography, etc.

The compound thus obtained (compound where the hydroxy group is protected and the $COOR^5$ portion serving as Y is an ester) may have the protection removed and be hydrolyzed by a method similar to the method mentioned in the explanation of Scheme 1.

The prostaglandins according to the present invention having the above formula (I) where $R^1$ indicates a formyl group are produced by carbonylating a compound having the above formula (VII) or its enantiomer or any mixture thereof at any ratio, for example, in a 1 to 50 atmosphere carbon monoxide atmosphere using a palladium catalyst, by reacting the intermediate with hydrogen gas or ammonium formate or formic acid and a tertiary amine salt to obtain a compound having the formula (I-2):

(I-2)

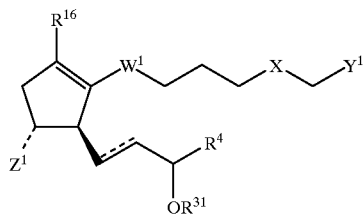

wherein, $R^{16}$ is a formyl group and $R^{31}$, $R^4$, $W^1$, X, $Y^1$, $Z^1$, and the mark -- have the same definitions as explained above or its enantiomer or any mixture thereof at any ratio and, optionally removing the protection and/or applying a hydrolysis reaction.

The synthesis process of the prostaglandin according to the present invention having the above formula (I) where $R^1$ is a formyl group, if illustrated from compound (VII), becomes as shown in Scheme 3.

Scheme 3

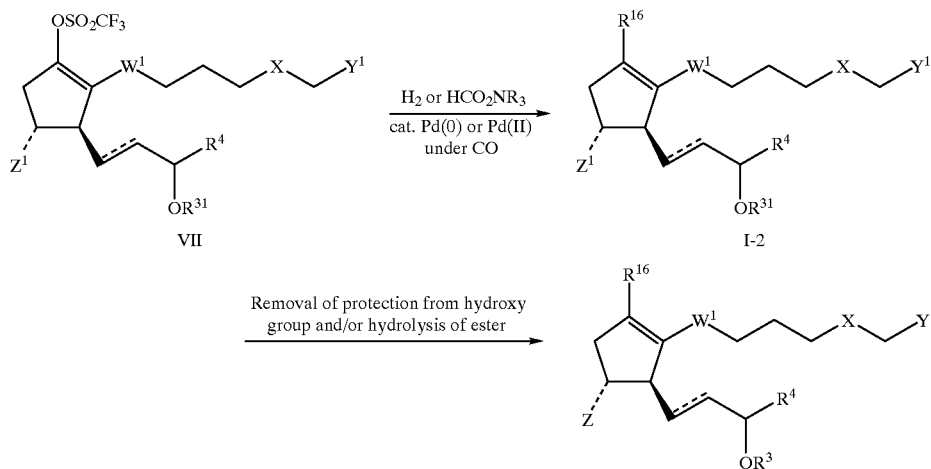

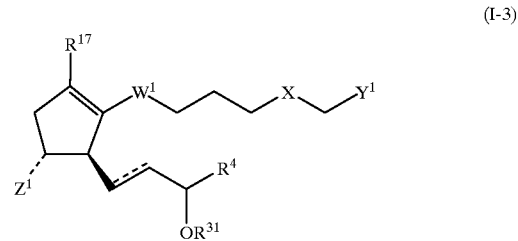

in which scheme, $R^{16}$, $R^3$, $R^{31}$, $R^4$, $W^1$, X, Y, $Y^1$, Z, $Z^1$, and the mark -- have the same definitions.

As specific examples of the palladium catalyst used in the formylation reaction of the first step of the method according to the present invention (Scheme 3) and the amount used, the catalysts and amounts used mentioned in the explanation of the reaction of the first step of Scheme 2 may be applied as they are.

The formylation reaction of the first step is carried out in the presence of an organic solvent. As the specific solvent and the amount used, the solvents and amounts used mentioned in the explanation of the reaction of the first step of Scheme 2 may be applied as they are.

The formylation reaction of the first step of Scheme 3 requires that the compound (VII) be carbonylated in a carbon monoxide atmosphere, but therefore the reaction vessel must be subjected to a pressure of about 1 to 50 atmospheres by carbon monoxide. To carry out the reaction quickly, a higher carbon monoxide pressure is advantageous.

Further, in this formylation, the reaction intermediate produced from the compound (VII) and carbon monoxide must be reacted with hydrogen, but, as the hydrogen source, it is possible to use hydrogen gas or ammonium formate or formic acid and a tertiary amine salt. When using hydrogen gas, it is sufficient to include it as a gaseous mixture with the carbon monoxide. The ratio of the hydrogen gas and carbon monoxide is 1 to 9 to 9 to 1. When using ammonium formate or formic acid and a tertiary amine salt as the hydrogen source, it must be stoichiochemically equimolar with respect to the substrate compound (VII), but 0.5 to 10.0 equivalents as formic acid is practically used. Preferably 1.0 to 5.0 equivalents are used. Commercially available ammonium salts may be used as they are or triethylamine or another base may be added to formic acid dissolved in a solution to adjust the acidity. The amount of the base used is basically equimolar with the formic acid and the reaction system is made neutral, but considering the acid resistance and base resistance of the reaction substrate, the conditions need not be neutral so long as the conditions are such that the compound will not decompose.

The reaction temperature of the formylation reaction of the first step of Scheme 3 is about 0 to 150° C. It is difficult to perform the reaction at a temperature above the boiling point of the solvent used in usual reactions, but when using a pressure resistant vessel, it is possible to perform the reaction at a temperature over the boiling point of the solvent. As a result, a compound having the above formula (I-2) is obtained.

After the reaction, the resultant product is separated from the reaction solution and refined by a means such as, the removal of the catalyst by Florisil or Celite filtration or extraction, washing, chromotography, etc.

The compound thus obtained (compound where the hydroxy group is protected and the $COOR^5$ portion as Y is an ester) may have the protection removed and be hydrolyzed by a method similar to the method mentioned in the explanation of Scheme 1.

The compounds of the prostaglandins according to the present invention having the above formula (I) where $R^1$ indicates a carboxyl group or ($C_1$ to $C_5$ alkyl)oxycarbonyl group are produced by placing a compound of the above formula (VII) or its enantiomer or any mixture thereof at any ratio in a carbon monoxide atmosphere in the presence of a $C_1$ to $C_5$ alcohol or water and performing carbonylation using a palladium catalyst to obtain a compound having the following formula (I-3):

(I-3)

wherein, $R^{17}$ indicates a carboxyl group or $C_1$ to $C_5$ alkoxycarbonyl group, and $R^{31}$, $R^4$, $W^1$, X, $Y^1$, $Z^1$, and the mark—have the same definitions as explained above, or its enantiomer or any mixture thereof at any ratio and, optionally, removing the protection and/or performing a hydrolysis reaction.

The synthesis path of the prostaglandins of the present invention having the above formula (I), wherein $R^1$ is a carboxyl group or ($C_1$ to $C_5$ alkyl)oxycarbonyl group, if illustrated from the compound (VII), becomes as shown in Scheme 4.

Scheme 4

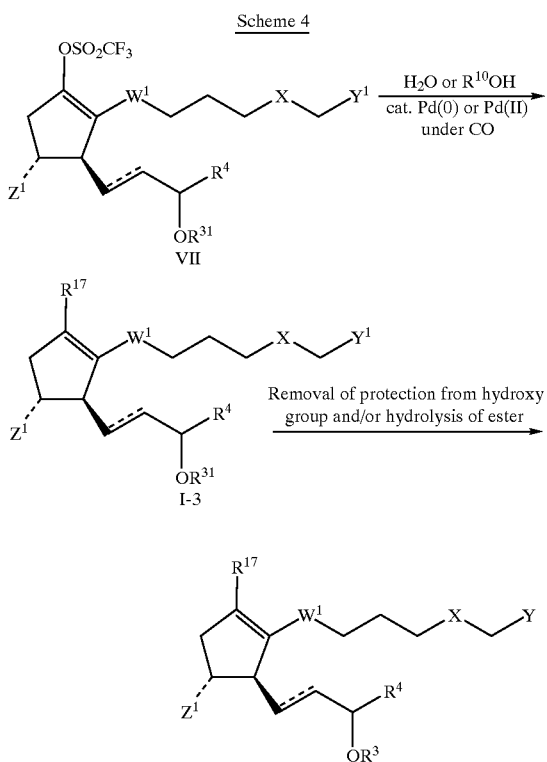

in which scheme, $R^{17}$, $R^3$, $R^{31}$, $R^4$, $W^1$, X, Y, $Y^1$, Z, $Z^1$, and the mark—have the same definitions as explained above.

In the carbonylation reaction of the first step of the method according to the present invention (Scheme 4), as the palladium catalyst, a 0-valent or bivalent complex may be used. For example, tris(benzylideneacetone)dipalladium(0), bis[1,2-bis(diphenylphosphin)ethane]palladium(0), tetrakistriphenylphosphinepalladium(0), palladium acetate, bistriphenylphosphinepalladium(II)acetate, etc. may be mentioned. For the amount of use of the palladium catalyst and the use of ligands, the examples in the explanation of the reaction of the first step of Scheme 2 apply as they are The carbonylation reaction of the first step of Scheme 4 is carried out in the presence of an organic solvent. As the specific solvent and the amount used, the solvents and amounts used mentioned in the explanation of the reaction of the first step of Scheme 2 may be used.

The carbonylation reaction of the first step of Scheme 4 requires that the compound (VII) be carbonylated in a carbon monoxide atmosphere. Therefore, the reaction vessel must be pressurized by carbon monoxide to normally 1 to 50 atmospheres or so. To carry out the reaction quickly, a higher carbon monoxide pressure is advantageous.

Further, in this carbonylation reaction, the reaction intermediate produced from the compound (VII) and carbon monoxide is reacted with the water or alcohol present in the system. The water or alcohol need be stoichiochemically equimolar, but practically 0.5 to 10.0 equivalents are used. Preferably 1.0 to 5.0 equivalents are used.

The carbonylation reaction of the first step is carried out at a reaction temperature of about 0 to 100° C., preferably, 15 to 70° C. As a result, the compound of the above formula (I-3) is obtained.

After the reaction, the resultant product is separated from the reaction solution and refined by a means such as the removal of the catalyst by Florisil or Celite filtration extraction, washing, chromotography, etc.

The compound thus obtained (compound where the hydroxy group is protected and the $COOR^5$ portion serving as Y is an ester) may have the protection removed and be hydrolyzed by a method similar to the method mentioned in the explanation of Scheme 1.

The prostaglandins according to the present invention having the above formula (I), wherein $R^1$ is a $C_2$ to $C_7$ alkanoyl group, are produced by reacting the compound having the above formula (VII) or its enantiomer or any mixture thereof at any ratio in a carbon monoxide atmosphere with a palladium catalyst and an organoboron compound having the formula (VIII'):

(VIII')

wherein, $R^{111}$ indicates a $C_1$ to $C_6$ straight chain or branched alkyl group;

an organoaluminum compound having the formula:

wherein, $R^{121}$ indicates a $C_1$ to $C_6$ straight chain or branched alkyl group;

an organozinc compound having the formula:

wherein, $R^{131}$ indicates a $C_1$ to $C_6$ straight chain or branched alkyl group;

or an organotin compound having the formula:

wherein, $R^{141}$ indicates a $C_1$ to $C_6$ straight chain or branched alkyl group to obtain the alkanoylated compound having the following formula (I-4):

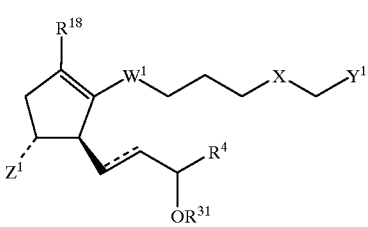

(I-4)

wherein, $R^{18}$ indicates a $C_2$ to $C_7$ alkanoyl group and $R^{31}$, $R^4$, $W^1$, X, $Y^1$, $Z^1$ and the mark—have the same definitions as explained above or its enantiomer or any mixture of the enantiomers at any ratio and, optionally, removing the protection and/or applying a hydrolysis reaction.

The synthesis process of the prostaglandins according to the present invention having the above formula (I) where $R^1$ is an $C_1$ to $C_7$ alkanoyl group, if illustrated from compound (VII), becomes as shown in the Scheme 5.

Scheme 5

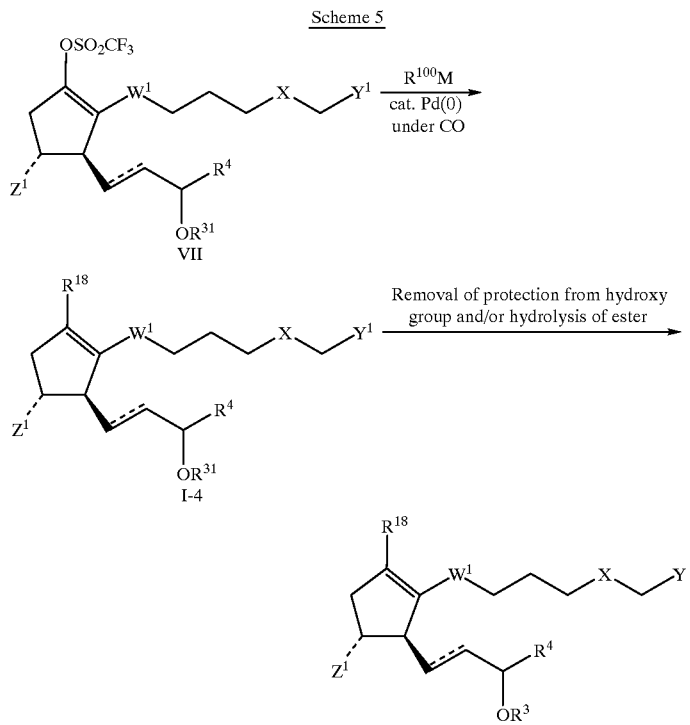

in which Scheme, $R^{100}$ M indicates one of a compound having the above formula (VIII'), $R^{121}{}_3Al$, $R^{131}ZnI$, or $R^{141}SnBu_3$ and $R^{111}$, $R^{121}$, $R^{131}$, $R^{141}$, $R^3$, $R^{31}$, $R^4$, $W^1$, X, Y, $Y^1$, Z, $Z^1$, and the mark—have the same definitions.

In the alkanoylation reaction of the first step of the method according to the present invention (Scheme 5), as the palladium catalyst, a 0-valent complex may be used. For example, tris (benzylideneacetone)dipalladium(0), bis[1,2-bis(diphenylphosphin)ethane]palladium(0), tetrakistriphenylphosphinepalladium(0), etc. may be mentioned. The amount of the palladium catalyst used and the ligands mentioned in the explanation of the reaction according to the first step of Scheme 2 may be used.

The alkanoylation reaction according to the first step of Scheme 5 is performed in the presence of an organic solvent. As the specific solvent and the amount used, the solvents and amounts used mentioned in the explanation of the reaction of the first step of Scheme 2 may be used.

The alkanoylation reaction of the first step of Scheme 5 requires that the compound (VII) be carbonylated in a carbon monoxide atmosphere. Therefore, the reaction vessel must be pressurized by carbon monoxide to normally 1 to 50 atmospheres or so. To carry out the reaction quickly, a higher carbon monoxide pressure is advantageous.

Further, in this reaction, the reaction intermediate produced from the compound (VII) and carbon monoxide reacts with an organoboron compound, organoaluminum compound, organozinc compound, or organotin compound. These have to be stoichiochemically equimolar to the substrate compound (VII), but in actuality 0.5 to 10.0 equivalents are used. Preferably 1.0 to 5.0 equivalents are used. The alkanoylation reaction of the first step is performed at a reaction temperature of about 0 to 150° C. As a result, the compound of the above formula (I-4) is obtained.

After the reaction, the resultant product is separated from the reaction solution and refined by a means such as the removal of the catalyst by Florisil or Celite filtration extraction, washing, chromotography, etc.

The compound thus obtained (compound where the hydroxy group is protected and the $COOR^5$ portion serving as Y is an ester) may have the protection removed and be hydrolyzed by a method similar to the method mentioned in the explanation of Scheme 1.

The process of production of the prostaglandins according to the present invention having the above formula (II), comprises reducing a compound having the following formula (VII'):

(VII')

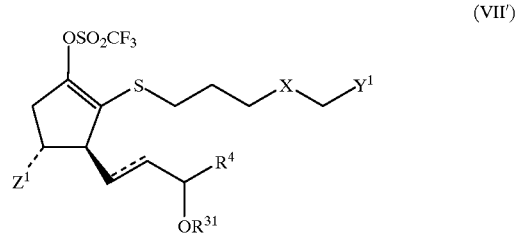

wherein, $R^{31}$, $R^4$, X, $Y^1$, $Z^1$, and the mark—have the same definitions as explained above or its enantiomer or any mixture of the enantiomers at any ratio in the presence of a palladium catalyst by formic acid and, optionally need, removing the protection and/or applying a hydrolysis reaction.

The synthesis process of the prostaglandins according to the present invention having the above formula (II), if illustrated from compound (VII'), becomes as shown in the Scheme 6.

Scheme 6

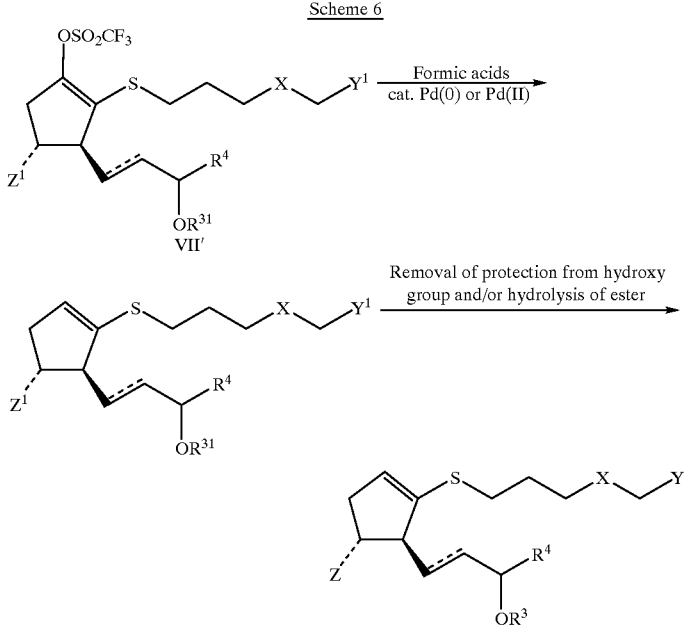

in which scheme, $R^3$, $R^{31}$, $R^4$, X, Y, $Y^1$, Z, $Z^1$, and the mark—have the same definitions as explained above.

As the palladium catalyst used in the reduction reaction of the first step of the method according to the present invention (Scheme 6) and the amount used, the catalysts and amounts used mentioned in the explanation of the reaction according to the first step of Scheme 2 may be used. Further, regarding the amount of the ligand used, the examples given in the explanation of the reaction according to the first step of Scheme 2 may be applied as they are.

The reduction reaction of the first step is carried out in the presence of an organic solvent. As the specific solvent and the amount used, the solvents and amounts used mentioned in the explanation of the reaction of the first step of Scheme 2 may be used.

The reduction reaction of the first step is carried out on the compound (VII') using formic acids as a hydrogen source, but as the formic acids, in addition to formic acid, ammonium formate or formic acid and a tertiary amine salt may be used. The ammonium formate or formic acid and tertiary amine salt have to be stoichiochemically equimolar with the substrate compound (VII'), but practically 0.5 to 10.0 equivalents as formic acid are used. Preferably 1.0 to 5.0 equivalents are used. Commercially available ammonium salts may be used as they are or triethylamine or another base may be added to formic acid dissolved in a solution to adjust the acidity. The amount of the base used is basically equimolar with the formic acid and the reaction system is made neutral, but considering the acid resistance and base resistance of the reaction substrate, the conditions need not be neutral so long as the conditions are such that the compound will not decompose. The reduction reaction of the first step is carried out at a reaction temperature of about 0 to 100° C. Preferably it is performed at about 20 to 70° C.

As a result, a compound having the above formula (II) where the hydroxy group is protected and the $COOR^5$ portion serving as Y is an ester is obtained. After the reaction, the product thus obtained is separated from the reaction solution and refined by a means the removal of the catalyst by Florisil or Celite filtration or such as extraction, washing, chromatography, etc.

The compound thus obtained (compound where the hydroxy group is protected and the $COOR^5$ portion serving as Y is an ester) may have the protection removed and be hydrolyzed by a method similar to the method mentioned in the explanation of Scheme 1.

The prostaglandins of the present invention having the above formula (I) where $R^1$ indicates a $C_3$ to $C_8$ cycloalkyl group or straight chain or branched $C_1$ to $C_{10}$ alkyl group are synthesized from compound (VII) by the synthesis process of the following (Scheme 7).

Scheme 7

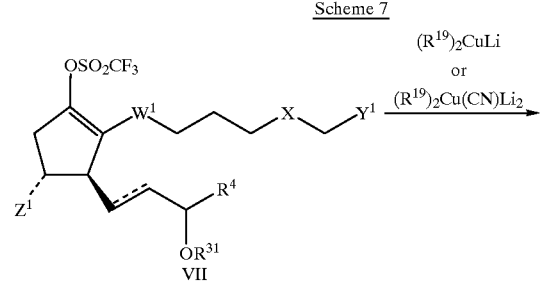

-continued

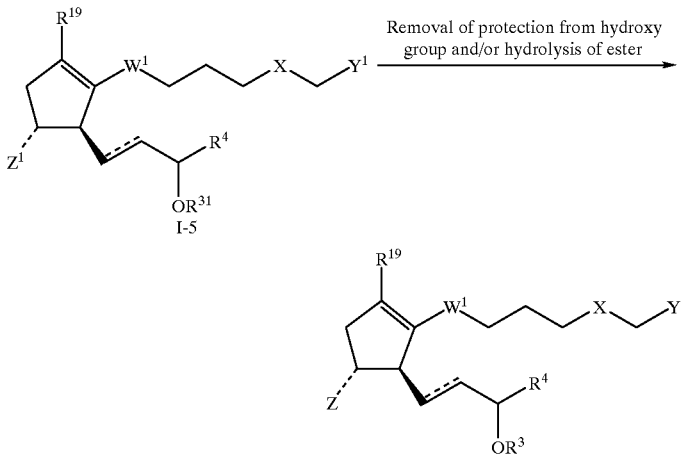

in which scheme, $R^{19}$ indicates a $C_3$ to $C_8$ cycloalkyl group or straight chain or branched $C_1$ to $c_{10}$ alkyl group and $R^3$, $R^{31}$, $R^4$, $W^1$, X, Y, $Y^1$, Z, $Z^1$, and the mark——have the same definitions as explained above.

The reaction of the first step according to the process of the present invention (Scheme 7) is performed in the presence of an aprotonic inert organic solvent by reacting an organocopper compound and a compound having the above formula (VII).

The compound having the above formula (VII) and organocopper compound react stoichiochemically equimolarly, but usually 0.5 to 5.0, preferably 0.8 to 2.0, particularly preferably 1.0 to 1.5 moles of organocopper compound based upon 1 mole of the compound of formula (VII) is used. The reaction is carried out at a temperature of −100° C., to 50° C., particularly preferably −78° C. to 10 C.

The reaction is carried out in the presence of an organic solvent. An inert aprotonic organic solvent, which is liquid at the reaction temperature, is used and does not react with the reaction reagents. As examples of this aprotonic inert organic solvent, the solvents mentioned in the explanation of Scheme 1, which may be used in similar amounts, are used.

After the reaction, the product thus obtained is separated and refined by ordinary means. For example, this is performed by extraction, washing, chromatography, or the combinations thereof.

The compound thus obtained (compound where the hydroxy group is protected and the $COOR^5$ portion as Y is an ester) may have the protection removed and be hydrolyzed by a method similar to the method mentioned in the explanation of Scheme 1.

The prostaglandins of the present invention having the above formula (I) or (II) where W or V is a sulfinyl group may be easily synthesized by converting the sulfur atom of the above compounds (I-1), (I-2), (I-3), (I-4), (I-5) or the compound having the following formula (X):

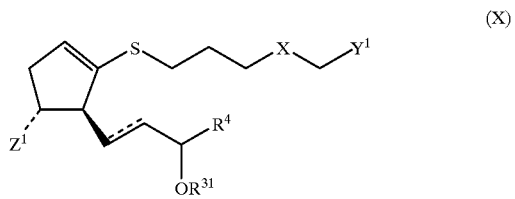

(X)

wherein $R^{31}$, $R^4$, X, $Y^1$, $Z^1$, and the mark——have the same definitions as explained above to a sulfinyl group by oxidation by peracid or peroxide and, optionally, having the protection removed and/or applying a hydrolysis reaction.

According to the present invention, a compound having a carboxyl group obtained from the above hydrolysis reaction may, optionally, further be subjected to a salt producing reaction to obtain the corresponding carboxylate. The salt producing reaction is performed by neutralization by an equal amount as the carboxylic acid of potassium hydroxide, sodium hydroxide, sodium carbonate, or other basic compound, or ammonia, trimethylamine, monoethanolamine, morpholine, etc. by an ordinary method.

Further, according to the present invention, there is provided a pharmaceutical composition comprised of an amount of a prostaglandins of the present invention or their salt effective for treatment and a pharmacologically allowable carrier. Note that the prostaglandins of the present invention may also be used formed as an inclusion compound of α, β, or γ-cyclodextrin etc.

When clinically applying the prostaglandins of the present invention or their salts or compounds containing the same for example as a medicine for the prevention or treatment of reconstriction after PTCA, the prostaglandins are used as active ingredients with a solid, liquid, or other pharmaceutically allowable carrier to form a pharmaceutical composition. Further, in accordance with need, it is preferable to add a diluent, that is, an excipient, stabilizer, or other additive to make the preparation. An injection use preparation of the prostaglandins of the present invention to be administered for therapeutical use must normally be in a sterile state. Sterility may be easily achieved by filtration through a pore size 0.2 μm membrane filter or other sterilizing filter membrane.

The ratio of the above-mentioned active ingredient in the carrier component in the pharmaceutical composition concerned may be changed between 1.0 to 90% w/w. The effective dosage for treatment depends on the method of administration, the age, the disease concerned, etc., but in general is 1 μg to 10 mg/day/person. For the individual means of administration, it is desirable to determine the efficiency of absorption into the body for each compound by pharmacologically known methods.

As the form of the medicines and means of administration, the medicines may be formed into granules, powders, dispersions, pills, tablets, capsules, liquids, or other forms and be administered orally or may be formed into suppositories, aerosols, or ointments and dermal patches and other local preparations etc. and administered nonorally. The injection may be administered intravenously, intraarterially, intramuscularly, or subcutaneously. Further, it may be made into an injection powder and prepared at the time of use.

A pharmaceutical use organic or inorganic solid or liquid carrier or diluent suited for oral, rectal, or nonoral administration may be used to prepare the prostaglandins of the present invention as pharmaceutical preparations. As the typical carriers or diluents capable of formulating in the tablets, capsules, etc., binders such as acacia, corn starch, or gelatin, excipients such as microcrystalline cellulose, decay agents such as corn starch, alginic acid, lubricants such as magnesium stearate, sweeteners such as sucrose, lactose, may be mentioned. In the case of capsules, in addition to the above substances, it is possible to add liquid carriers such as fatty acids. It is possible to use various types of other substances as coatings or as agents for improving the physical shape of the dosage units. The injection use sterile composition may be prepared in accordance with conventional pharmacological methods. For example, the active compounds are preferably dissolved or suspended in water or natural vegetable oils or other excipients or ethyl oleate and other synthetic fatty excipients. It is also possible to incorporate citrates, acetates, phosphates, and other buffers, ascorbic acid and other antioxidants in accordance with allowable pharmacological methods.

EXAMPLES

The present invention will be further verified below according to the Examples, but the present invention is of course not limited in scope by these Examples.

Example 1

Synthesis of methyl (11R,12R,13E,15S,17R)-9-trifluoromethanesulfonyloxy-11,15-bis(tert-butyldimethylsiloxy)-17,20-dimethylprosta-8,13-dienoate

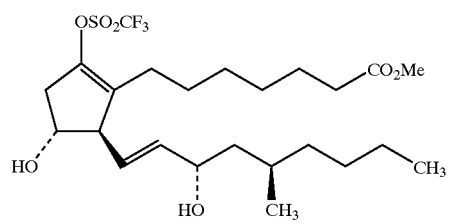

(1E,3S,5R)-1-iodo-3-(tert-butyldimethylsiloxy)-5-methyl-1-nonene (951 mg, 2.4 mmol) in ether (6 mL) was cooled to −78° C., then tert-butyllithium (1.54 mol/L, 3.12 mL, 4.8 mmol) was added. This was agitated at −78° C. for 2 hours. Further, to this were added 1-hexynylcopper (I) (347 mg, 2.4 mmol) and hexamethylphosphorus triamide (872 μl, 4.8 mmol) in ether (6 mL). This was agitated at −78° C. for a further 1 hour to give copper reagent. To the obtained copper reagent was drop-wise added (4R)-tert-butyldimethylsiloxy-2-(6-methoxycarbonylhexyl)-2-cyclopenten-1-one (709 mg, 2.0 mmol) in tetrahydrofuran (40 mL). The reaction mixture was agitated at −78° C. for 15 minutes, then the reaction temperature was raised and it was agitated at −50 to −30° C. for 1 hour to object a conjugate adduct. To the resultant conjugate adduct was added at −30° C. N-phenyltrifluoromethane-sulfonimide (1.07 mg, 3.0 mmol) in tetrahydrofuran (6 mL). This was agitated for 15 hours while raising the reaction temperature to room temperature. The reaction solution was poured into saturated ammonium sulfate (100 mL) to end the reaction. The mixture was separated, then the aqueous layer was extracted with ether and the extract was combined with the organic layer, then dried over anhydrous magnesium sulfate. The solution was concentrated under reduced pressure, then was purified by silica gel column chromotography (2 to 5% ethyl acetate/hexane) to obtain methyl (11R,12R,13E,15S,17R)-9-trifluoromethanesulfonyloxy-11,15-bis (tert-butyldimethylsiloxy)-17,20-dimethylprosta-8,13-dienoate (627 mg, 41%).

$^1$H-NMR (270 MHz, δppm, CDCl$_3$): 0.00, 0.01, 0.05 (s, 12H), 0.8–0.9 (m, 6H), 0.87 (s, 9H), 0.89 (s, 9H), 1.0–1.7 (m, 17H), 2.1–2.3 (m, 2H), 2.30 (t, J=7.6 Hz, 2H), 2.46 (d, J=15.8 Hz, 1H), 2.91 (dd, J=6.9 & 16.2 Hz, 1H), 3.04 (d, J=8.9 Hz, 1H), 3.67 (s, 3H), 4.0–4.2 (m, 2H), 5.32 (dd, J=9.2 & 15.5 Hz, 1H), 5.56 (dd, J=5.9 & 15.5 Hz, 1H), Example 2

Synthesis of methyl (11R,12R,13E,15S,17R)-9-trifluoromethanesulfonyloxy-11,15-dihydroxy-17,20-dimethylprosta-8,13-dienoate

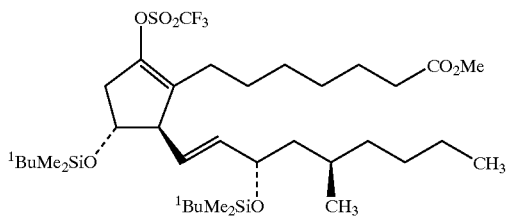

As a byproduct of the reaction of Example 6, methyl (11R,12R,13E,15S,17R)-9-trifluoromethanesulfonyloxy-11,15-dihydroxy-17,20-dimethylprosta-8,13-dienoate (48 mg) is obtained. See Example 6.

$^1$H-NMR (270 MHz, δppm, CDCl$_3$): 0.8–1.0 (m, 6H), 1.1–2.0 (m, 17H), 2.1–2.4 (m, 2H), 2.30 (t, J=7.4 Hz, 2H), 2.56 (dd, J=4.5 & 16.0 Hz, 1H), 2.95 (dd, J=7.3 & 15.8 Hz, 1H), 3.10 (dd, J=3.6 & 8.9 Hz, 1H), 3.67 (s, 3H), 4.1–4.3 (m, 2H), 5.45 (dd, J=8.9 & 15.2 Hz, 1H), 5.63 (dd, J=6.6 & 15.2 Hz, 1H)

Example 3

Synthesis of methyl (11R,12S,13E,15S,17R)-9-trifluoromethanesulfonyloxy-11,15-bis(tert-butyldimethylsiloxy)-17,20-dimethyl-7-thiaprosta-8,13-dienoate

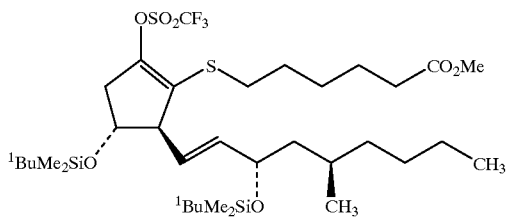

(1E,3S,5R)-1-iodo-3-(tert-butyldimethylsiloxy)-5-methyl-1-nonene (476 mg, 1.2 mmol) in ether (3 mL) was cooled to −78° C., then tert-butyllithium (1.54 mol/L, 1.56 mL, 2.4 mmol) was added. This was agitated at −78° C. for 2 hours. Further, to this were added 1-hexynylcopper (I) (174 mg, 1.2 mmol) and hexamethylphosphorus triamide (436 μl, 2.4 mmol) in ether (6 mL). This was agitated at −78° C. for a further 1 hour to give copper reagent. To the copper reagent thus obtained was drop-wise added (4R)-tert-butyldimethylsiloxy-2-(5-methoxycarbonylpentylthio)-2-cyclopenten-1-one (373 mg, 1.0 mmol) in tetrahydrofuran (20 mL). The reaction mixture was agitated at −78° C. for 15 minutes, then the reaction temperature was raised and it was agitated at −50 to −30° C. for 1 hour to obtain a conjugate adduct. To the obtained conjugate adduct was added at −30° C. N-phenyltrifluoromethanesulfonimide (429 mg, 1.2 mmol) in tetrahydrofuran (5 mL). This was agitated for 15 hours while raising the reaction temperature to room temperature. The reaction solution was poured into saturated ammonium sulfate (65 mL) to end the reaction. The mixture was separated, then the aqueous layer was extracted with ether. The extract was combined with the organic layer, then dried over anhydrous magnesium sulfate. The solution was concentrated under reduced pressure, then was purified by silica gel column chromatography (2 to 5% ethyl acetate/hexane) to obtain methyl (11R,12S,13E,15S,17R)-9-trifluoromethanesulfonyloxy-11,15-bis(tert-butyldimethylsiloxy)-17,20-dimethyl-7-thiaprosta-8,13-dienoate (410 mg, 52%).

$^1$H-NMR (270 MHz, δppm, CDCl$_3$): 0.03, 0.05, 0.06 (s, 12H), 0.8–0.9 (m, 6H), 0.88 (s, 9H), 0.89 (s, 9H), 1.0–1.7 (m, 15H), 2.31 (t, J=7.4 Hz, 2H), 2.4–2.9 (m, 3H), 2.97 (dd, J=6.3 & 16.2 Hz, 1H), 3.16 (d, J=7.9 Hz, 1H), 3.67 (s, 3H), 4.0–4.2 (m, 2H), 5.41 (dd, J=8.4 & 15.3 Hz, 1H), 5.64 (dd, J=5.4 & 15.7 Hz, 1H)

Example 4

Synthesis of methyl (11R,12S,13E,15S)-9-trifluoromethanesulfonyloxy-11,15-bis(tert-butyldimethylsiloxy)-16-phenyl-17,18,19,20-tetranol-7-thiaprosta-8,13-dienoate

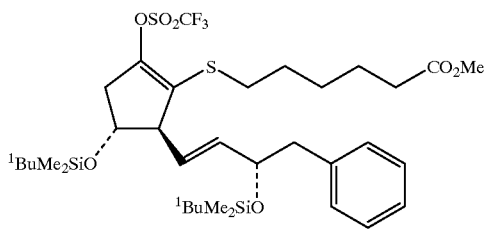

(1E,3S)-1-iodo-3-(tert-butyldimethylsiloxy)-4-phenyl-1-butene (699 mg) in ether (4 mL) was cooled to −78° C., then tert-butyllithium (1.50 mol/L, 2.40 mL) was added. This was agitated at −78° C. for 1 hour. Further, to this were added 1-hexynylcopper (I) (260 mg) and hexamethylphosphorus triamide (654 μl) in ether (10 mL). This was agitated at −78° C. for a further 1 hour to give copper reagent. To the resultant copper reagent was drop-wise added (4R)-tert-butyldimethylsiloxy-2-(5-methoxycarbonylpentylthio)-2-cyclopenten-1-one (560 mg) in tetrahydrofuran (20 mL). The reaction mixture was agitated at −78° C. for 1 hour, then the reaction temperature was raised and it was agitated at −50 to −40° C. for 30 minutes to obtain a conjugate adduct. To the obtained conjugate adduct was added at −40° C. N-phenyltrifluoromethanesulfonimide (1.47 mg) in tetrahydrofuran (13 mL). The solution was agitated for 1 hour, while raising the reaction temperature to room temperature. The reaction solution was poured into saturated ammonium sulfate (100 mL) to end the reaction. The mixture was separated, then the aqueous layer was extracted with ether and the extract was combined with the organic layer, then dried over anhydrous magnesium sulfate. The solution was concentrated under reduced pressure, then was purified by silica gel column chromatography (3 to 4% ethyl acetate/hexane) to obtain methyl (11R,12S,13E,15S)-9-trifluoromethanesulfonyloxy-11,15-bis(tert-butyldimethylsiloxy)-16-phenyl-17,18,19,20-tetranol-7-thiaprosta-8,13-dienoate (983 mg, 86%).

$^1$H-NMR (270M Hz, δppm, CDCl$_3$): −0.25 (s, 3H), −0.09 (s, 3H), 0.04 (s, 3H), 0.06 (s, 3H), 0.85 (s, 9H), 0.87 (s, 9H), 1.3–1.7 (m, 6H), 2.31 (t, J=7.3 Hz, 3H), 2.4–2.6 (m, 2H), 2.65–2.8 (m, 3H), 2.93 (ddd, J=1.6 & 6.2 & 14.9 Hz, 1H), 3.14 (d, J=8.9 Hz, 1H), 3.66 (s, 3H), 4.0–4.03 (m, 1H), 5.28 (dd, J=4.9 & 11.6 Hz, 1H), 5.43 (ddd, J=1.0 & 8.2 & 15.5 Hz, 1H), 5.67 (dd, J=5.3 & 15.5 Hz, 1H), 7.1–7.3 (m, 5H)

Example 5

Synthesis of methyl (11R,12R,13E,15S,17R)-9-methyl-11,15-bis(tert-butyldimethylsiloxy)-17,20-dimethylprosta-8,13-dienoate

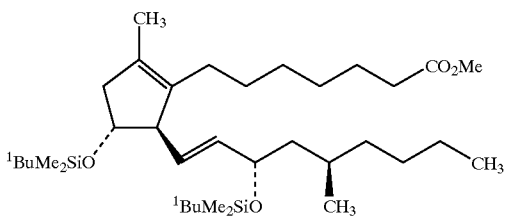

To tetrakistriphenylphosphinepalladium prepared in advance in the system from tris(dibenzylideneacetone)dipalladium(0) (46 mg, 0.05 mmol) and triphenylphosphine (105 mg, 0.4 mmol) were added methyl(11R,12R,13E,15S,17R)-9-trifluoromethane-sulfonyloxy-11,15-bis(tert-butyldimethylsiloxy)-17,20-dimethylprosta-8,13-dienoate (379 mg, 0.5 mmol) in a 1,2-dichloroethane (5 mL) solution and 2M trimethylaluminum in hexane (0.375 mL, 0.75 mmol). This was agitated for 3 hours at room temperature. Ether was added to dilute the reaction solution, then the solution was poured in 1N hydrochloric acid. The desired product was extracted with ether from the mixture. The extract was washed with brine, then was dried over anhydrous sodium sulfate. The solution was concentrated under reduced pressure, then was purified by silica gel column chromatography (2% ethyl acetate/hexane) to obtain methyl (11R,12R,13E,15S,17R)-9-methyl-11,15-bis(tert-butyldimethylsiloxy)-17,20-dimethylprosta-8,13-dienoic acid as a mixture with the unreacted methyl(11R,12R,13E,15S,17R)-9-trifluoromethanesulfonyloxy-11,15-bis(tert-butyldimethylsiloxy)-17,20-dimethylprosta-8,13-dienoic acid etc. (174 mg). The NMR data for the mixture was measured, but could not be analyzed. This mixture was subjected to the operation of Example 6 without further purification.

Example 6

Synthesis of methyl (11R,12R,13E,15S,17R)-9-methyl-11,15-dihydroxy-17,20-dimethylprosta-8,13-dienoate

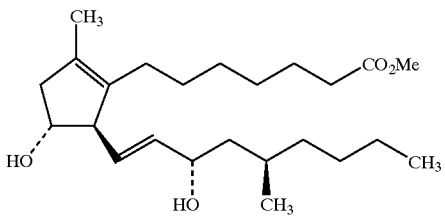

To a solution of ice-cooled acetonitrile (2 ml) and pyridine (0.2 mL) was added hydrogen fluoride-pyridine (0.2 mL). To this solution was added a mixture (174 mg) containing methyl (11R,12R,13E,15S,17R)-9-methyl-11,15-bis(tert-butyldimethylsiloxy)-17,20-dimethylprosta-8,13-dienoate in pyridine (0.2 mL). The ice bath was removed and the solution was agitated for 15 hours while returning it to room temperature. The reaction solution was poured into a mixture of ethyl acetate and a saturated aqueous solution of sodium hydrogencarbonate. The desired product was extracted from this mixed solution with ethyl acetate. The extract was washed with brine, then dried over anhydrous sodium sulfate. The solution was concentrated under reduced pressure, then was purified by silica gel column chromatography (30 to 50% ethyl acetate/hexane) and subjected to thin layer chromatography for separation (ethyl acetate:hexane=4:1) to obtain methyl (11R,12R,13E,15S,17R)-9-methyl-11,15-dihydroxy-17,20-dimethylprosta-8,13-dienoate (21 mg, 2 step 10%) and as a byproduct, methyl (11R,12R,13E,15S,17R)-9-trifluoromethanesulfonyloxy-11,15-dihydroxy-17,20-dimethylprosta-8,13-dienoate (48 mg, 2 step, 18%).

$^1$H NMR (270M Hz, δppm, CDCl$_3$): 0.8–1.0 (m, 6H), 1.1–1.9 (m, 17H), 1.64 (d, J=0.7 Hz, 3H), 2.0–2.4 (m, 3H), 2.30 (t, J=7.4 Hz, 2H), 2.62 (dd, J=6.6 & 16.2 Hz, 1H), 3.04 (d, J=7.3 Hz, 1H), 3.66 (s, 3H), 4.0–4.2 (m, 1H), 4.1–4.3 (m, 1H), 5.40 (dd, J=8.9 & 15.5 Hz, 1H), 5.54 (dd, J=6.8 & 15.3 Hz, 1H)

$^{13}$C-NMR (67.5 MHz, δppm, CDCl$_3$): 14.0, 14.1, 19.6, 22.9, 25.9, 26.3, 27.5, 28.9, 29.0, 29.1, 29.2, 34.0, 36.9, 44.9, 45.7, 51.4, 60.3, 70.8, 67.7, 129.9, 131.5, 135.0, 135.2, 174.3

Example 7

Synthesis of methyl (11R,12S,13E,15S,17R)-9-methyl-11,15-bis(tert-butyldimethylsiloxy)-17,20-dimethyl-7-thiaprosta-8,13-dienoate

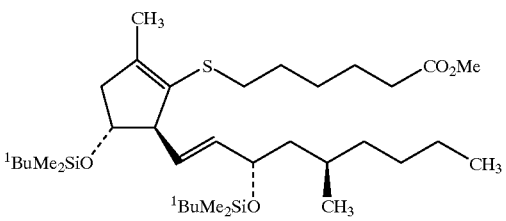

To tetrakistriphenylphosphinepalladium prepared in advance in the system from tris(dibenzylideneacetone)dipalladium(0) (92 mg, 0.1 mmol) and triphenylphosphine (210 mg, 0.8 mmol) were added methyl (11R,12S,13E,15S,17R)-9-trifluoromethanesulfonyloxy-11,15-bis(tert-butyldimethylsiloxy)-17,20-dimethyl-7-thiaprosta-8,13-dienoate 437 mg, 0.546 mmol) in 1,2-dichloroethane (5 mL) and 2M trimethylaluminum in hexane (0.423 mL, 0.846 mmol). This was agitated for 3 hours at room temperature. Ether was added to dilute the reaction solution, then the solution was poured in 1N hydrochloric acid. The desired product was extracted with ether from the mixture. The extract was washed with brine, then was dried over anhydrous sodium sulfate. The solution was concentrated under reduced pressure, then was purified by silica gel column chromatography (2% ethyl acetate/hexane) to obtain methyl (11R,12S,13E,15S,17R)-9-methyl-11,15-bis(tert-butyldimethylsiloxy)-17,20-dimethyl-7-thiaprosta-8,13-dienoate (193 mg, 54%).

$^1$H-NMR (270 MHz, δppm, CDCl$_3$): 0.03, 0.05 (s, 12H), 0.8–0.9 (m, 6H), 0.87 (s, 9H), 0.88 (s, 9H), 1.0–1.7 (m, 15H), 1.79 (s, 3H), 2.1–2.7 (m, 5H), 3.12 (d, J=7.9 Hz, 1H), 3.66 (s, 3H), 4.0–4.2 (m, 2H), 5.34 (dd, J=8.9 & 15.5 Hz, 1H), 5.52 (dd, J=6.3 & 15.5 Hz, 1H)

Example 8

Synthesis of methyl (11R,12S,13E,15S,17R)-9-methyl-11,15-dihydroxy-17,20-dimethyl-7-thiaprosta-8,13-dienoate

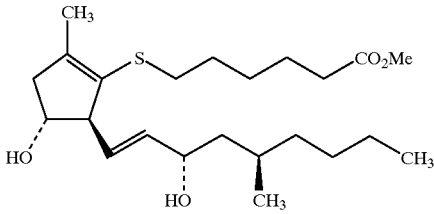

To a solution of ice-cooled acetonitrile (2 mL) and pyridine (0.2 mL) was added hydrogen fluoride-pyridine (0.2 mL). To this solution was added methyl(11R,12S,13E,15S,17R)-9-methyl-11,15-bis(tert-butyldimethylsiloxy)-17,20-dimethyl-7-thiaprosta-8,13-diene acid (196 mg, 0.306 mmol) in pyridine (0.2 mL). The ice bath was removed and the solution was agitated for 15 hours, while returning it to room temperature. The reaction solution was poured into a mixture of ethyl acetate and saturated aqueous sodium hydrogencarbonate. The desired product was extracted from this mixed solution with ethyl acetate. The extract was washed with brine, then dried over anhydrous sodium sulfate. The solution was concentrated under reduced pressure, then was purified by silica gel chromatography (30 to 50% ethyl acetate/hexane) to obtain methyl (11R,12S,13E,15S,17R)-9-methyl-11,15-dihydroxy-17,20-dimethyl-7-thiaprosta-8,13-dienoate (78 mg, 62%).

¹H-NMR (270 MHz, δppm, CDCl₃): 0.8–0.9 (m, 6H), 1.1–1.7 (m, 15H), 1.82 (d, J=1.3 Hz, 3H), 2.3–2.8 (m, 4H), 2.31 (t, J=7.4 Hz, 2H), 3.1–3.3 (m, 1H), 3.67 (s, 3H), 4.0–4.2 (m, 1H), 4.1–4.3 (m, 1H, 5.50 (dd, J=7.9 & 15.2 Hz, 1H), 5.61 (dd, J=6.3 & 15.5 Hz, 1H)

Example 9

Synthesis of (11R,12S,13E,15S,17R)-9-methyl-11,15-dihydroxy-17,20-dimethyl-7-thiaprosta-8,13-dienoic acid

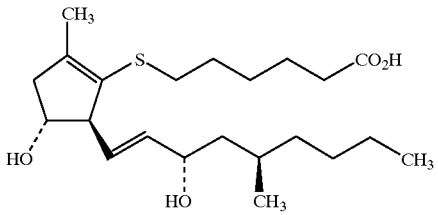

To methyl (11R,12S,13E,15S,17R)-9-methyl-11,15-dihydroxy-17,20-dimethyl-7-thiaprosta-8,13-dienoate (41 mg, 0.099 mmol) in acetone (1 mL) was added pH 8 phosphate buffer (10 mL). To this was further added esterase containing solution (derived from pig's liver, made by Sigma Co., 100 μl). This was agitated at room temperature for 15 hours. To the reaction solution was added dilute hydrochloric acid to make the solution pH 4. Further, the solution was made saturated by ammonium sulfate, then the desired product was extracted with ethyl acetate. The extract was washed with brine, then was dried over anhydrous sodium sulfate. The solution was concentrated under reduced pressure, then subjected to thin layer chromotography for separation (development solution: ethyl acetate) to obtain (11R,12S,13E,15S,17R)-9-methyl-11,15-dihydroxy-17,20-dimethyl-7-thiaprosta-8,13-dienoic acid (5.4 mg, 14%).

¹H-NMR (270 MHz, δppm, CDCl₃): 0.8–1.0 (m, 6H), 1.1–1.7 (m, 15H), 1.82 (s, 3H), 2.2–2.8 (m, 4H), 3.1–3.2 (m, 1H), 4.1–4.3 (m, 2H), 5.50 (dd, J=8.3 & 15.5 Hz, 1H), 5.62 (dd, J=6.4 & 15.3 Hz, 1H)

Example 10

Synthesis of methyl (11R,12S,13E,15S,17R)-9-pentyl-11,15-bis(tert-butyldimethylsiloxy)-17,20-dimethyl-7thiaprosta-8,13-dienoate

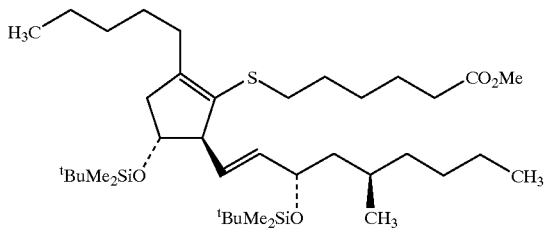

1-pentene (110 μl, 1.0 mmol) in tetrahydrofuran (3 mL) was ice-cooled, then 9-borabicyclo[3,3,1]nonane (9-BBN, 0.5M THF solution, 2.0 mL, 1.05 mmoL) was added. This was agitated for 6 hours while gradually raising the reaction temperature to room temperature. Further, to this were added methyl (11R,12S,13E,15S,17R)-9-trifluoromethanesulfonyloxy-11,15-bis(tert-butyldimethylsiloxy)-17,20-dimethyl-7-thiaprosta-8,13-dienoic acid (205 mg, 0.264 mmol), bistriphenylphosphinepalladiumchloride (140 mg, 0.2 mmol), and tripotassium phosphate (255 mg, 1.2 mmol) in tetrahydrofuran (5 mL) suspension. The reaction mixture was agitated at 60° C. for 15 hours. The reaction solution was cooled, then subjected to Florisil column chromotography to remove the metal complexes. The resultant solution was concentrated under reduced pressure, then was purified by silica gel column chromotography (2 to 4% ethyl acetate/hexane) to obtain methyl (11R,12S,13E,15S,17R)-9-pentyl-11,15-bis(tert-butyldimethylsiloxy)-17,20-dimethyl-7-thiaprosta-8,13-dienoate (71 mg, 38%).

¹H-NMR (270 MHz, δppm, CDCl₃): 0.03, 0.05 (s, 12H), 0.8–0.9 (m, 9H), 0.87 (s, 9H), 0.88 (s, 9H), 0.9–1.7 (m, 21H), 2.1–2.7 (m, 3H), 3.14 (d, J=8.3 Hz, 1H), 3.66 (s, 3H), 4.0–4.2 (m, 2H), 5.34 (dd, J=8.6 & 15.5 Hz, 1H), 5.52 (dd, J=6.3 & 15.2 Hz, 1H)

Example 11

Synthesis of methyl (11R,12S,13E,15S,17R)-9-pentyl-11,15-bis(tert-butyldimethylsiloxy)-17,20-dimethyl-7-thiaprosta-8,13-dienoate

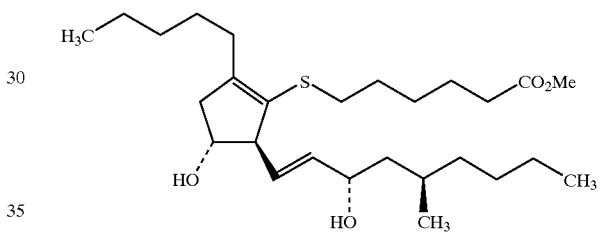

To a solution of ice-cooled acetonitrile (1 mL) and pyridine (0.1 mL) was added hydrogen fluoride-pyridine (0.1 mL). To this solution was added methyl (11R,12S,13E,15S,17R)-9-pentyl-11,15-bis(tert-butyldimethylsiloxy)-17,20-dimethyl-7-thiaprosta-8,13-dienoate (71 mg, 0.10 mmol) in pyridine (0.1 mL). The ice bath was removed and the solution was agitated for 15 hours while returning it to room temperature. The reaction solution was poured into a mixture of ethyl acetate and saturated aqueous sodium hydrogencarbonate. The desired product was extracted from this mixed solution with ethyl acetate. The extract was washed with brine, then dried over anhydrous sodium sulfate. The solution was concentrated under reduced pressure, then was purified by silica gel column chromatography (30 to 50% ethyl acetate/hexane) to obtain methyl (11R,12S,13E,15S, 17R)-9-pentyl-11,15-dihydroxy-17,20-dimethyl-7-thiaprosta-8,13-dienoate (24 mg, 50%).

¹H-NMR (270 MHz, δppm, CDCl₃): 0.8–1.0 (m, 9H), 1.1–1.7 (m, 21H), 2.26 (t, J=7.3 Hz, 2H), 2.3–2.8 (m, 4H), 2.31 (t, J=7.3 Hz, 2H), 3.22 (dd, J=3.1 & 7.8 Hz, 1H), 3.67 (s, 3H), 4.0–4.2 (m, 1H), 4.20 (dt, J=8.2 & 5.6 Hz, 1H), 5.51 (dd, J=7.8 & 15.3 Hz, 1H), 5.62 (dd, J=6.3 & 15.2 Hz, 1H)

¹³C-NMR (67.5 MHz, δppm, CDCl₃): 14.0, 14.1, 19.5, 22.5, 22.9, 24.5, 27.4, 28.0, 29.1, 29.1, 29.5, 29.6, 31.1, 31.6, 33.9, 37.0, 43.1, 44.8, 51.5, 60.1, 70.6, 76.4, 127.8, 130.4, 135.6, 144.2, 174.1

Example 12

Synthesis of (11R,12S,13E,15S,17R)-9-pentyl-11,15-dihydroxy-17,20-dimethyl-7-thiaprosta-8,13-dienoic acid

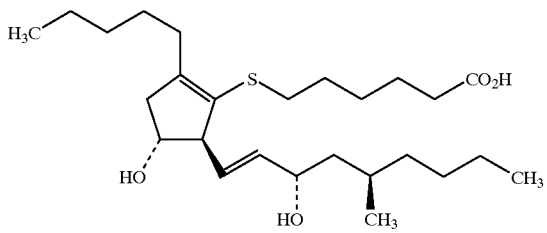

To methyl (11R,12S,13E,15S,17R)-9-pentyl-11,15-dihydroxy-17,20-dimethyl-7-thiaprosta-8,13-dienoate (20 mg, 0.042 mmol) in acetone (1 mL) was added pH 8 phosphate buffer (5 mL). To this was further added esterase containing solution (derived from pig's liver, made by Sigma Co., 50 μl). The solution was agitated at room temperature for 24 hours. Dilute hydrochloric acid was added to the reaction solution to make the solution pH 4. Further, the solution was made saturated by ammonium sulfate, then the desired product was extracted with ethyl acetate. The extract was washed with brine, then was dried over anhydrous sodium sulfate. The solution was concentrated under reduced pressure, then subjected to thin layer chromatography for separation (development solution: ethyl acetate) to obtain (11R,12S,13E,15S,17R)-9-pentyl-11,15-dihydroxy-17,20-dimethyl-7-thiaprosta-8,13-dienoic acid (5.4 mg, 14%).

$^1$H-NMR (270 MHz, δppm, CDCl$_3$): 0.8–1.0 (m, 9H), 1.1–1.7 (m, 21H), 2.26 (t, J=7.1 Hz, 2H), 2.3–2.8 (m, 4H), 2.34 (t, J=7.1 Hz, 2H), 3.23 (d, J=5.0 Hz, 1H), 4.1–4.3 (m, 2H), 5.51 (dd, J=7.9 & 15.2 Hz, 1H), 5.62 (dd, J=6.4 & 15.3 Hz, 1H)

Example 13

Synthesis of methyl (11R,12S,13E,15S,17R)-9-(3,3-dimethylbutyl)-11,15-bis(tert-butyldimethylsiloxy)-17,20-dimethyl-7-thiaprosta-8,13-dienoate

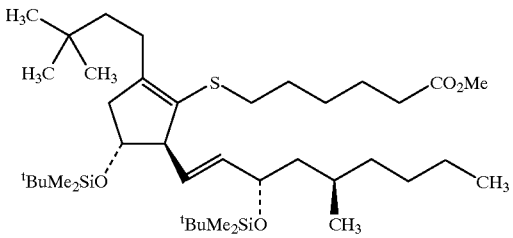

3,3-dimethyl-1-butene (129 μl, 1.0 mmol) in tetrahydrofuran (3 mL) was ice-cooled, then 9-BBN (0.5M THF solution, 2.1 mL, 1.05 mmol) was added and the solution was agitated for 6 hours, while raising the reaction temperature gradually to room temperature. Further, to this were added methyl (11R,12S,13E,15S,17R)-9-trifluoromethanesulfonyloxy-11,15-bis(tert-butyldimethylsiloxy)-17,20-dimethyl-7-thiaprosta-8,13-dieonate (233 mg, 0.3 mmol), bistriphenylphosphinepalladiumchloride (70 mg, 0.1 mmol), and tripotassium phosphate (255 mg, 1.2 mmol) in tetrahydrofuran (5 mL) suspension. The reaction mixture was agitated at 60° C. for 15 hours. The reaction solution was cooled, then subjected to Florisil column chromatography to remove the metal complexes. The resultant solution was concentrated under reduced pressure, then was purified by silica gel column chromotography (2 to 4% ethyl acetate/hexane) to obtain methyl (11R,12S,13E,15S,17R)-9-(3,3-dimethylbutyl-11,15-bis(tert-butyldimethylsiloxy)-17,20-dimethyl-7-thiaprosta-8,13-dienoate (137 mg, 64%).

$^1$H-NMR (270 MHz, δppm, CDCl$_3$): 0.03 (s), 0.05 (s) . . . 12H, 0.8–0.9 (m, 33H), 1.0–1.7 (m, 17H), 2.1–2.7 (m, 8H), 3.13 (d, J=7.6 Hz, 1H), 3.66 (s, 3H), 4.0–4.2 (m, 2H), 5.33 (dd, J=8.6 & 15.2 Hz, 1H), 5.52 (dd, J=6.2 & 15.7 Hz, 1H)

Example 14

Synthesis of methyl (11R,12S,13E,15S,17R)-9-(3,3-dimethylbutyl)-11,15-bis(tert-butyldimethylsiloxy)-17,20-dimethyl-7-thiaprosta-8,13-dienoate

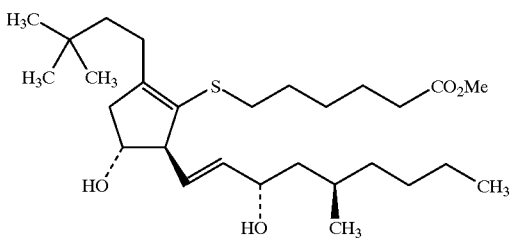

To a solution of ice-cooled acetonitrile (1.5 mL) and pyridine (0.15 mL) was added hydrogen fluoride-pyridine (0.15 mL). To this solution was added methyl (11R,12S,13E,15S,17R)-9-(3,3-dimethylbutyl-11,15-bis(tert-butyldimethylsiloxy)-17,20-dimethyl-7-thiaprosta-8,13-dienoate (137 mg, 0.192 mmol) in pyridine (0.15 mL). The ice bath was removed and the solution was agitated for 15 hours, while returning it to room temperature. The reaction solution was poured into a mixture of ethyl acetate and saturated aqueous sodium hydrogencarbonate. The desired product was extracted from this mixed solution with ethyl acetate. The extract was washed with brine, then dried over anhydrous sodium sulfate. The solution was concentrated under reduced pressure, then was purified by silica gel column chromatography (40 to 50% ethyl acetate/hexane) to obtain methyl (11R,12S,13E,15S,17R)-9-dimethylbutyl-11,15-bis(tert-butyldimethylsiloxy)-17,20-dimethyl-7-thiaprosta-8,13-dienoate (61 mg, 66%).

$^1$H-NMR (270 MHz, δppm, CDCl$_3$): 0.8–0.9 (m, 15H), 1.1–1.7 (m, 17H), 2.1–2.8 (m, 8H), 3.21 (dd, J=3.3 & 7.9 Hz, 1H), 3.67 (s, 3H), 4.0–4.2 (m, 1H), 4.1–4.3 (m, 1H), 5.51 (dd, J=7.9 & 15.5 Hz, 1H), 5.61 (dd, J=6.3 & 15.2 Hz, 1H)

Example 15

Synthesis of methyl (11R,12S,13E,15S,17R)-9-cyano-11,15-bis(tert-butyldimethylsiloxy)-17,20-dimethyl-7-thiaprosta-8,13-dienoate

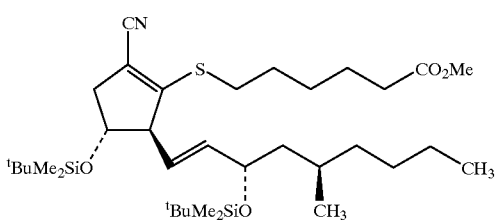

Tetrakis(triphenylphosphine)palladium was prepared in advance in the system from tris(dibenzylideneacetone)dipalladium(0) (45.8 mg, 0.05 mmol) and triphenylphosphine (105 mg, 0.4 mmol). To this were added methyl (11R,12S,13E,15S,17R)-9-trifuloromethanesulfonyloxy-11,15-bis(tert-butyldimethylsiloxy)-17,20-dimethyl-7-thiaprosta-8,13-dienoate (388 mg, 0.5 mmol) and sodium cyanide (36.8 mg, 0.75 mmol) in tetrahydrofuran (20 mL) suspension. This was refluxed for 15 hours. The reaction solution was cooled to room temperature, ether was added to dilute it, then the solution was washed with brine. The ether solution was dried over anhydrous sodium sulfate, then was concentrated under reduced pressure, then was purified by silica gel column chromatography (5% ethyl acetate/hexane) to obtain methyl (11R,12S,13E,15S,17R)-9-cyano-11,15-bis(tert-butyldimethylsiloxy)-17,20-dimethyl-7-thiaprosta-8,13-dienoate (170 mg, 52%).

$^1$H-NMR (270 MHz, δppm, CDCl$_3$): 0.02, 0.05, 0.05 (s, 12H), 0.8–0.9 (m, 6H), 0.87 (s, 9H), 0.89 (s, 9H), 1.0–1.7 (m, 15H), 2.32 (t, J=7.4 Hz, 2H), 2.49 (dd, J=2.1 & 15.7 Hz, 1H), 2.8–3.2 (m, 3H), 3.24 (dd, J=2.1 & 8.4 Hz, 1H), 3.67 (s, 3H), 4.0–4.2 (m, 2H), 5.34 (ddd, J=1.0 & 8.4 & 15.3 Hz, 1H), 5.61 (dd, J=5.6 & 15.5 Hz, 1H)

Example 16

Synthesis of methyl (11R,12S,13E,15S,17R)-9-cyano-11,15-dihydroxy-17,20-dimethyl-7-thiaprosta-8,13-dieonate

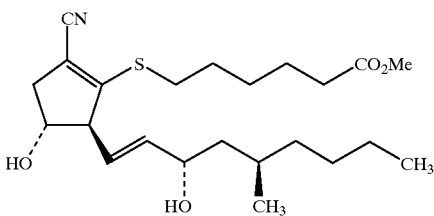

To a solution of ice-cooled acetonitrile (2 mL) and pyridine (0.2 mL) was added hydrogen fluoride-pyridine (0.2 mL). To this solution was added methyl (11R,12S,13E,15S,17R)-9-cyano-11,15-bis(tert-butyldimethylsiloxy)-17,20-dimethyl-7-thiaprosta-8,13-dienoate (170 mg, 0.261 mmol) in pyridine (0.2 mL). The ice bath was removed and the solution was agitated for 15 hours while returning it to room temperature. The reaction solution was poured into a mixture of ethyl acetate and saturated aqueous sodium hydrogencarbonate. The desired product was extracted from this mixed solution with ethyl acetate. The extract was washed with brine, then dried over anhydrous sodium sulfate. The solution was concentrated under reduced pressure, then was purified by silica gel column chromatography (40 to 50% ethyl acetate/hexane) to obtain methyl (11R,12S,13E,15S,17R)-9-cyano-11,15-dihydroxy-17,20-dimethyl-7-thiaprosta-8,13-dienoate 96 mg, 87%).

$^1$H-NMR (270 MHz, δppm, CDCl$_3$): 0.8–1.0 (m,6H), 1.00 (t, J=7.4 Hz, 3H), 1.1–1.8 (m, 15H), 2.32 (t, J=7.4 Hz, 2H), 2.56 (ddd, J=1.0 & 4.3 & 15.5 Hz, 1H), 2.91 (dd, J=6.3 & 15.5 Hz, 1H), 3.0–3.2 (m, 2H), 3.29 (dd, J=4.0 & 8.6 Hz, 1H), 3.67 (s, 3H), 4.1–4.3 (m, 2H), 5.45 (dd, J=8.6 & 15.5 Hz, 1H), 5.65 (dd, J=6.6 & 15.5 Hz, 1H), $^{13}$C-NMR (67.5 MHz, δppm, CDCl$_3$): 14.1, 19.4, 22.9, 24.2, 27.6, 29.0, 29.0, 29.2, 30.9, 33.7, 36.8, 42.4, 44.6, 51.6, 61.3, 70.3, 75.9, 101.4, 116.7, 126.8, 137.9, 157.5, 174.1

IR (neat) 3775/W3431/S2926/S2858/S2731/W2363/W2208/S1738/S1568/ S1456/S1437/S1377/S1261/S1203/S1176/S1049/S970/S862/M729/M

Example 17

Synthesis of methyl (11R,12S,13E,15S,17R)-9-trifluoromethyl-11,15-bis(tert-butyldimethylsiloxy)-17,20-dimethyl-7-thiaprosta-8,13-dienoate

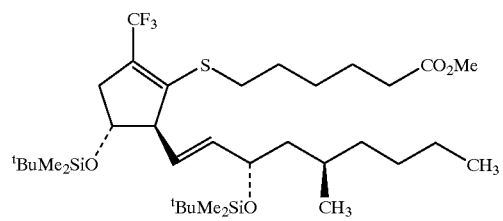

Tris(dibenzylideneacetone)dipalladium(0) (11.4 mg, 0.0125 mmol), triphenylphosphine (13.1 mg, 0.05 mmol), zinc (powder) (36.8 mg, 56.3 mmol), and methyl (11R,12S,13E,15S,17R)-9-trifluoromethanesulfonyloxy-11,15-bis(tert-butyldimethylsiloxy)-17,20-dimethyl-7-thiaprosta-8,13-dienoate (218 mg, 0.282 mmol) in tetrahydrofuran (5 mL) were placed in an autoclave reactor, a small sized container of trifluoromethyl iodide was connected, and the inside of the reaction vessel was made the same pressure as the inside of the small sized container. The reaction vessel was made to vibrate in trifluoromethyl iodide atmosphere for 1 hour by an ultrasonic wave washer. Next, the unreacted trifluoromethyl iodide in the reaction vessel was removed to obtain the reaction solution which was passed through Florisil column. The solution thus obtained was concentrated under reduced pressure, then was purified by silica gel column chromatography (4to 10% ethyl acetate/hexane) to obtain methyl (11R,12S,13E,15S,17R)-9-trifluoromethyl-11,15-bis(tert-butyldimethylsiloxy)-17,20-dimethyl-7-thiaprosta-8,13-dienoate (72 mg, 36%).

$^1$H-NMR (270 M Hz, δppm, CDCl$_3$): 0.06 (s, 6H), 0.8–1.0 (m, 6H), 0.88 (s, 18H), 1.0–1.7 (m, 15H), 2.31 (t, J=7.1 Hz, 2H), 2.4–2.8 (m, 3H), 2.8–3.0 (m, 1H), 3.1–3.3 (m, 1H), 3.67 (s, 3H), 4.0–4.3 (m, 2H), 5.4–5.8 (m, 2H),

Example 18

Synthesis of methyl (11R,12S,13E,15S,17R)-9-trifluoromethyl-11,15-dihydroxy-17,20-dimethyl-7-thiaprosta-8,13-dienoate

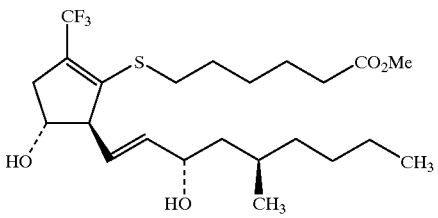

To a solution of ice-cooled acetonitrile (1 mL) and pyridine (0.1 mL) was added hydrogen fluoride-pyridine (0.1 mL). To this solution was added methyl (11R,12S,13E,15S, 17R)-9-trifluoromethyl-11,15-bis(tert-butyldimethylsiloxy)-17,20-dimethyl-7-thiaprosta-8,13-dienoate (36 mg, 0.052 mmol) in pyridine (0.1 mL). The ice bath was removed and the solution was agitated for 15 hours while returning it to room temperature. The reaction solution was poured into a mixture of ethyl acetate and saturated aqueous sodium hydrogencarbonate. The desired product was extracted from this mixed solution with ethyl acetate. The extract was washed with brine, then dried over anhydrous sodium sulfate. The solution was concentrated under reduced pressure, then was subjected to thin layer chromotography (ethyl acetate/hexane=4/1) to obtain methyl (11R, 12S,13E,15S,17R)-9-trifluoromethyl-11,12-dihydroxy-17, 20-dimethyl-7-thiaprosta-8,13-dienoate (12 mg, 48%).
$^1$H-NMR (270 MHz, δppm, CDCl$_3$): 0.8–1.0 (m, 6H), 1.1–1.8 (m, 15H), 2.32 (t, J=7.3 Hz, 2H), 2.5–2.9 (m, 3H), 3.03 (ddd, J=1.7 & 6.6 & 16.5 Hz, 1H), 3.27 (br.d, J=6.3 Hz, 1H), 3.67 (s, 3H), 4.1–4.3 (m, 2H), 5.56 (dd, J=8.3 & 15.5 Hz, 1H), 5.72 (dd, J=5.9 & 15.5 Hz, 1H)

Example 19

Synthesis of methyl (11R,12S,13E,15S,17R)-9-phenethyl-11,15-bis(tert-butyldimethylsiloxy)-17,20-dimethyl-7-thiaprosta-8,13-dienoate

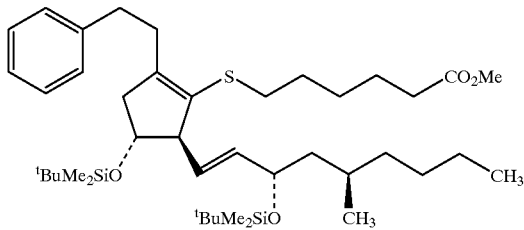

Styrene (150 μl, 1.0 mmol) in tetrahydrofuran (3 mL) was ice-cooled, then 9-BBN, (0.5M THF solution, 2.1 mL, 1.05 mmol) was added. This was agitated for 6 hours while gradually raising the reaction temperature to room temperature. Further, to this were added methyl (11R,12S,13E,15S, 17R)-9-trifluoromethanesulfonyloxy-11,15-bis(tert-butyldimethylsiloxy)-17,20-dimethyl-7-thiaprosta-8,13-dienoate (233 mg, 0.3 mmol), bistriphenylphosphinepalladiumchloride (70 mg, 0.1 mmol), and tripotassium phosphate (255 mg, 1.2 mmol) in tetrahydrofuran (5 mL) suspension. The reaction mixture was agitated at 60° C. for 15 hours. The reaction solution was cooled, then subjected to Florisil column chromotography to remove the metal complexes. The obtained solution was concentrated under reduced pressure, then was purified by silica gel column chromatography (2 to 4% ethyl acetate/hexane) to obtain methyl (11R,12S,13E,15S,17R)-9-phenethyl-11,15-bis(tert-butyldimethylsiloxy)-17,20-dimethyl-7-thiaprosta-8,13-dienoate (104 mg, 48%).
$^1$H-NMR (270 MHz, δppm, CDCl$_3$): 0.03 (s), 0.04 (s) . . . 12H, 0.8–1.0 (m, 6H), 0.87 (s, 9H), 0.94 (s, 9H), 1.0–1.7 (m, 15H), 2.1–2.7 (m, 10H), 3.12 (d, J=7.3 Hz, 1H), 3.66 (s, 3H), 4.0–4.2 (m, 2H), 5.29 (dd, J=8.3 & 15.2 Hz, 1H), 5.46 (dd, J=6.3 & 15.2 Hz, 1H), 7.1–7.3 (m, 5H)

Example 20

Synthesis of methyl (11R,12S,13E,15S,17R)-9-phenethyl-11,15-dihydroxy-17,20-dimethyl-7-thiaprosta-8,13-dienoate

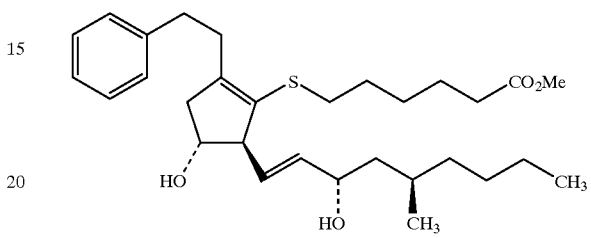

To a solution of ice-cooled acetonitrile (1 ml) and pyridine (0.1 mL) was added hydrogen fluoride-pyridine (0.1 mL). To this solution was added methyl (11R,12S,13E,15S,17R)-9-phenethyl-11,15-bis(tert-butyldimethylsiloxy)-17,20-dimethyl-7-thiaprosta-8,13-dienoate (52 mg, 0.072 mmol) in pyridine (0.1 mL). The ice bath was removed and the solution was agitated for 15 hours wile returning it to room temperature. The reaction solution was poured into a mixture of ethyl acetate and saturated aqueous sodium hydrogencarbonate. The desired product was extracted from this mixed solution by ethyl acetate. The extract was washed with brine, then dried over anhydrous sodium sulfate. The solution was concentrated under reduced pressure, then was purified by silica gel column chromatography (40 to 50% ethyl acetate/hexane) to obtain methyl (11R,12S,13E,15S, 17R)-9-phenethyl-11,15-dihydroxy-17,20-dimethyl-7-thiaprosta-8,13-dienoate (32 mg, 90%).
$^1$H-NMR (270 MHz, δppm, CDCl$_3$): 0.8–1.0 (m, 6H), 1.1–1.8 (m, 15H), 2.2–2.8 (m, 10H), 3.18 (d, J=6.6 Hz, 1H), 3.66 (s, 3H), 4.0–4.1 (m, 1H), 4.1–4.3 (m, 1H), 5.44 (dd, J=7.9 & 15.5 Hz, 1H), 5.46 (dd, J=5.9 & 15.5 Hz, 1H), 7.1–7.3 (m, 5H)
$^{13}$C-NMR (67.5 MHz, δppm, CDCl$_3$): 14.6, 19.9, 23.4, 24.9, 28.5, 29.6, 29.6, 30.1, 31.4, 31.5, 34.4, 37.6, 43.8, 45.3, 52.0, 60,5, 71.0, 76.7, 126.4, 128.8, 128.9, 129.9, 130.0, 136.1, 141.9, 142.8, 174.6

Example 21

Synthesis of methyl (11R,12S,13E,15S,17R)-9-formyl-11,15-bis(tert-butyldimethylsiloxy)-17,20-dimethyl-7-thiaprosta-8,13-dienoate

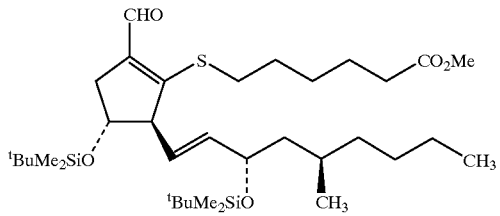

Methyl (11R,12S,13E,15S,17R)-9-trifluoromethanesulfonyloxy-11,15-bis(tert-butyldimethylsiloxy)-17,20-dimethyl-7-thiaprosta-8,13-dienoate (120 mg, 0.154 mmol), palladium acetate (11.2 mg, 0.05 mmol), triphenylphosphine (26 mg, 0.1 mmol), formic acid (12 μl, 0.309 mmol), and triethylamine (65 μl, 063 mmol) in tetrahydrofuran (6 mL) were placed in an autoclave into which carbon monoxide gas was pumped under pressure to give the internal pressure of 17 atmospheres. The solution was heated and agitated at 80° C. for 15 hours. This was dissolved in dimethylformamide (2 ml). Methanol (810 μl, 20 mmol) and triethylamine (139 μl, 1 mmol) were added. This was agitated in carbon monoxide atmosphere (1 atmosphere) at room temperature for further 18 hours. The reaction vessel was cooled to room temperature, then carbon monoxide in the reaction vessel was removed, the reaction solution thus obtained was passed through Florisil column, was concentrated under reduced pressure, and was purified by silica gel column chromatography (2 to 5% ethyl acetate/hexane) to obtain methyl (11R,12S,13E,15S,17R)-9-formyl-11,15-bis(tert-butyldimethylsiloxy)-17,20-dimethyl-7-thiaprosta-8,13-dienoate as a crude (21 mg).

$^1$H-NMR (270 MHz, δppm, CDCl$_3$): 0.0–0.2 (m, 12H), 0.8–1.0 (m, 24H), 1.1–1.7 (m, 15H), 2.2–2.4 (m, 2H), 2.53 (d, J=17.2 Hz, 1H), 2.6–3.1 (m, 3H), 3.49 (d, J=8.3 Hz, 1H), 3.67 (s, 3H), 4.1–4.3 (m, 2H), 5.44 (dd, J=7.9 & 15.7 Hz, 1H), 5.62 (dd, J=5.9 & 15.1 Hz, 1H), 10.04 (s, 1H)

Example 22

Synthesis of methyl (11R,12S,13E,15S,17R)-9-formyl-11,15-dihydroxy-17,20-dimethyl-7-thiaprosta-8,13-dienoate

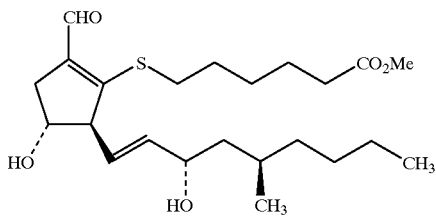

To a solution of ice-cooled acetonitrile (1 ml) and pyridine (0.1 mL) was added hydrogen fluoride-pyridine (0.1 mL). To this solution was added a mixture of (21 mg) containing methyl(11R,12S,13E,15S,17R)-9-formyl-11,15-bis(tert-butyldimethylsiloxy)-17,20-dimethyl-7-thiaprosta-8,13-diene acid in pyridine (0.1 mL). The ice bath was removed and the solution was agitated for 15 hours while returning it to room temperature. The reaction solution was poured into a mixture of ethyl acetate and saturated aqueous sodium hydrogencarbonate. The desired product was extracted from this mixed solution with ethyl acetate. The extract was washed with brine, then dried over anhydrous sodium sulfate. The solution was concentrated under reduced pressure, then was subjected to thin layer chromotography (ethyl acetate/hexane=4/1) to obtain methyl (11R,12S,13E,15S, 17R)-9-formyl-11,15-dihydroxy-17,20-dimethyl-7-thiaprosta-8,13-dienoate in an amount of 3.4 mg (5.2%).

$^1$H-NMR (270 MHz, δppm, CDCl$_3$): 0.8–1.0 (m, 24H) 1.1–1.8 (m, 15H) 2.33 (t, J=7.3 Hz, 2H) 2.59 (d, J=16.8 Hz, 1H) 2.6–3.1 (m, 3H) 3.63 (d, J=7.3 Hz, 1H) 3.67 (s, 3H) 4.1–4.3 (m, 2H) 5.59 (dd, J=7.6 & 15.5 Hz, 1H) 5.71 (dd, J=5.6 & 15.5 Hz, 1H) 10.05 (s, 1H) IR (neat) 3418/S, 2926/S, 2858/S, 2723/W, 1738/S, 1651/S, 1556/M, 1437/M, 1379/M, 1257/M, 1203/M, 1047/M, 974/M, 862/W, 729/W

EXAMPLE 23

Synthesis of methyl (11R,12S,13E,15S,17R)-9-methoxycarbonyl-11,15-bis(tert-butyldimethylsiloxy)-17,20-dimethyl-7-thiaprosta-8,13-dienoate

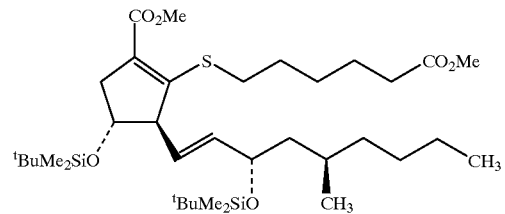

Methyl (11R,12S,13E,15S,17R)-9-trifluoromethanesulfonyloxy-11,15-bis(tert-butyldimethylsiloxy)-17,20-dimethyl-7-thiaprosta-8,13-dienoate (388 mg, 0.5 mmol), palladium acetate (11.2 mg, 0.05 mmol), and triphenylphospine (26.2 g, 0.1 mmol) were dissolved in dimethylformamide (2 mL). To this were added methanol (810 μl, 20 mmol) and triethylamine (139 μl, 1 mmol). This was agitated in carbon monoxide atmosphere (1 atmosphere) at room temperature for 18 hours. 10 ml of water was added, the solution separated, and the aqueous phase was extracted with ether and the extract combined with the organic layer. The organic solution was washed with brine, then was dried over anhydrous sodium sulfate. The solution was concentrated under reduced pressure, then was purified by silica gel column chromatography (4% ethyl acetate/hexane) to obtain methyl (11R,12S,13E,15S,17R)-9-methoxycarbonyl-11,15-bis(tert-butyldimethylsiloxy)-17,20-dimethyl-7-thiaprosta-8,13-dienoate (134 mg, 38%).

$^1$H-NMR (270 MHz, δppm, CDCl$_3$): 0.01 (s), 0.03 (s), 0.06 (s), 0.0 7. . . 12H 0.8–10 (m, 6H) 0.88 (s, 9H) 0.88 (s, 9H) 1.0–1.7 (m, 15H) 2.30 (t, J=7.4 Hz, 2H) 2.54 (d, J=15.5 Hz, 1H) 2.6–2.9 (m, 3H) 3.45 (t, J=6.9 Hz, 1H) 3.66 (s, 3H) 3.75 (s, 3H) 4.0–4.2 (m, 1H) 4.07 (d, J=5.3 Hz, 1H) 5.48 (dd, J=7.1 & 15.7 Hz, 1H) 5.60 (dd, J=5.8 & 15.7 Hz, 1H)

EXAMPLE 24

Synthesis of methyl (11R,12S,13E,15S,17R)-9-methoxycarbonyl-11,15-dihydroxy-17,20-dimethyl-7-thiaprosta-8,13-dienoate

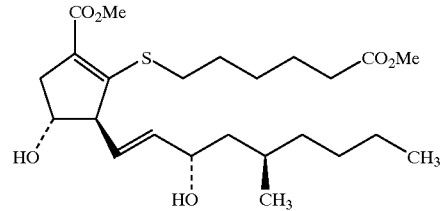

To a solution of ice-cooled acetonitrile (1 mL) and pyridine (10 mL) was added a hydrogen fluoride-pyridine (0.1 mL). To this solution was added methyl (11R,12S,13E,15S, 17R)-9-methoxycarbonyl-11,15-bis(tert-butyldimethylsiloxy)-17,20-dimethyl-7-thiaprosta-8,13-dienoate (67 mg, 0.097 mmol) in pyridine (0.1 mL). The ice bath was removed and the solution was agitated for 15 hours while returning it to room temperature. The reaction solution was poured into a mixture of ethyl acetate and saturated aqueous sodium hydrogencarbonate. The desired product was extracted from this mixed solution with ethyl acetate.

The extract was washed with brine, then dried over anhydrous sodium sulfate. The solution was concentrated under reduced pressure, then was purified by silica gel column chromatography (40 to 50% ethyl acetate/hexane) to obtain methyl (11R,12S,13E,15S,17R)-9-methoxycarbonyl-11,15-dihydroxy-17,20-dimethyl-7-thiaprosta-8,13-dienoate (35 mg, 78%).

$^1$H-NMR (270 MHz, δppm, CDCl$_3$): 0.8–1.0 (m, 6H) 1.1–1.7 (m, 15H) 2.31 (t, J=7.4 Hz, 2H) 2.60 (d, J=16.8 Hz, 1H) 2.7–3.0 (m, 3H) 3.61 (d, J=5.3 Hz, 1H) 3.67 (s, 3H) 3.76 (s, 3H) 4.13 (d, J=4.6 Hz, 1H) 4.19 (dt, J=8.6 & 4.6 Hz, 1H) 5.5–5.8 (m, 2H)

EXAMPLE 25

Synthesis of methyl (11R,12S,13E,15S,17R)-9-acetyl-11,15-bis(tert-butyldimethylsiloxy)-17,20-dimethyl-7-thiaprosta-8,13-dienoate

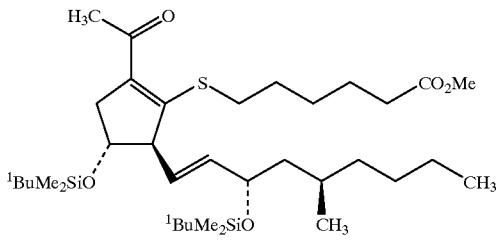

Methyl (11R,12S,13E,15S,17R)-9-trifluoromethanesulfonyloxy-11,15-bis(tert-butyldimethylsiloxy)-17,20-dimethyl-7-thiaprosta-8,13-dienoate (388 mg, 0.5 mmol), tris(benzylidenacetone) dipalladium (11.4 mg, 0.0125 mmol)triphenylphosphine (13.1 mg, 0.05 mmol), lithium chloride (55.3 mg, 1.3 mmol), and trimethyltin (69 μl, 0.5 mmol) in tetrahydrofuran (5 mL) were placed in an autoclave reactor. Carbon monoxide gas was pumped into this to make the internal pressure 5 atmospheres. This was agitated for 15 minutes. Next, carbon monoxide in the reactor was removed, then the lid of the autoclave reactor was opened and zinc chloride (68.1 mg, 0.5 mmol) was placed in the reaction vessel. Carbon monoxide was again pumped in to 5 atmospheres, then the solution was heated and agitated at 75° C. for 15 hours. The reaction vessel was cooled to room temperature, then carbon monoxide in the reaction vessel was removed, the reaction solution thus obtained was passed through Florisil column, the solution was concentrated under reduced pressure, then was purified by silica gel column chromatography (2 to 5% ethyl acetate/hexane) to obtain methyl (11R,12S,13E,15S,17R)-9-acetyl-11,15-bis(tert-butyldimethylsiloxy)-17,20-dimethyl-7-thiaprosta-8,13-dienoate in an amount of 24 mg (8%).

$^1$H-NMR (270 MHz, δppm, CDCl$_3$): 0.01 (s), 0.03 (s), 0.07 (s) . . . 12H 0.8–1.0 (m, 6H) 0.88 (s, 9H) 0.88 (s, 9H) 1.0–1.7 (m, 15H) 2.26 (s, 3H) 2.30 (t, J=7.3 Hz, 2H) 2.56 (d, J=16.2 Hz, 1H) 2.6–3.0 (m, 3H) 3.49 (d, J=6.6 Hz, 1H) 3.66 (s, 3H) 4.0–4.2 (m, 2H) 5.48 (dd, J=6.2 & 15.7 Hz, 1H) 5.60 (dd, J=5.6 & 15.5 Hz, 1H)

EXAMPLE 26

Synthesis of methyl (11R,12S,13E,15S,17R)-9-acetyl-11,15-dihydroxy-17,20-dimethyl-7-thiaprosta-8,13-dienoate

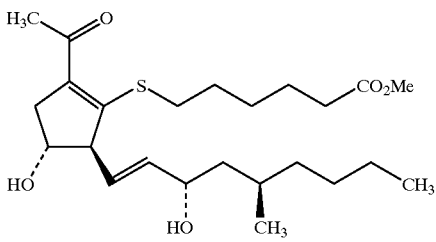

To a solution of ice-cooled acetonitrile (1 mL) and pyridine (0.1 mL) was added a hydrogen fluoride-pyridine solution (0.1 mL). To this solution was added methyl (11R,12S,13E,15S,17R)-9-acetyl-11,15-bis(tert-butyldimethylsiloxy)-17,20-dimethyl-7-thiaprosta-8,13-dienoate (12 mg, 0.019 mmol) in pyridine (0.1 mL). The ice bath was removed and the solution was agitated for 15 hours, while returning it to room temperature. The reaction solution was poured into a mixture of ethyl acetate and a saturated aqueous sodium hydrogencarbonate. The desired product was extracted from this mixed solution of ethyl acetate. The extract was washed with brine, then dried over anhydrous sodium sulfate. The solution was concentrated under reduced pressure, then subjected to thin layer chromatography for separation (ethyl acetate:hexane=3:1) to obtain methyl (11R,12S,13E,15S,17R)-9-acetyl-11,15-dihydroxy-17,20-dimethyl-7-thiaprosta-8,13-dienoate (3.2 mg, 39%).

$^1$H-NMR (270 MHz, δppm, CDCl$_3$): 0.8–1.0 (m, 6H) 1.1–1.7 (m, 15H) 2.28 (s, 3H) 2.31 (t, J=7.3 Hz, 2H) 2.64 (d, J=16.5 Hz, 1H) 2.7–3.0 (m, 2H) 3.03 (dd, J=5.1 & 16.3 Hz, 1H) 3.6–3.7 (m, 1H) 3.67 (s, 3H) 4.1–4.3 (m, 2H) 5.5–5.8 (m, 2H)

EXAMPLE 27

Synthesis of methyl (11R,12S,13E,15S,17R)-11,15-bis(tert-butyldimethylsiloxy)-17,20-dimethyl-7-thiaprosta-8,13-dienoate

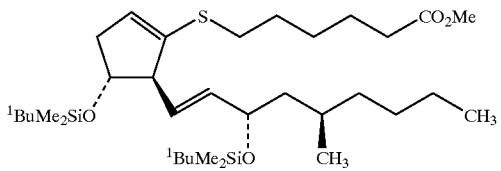

Methyl (11R,12S,13E,15S,17)-9-trifluoromethanesulfonyloxy-11,15-bis(tert-butyldimethylsiloxy)-17,20-dimethyl-7-thiaprosta-8,13-dienoate (233 mg, 0.3 mmol), bistriphenylphosphinepalladium(II)acetate (45 mg, 0.06 mmol), formic acid (22.6 μl, 0.6 mmol), and triethylamine (125 μl, 0.9 mmol) in dimethylformamide (1 mL) were agitated at 60° C. for 3 hours. The reaction solution was cooled and subjected to Florisil column chromatography to remove the metal complexes. The solution thus obtained was concentrated under reduced pressure, then was purified by silica gel column chromatography (2% ethyl acetate/hexane) to obtain methyl (11R,12S,13E,15S,17R)-11,15-bis(tert-butyldimethylsiloxy)-17,20-dimethyl-7-thiaprosta-8,13-dienoate (150 mg, 79%).

$^1$H-NMR (270 MHz, δppm, CDCl$_3$): 0.00 (s), 0.05 (s) . . . 12H 0.8–0.9 (m, 6H) 0.87 (s, 9H) 0.89 (s, 9H) 1.1–1.8 (m, 15H) 2.2–2.4 (m, 3H) 2.6–2.8 (m, 3H) 3.10 (d, J=6.6 Hz, 1H) 3.66 (s, 3H) 4.1–4.3 (m, 2H) 5.27 (d, J=1.7 Hz, 1H) 5.34 (dd, J=9.4 & 15.3 Hz, 1H) 5.56 (dd, J=6.3 & 15.5 Hz, 1H)

EXAMPLE 28

Synthesis of methyl (11R,12S,13E,15S,17R)-11,15-dihydroxy-17,20-dimethyl-7-thiaprosta-8,13-dienoate

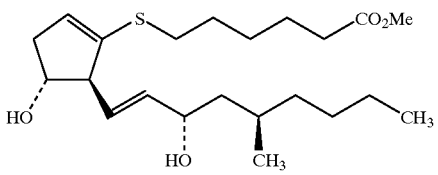

To a solution of ice-cooled acetonitrile (1.5 mL) and pyridine (0.15 mL) was added hydrogen fluoride-pyridine (0.15 mL). To this solution was added methyl (11R,12S, 13E,15S,17R)-11,15-bis(tert-butyldimethylsiloxy)-17,20-dimethyl-7-thiaprosta-8,13-dienoate (150 mg, 0.238 mmol) in pyridine (0.15 mL). The ice bath was removed and the solution was agitated for 15 hours, while returning it to room temperature. The reaction solution was poured into a mixture of ethyl acetate and saturated aqueous sodium hydrogencarbonate. The desired product was extracted from this mixed solution with ethyl acetate. The extract was washed with brine, then dried over anhydrous sodium sulfate. The solution was concentrated under reduced pressure, then was purified by silica gel column chromatography (40 to 50% ethyl acetate/hexane) to obtain methyl (11R,12S,13E,15S, 17R)-11,15-dihydroxy-17,20-dimethyl-7-thiaprosta-8,13-dienoate (82 mg, 86%).

$^1$H-NMR (270 MHz, δppm, CDCl$_3$): 0.8–1.0 (m, 6H) 1.1–1.8 (m, 15H) 2.2–2.4 (m, 3H) 2.6–2.8 (m, 3H) 3.–3.2 (m, 1H) 3.67 (s, 3H) 4.1–4.3 (m, 2H) 5.27 (d, J=2.0 Hz, 1H) 5.46 (dd, J=8.9 & 15.2 Hz, 1H) 5.56 (dd, J=7.3 & 15.2 Hz, 1H) $^{13}$C-NMR (67.5 MHz, δppm, CDCl$_3$): 14.1, 19.6, 22.9, 24.4, 28.2, 28.4, 29.0, 29.0, 31.1, 33.8, 36.8, 39.9, 44.6, 51.4, 60.0, 70.7, 78.2, 118.4, 130.1, 136.7, 138.1, 174.0.

EXAMPLE 29

Synthesis of (11R,12S,13E,15S,17R)-11,15-dihydroxy-17,20-dimethyl-7-thiaprosta-8,13-dienoic acid

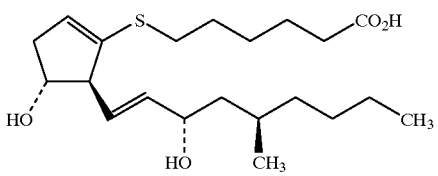

To methyl (11R,12S,13E,15S,17R)-11,15-dihydroxy-17, 20-dimethyl-7-thiaprosta-8,13-dienoate (37.2 mg, 0.093 mmol) in acetone (1 mL) was added pH 8 phosphate buffer (10 mL). To this was further added esterase containing solution (derived from pig's liver, made by Sigma Co., 100 μl). This was agitated at room temperature for 15 hours. Dilute hydrochloric acid was added to the reaction solution to make the solution pH 4. Further, The solution was made saturated by ammonium sulfate, then the target produce was extracted with ethyl acetate. The extract was washed with brine, then was dried over anhydrous sodium sulfate. The solution was concentrated under reduced pressure, then subjected to thin layer chromatography for separation (development solution: ethyl acetate) to obtain (11R,12S, 13E,15S,17R)-11,15-dihydroxy-17,20-dimethyl-7-thiaprosta-8,13-dienoic acid (4.6 mg, 12%).

$^1$H-NMR (270 MHz, δppm, CDCl$_3$): 0.8–1.0 (m, 6H) 1.1–1.8 (m, 15H) 2.2–2.4 (m, 3H) 2.6–2.8 (m, 3H) 3.1–3.2 (m, 1H) 4.1–4.3 (m, 2H) 5.32 (d, J=1.3 Hz, 1H) 5.50 (dd, J=8.4 & 15.3 Hz, 1H) 5.65 (dd, J=6.4 & 15.3 Hz, 1H)

EXAMPLE 30

Synthesis of methyl(11R,12S,13E,15S)-11,15-bis(tert-butyldimethylsiloxy)-16-phenyl-17,18,19,20-tetranol-7-thiaprosta-8,13-dienoate

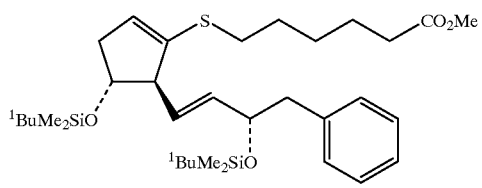

Methyl (11R,12S,13E,15S)-9-trifluoromethanesulfonyloxy-11,15-bis(tert-butyldimethylsiloxy)-16-phenyl-17,18,19,20-tetranol-7-thiaprosta-8,13-dienoate (230 mg, 0.3 mmol), bistriphenylphosphinepalladium(II)acetate (45 mg, 0.06 mmol), formic acid (27.6 mg), and triethylamine (91 mg) in dimethylformamide (1 mL) were agitated at 60° C. for 3 hours. The reaction solution was cooled and subjected to Florisil column chromatography to remove the metal complexes. The obtained solution was concentrated under reduced pressure, then was purified by silica gel column chromatography (3.5% ethyl acetate/hexane) to obtain methyl (11R,12S,13E,15S)-11,15-bis(tert-butyldimethylsiloxy)-16-phenyl-17,18,19,20-tetranol-7-thiaprosta-8,13-dienoate (134 mg, 74%).

$^1$H-NMR (270 MHz, δppm, CDCl$_3$): −0.20 (s, 3H) −0.07 (s, 3H) 0.01 (s, 6H) 0.82 (s, 9H) 0.88 (s, 9H) 1.3–1.5 (m, 2H) 1.52–1.75 (m, 4H) 2.2–2.4 (m, 3H) 2.55–2.8 (m, 5H) 3.08 (dd, J=1.9 & 8.7 Hz, 1H) 3.66 (s, 3H) 4.1–4.17 (m, 1H) 4.22–4.29 (m, 1H) 5.27 (dd, J=1.0 & 1.0 Hz, 1H) 5.39 (ddd, J=1.0 & 8.9 & 15.5 Hz, 1H) 5.62 (dd, J=15.5 & 5.4 Hz, 1H) 7.1–7.3 (m, 5H)

EXAMPLE 31

Synthesis of methyl (11R,12S,13E,15S)-11,15-dihydroxy-16-phenyl-17,18,19,20-tetranol-7-thiaprosta-8, 13-dienoate

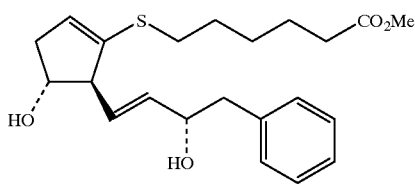

To a solution of ice-cooled acetonitrile (1.0 mL) and pyridine (0.25 mL) was added hydrogen fluoride-pyridine (0.25 mL). To this solution was added methyl (11R,12S, 13E,15S)-11,15-bis(tert-butyldimethylsiloxy)-16-phenyl-17,18,19,20-tetranol-7-thiaprosta-8,13-dienoate (120 mg) in pyridine (0.25 mL). The ice bath was removed and the solution was agitated for 19 hours while returning it to room temperature. The reaction solution was poured into a mixture of ethyl acetate and saturated aqueous sodium hydrogen carbonate. The desired produce was extracted from this mixed solution with ethyl acetate. The extract was washed with brine, then dried over anhydrous sodium sulfate. The solution was concentrated under reduced pressure, then was purified by silica gel column chromatography (55% ethyl acetate/hexane) to obtain methyl (11R,12S,13E,15S)-11,15-dihydroxy-16-phenyl-17,18,19,20-tetranol-7-thiaprosta-8,13-dienoate (58 mg, 78%).

$^1$H-NMR (270 MHz, δppm, CDCl$_3$): 1.35–1.5 (m, 2H) 1.6–1.72 (m, 4H) 1.84 (br-d, J=5.6 Hz, 1H) 2.32 (t, J=7.3 Hz, 2H) 2.34 (br, 1H) 2.65–2.95 (m, 5H) 3.08 (dd, J=3.0 & 7.9 Hz, 1H) 3.67 (s, 3H) 4.1–4.2 (br, 1H) 4.3–4.4 (br, 1H) 5.30 (dd, J=2.3 & 4.0 Hz, 1H) 5.49 (ddd, J=2.3 & 8.6 & 15.2 Hz, 1H) 5.71 (dd, J=6.3 & 15.2 Hz, 1H) 7.2–7.35 (m, 5H)

EXAMPLE 32

Synthesis of methyl (11R,12S,13E)-11,15-bis(tert-butyldimethylsiloxy)-9-methyl-16-phenyl-17,18,19,20-tetranol-7-thiaprosta-8,13-dienoate

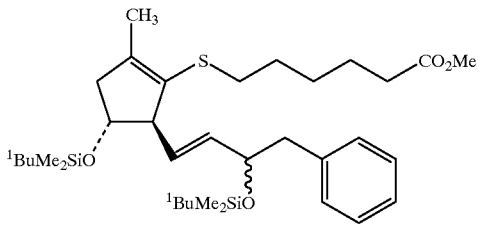

Methyl (11R,12S,13E)-9-trifluoromethanesulfonyloxy-11,15-bis(tert-butyldimethylsiloxy)-16-phenyl-17,18,19,20-tetranol-7-thiaprosta-8,13-dienoate synthesized using the racemate (1E)-1-iodo-3-(tert-butyldimethylsiloxy)-4-phenyl-1-butene as the starting material in accordance with the method of Example 4 was used. To tetrakistriphenylphosphinepalladium prepared in advance in the system from tris(dibenzylideneacetone) dipalladium(0) (132 mg, 0.12 mmol) and triphenylphosphine (265 mg, 1.0 mmol) were added methyl (11R,12S,13E)-9-trifluoromethanesulfonyloxy-11,15-bis(tert-butyldimethylsiloxy)-16-phenyl-17,18,19,20-tetranol-7-thiaprosta-8,13-dienoate (486 mg, 0.635 mmol) in 1,2-dichloroethane (10 mL) and 1.0M trimethyl aluminum in hexane (1.0 mL, 1.0 mmol). This was agitated at 50° C. for 2 hours. Ether was added to dilute the reaction solution, then the solution was poured in 1N hydrochloric acid. The desired product was extracted with ether from the mixture. The extract was washer with brine, then was dried over anhydrous sodium sulfate. The solution was concentrated under reduced pressure, then was purified by silica gel column chromatography (4% ethyl acetate/hexane) to obtain methyl (11R,12S,13E)-11,15-bis(tert-butyldimethylsiloxy)-9-methyl-16phenyl-17,18,19,20-tetranol-7-thiaprosta-8,13-dienoate (305 mg, 76%).

$^1$H-NMR (270 MHz, δppm, CDCl$_3$): −0.25 (s, 3H) −0.10 (s, 3H) 0.04 (s, 6H) 0.82 (s, 9H) 0.87 (s, 9H) 1.27–1.68 (m, 6H) 1.79 (s, 3H) 2.15–2.45 (m, 2H) 2.29 (t, 2H, J=7.3 Hz) 2.52–2.70 (m, 2H) 2.70–2.81 (m, 2H) 3.11 (d, 1H, J=8.3 Hz) 3.66 (s, 3H) 3.97–4.08 (m, 1H) 4.19–4.30 (m, 1H) 5.39 (dd, 1H, J=15.3, 8.6 Hz) 5.57 (dd, 1H, J=15.3, 5.6 Hz) 7.10–7.29 (m, 5H)

EXAMPLE 33

Synthesis of methyl (11R,12S,13E)-9-methyl-11,15-dihydroxy-16-phenyl-17,18,19,20-tetranol-7-thiaprosta-8,13-dienoate

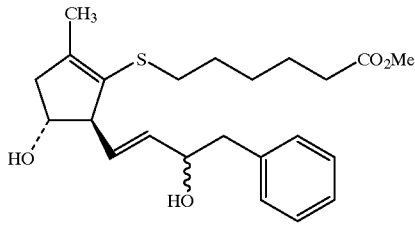

To a solution of ice-cooled acetonitrile (2 mL) and pyridine (0.5 mL) was added hydrogen fluoride-pyridine (0.5 mL). To this solution was added methyl (11R,12S,13E)-11,15-bis(tert-butyldimethylsiloxy)-9-methyl-16-phenyl-17,18,19,20-tetranol-7-thiaprosta-8,13-dienoate (305 mg, 0.48 mmol) in pyridine (0.5 mL). The ice bath was removed and the solution was agitated for 14 hours while returning it to room temperature. The reaction solution was poured into a mixture of ethyl acetate and saturated aqueous sodium hydrogencarbonate. The desired product was extracted from this mixed solution with ethyl acetate. The extract was washed with brine, then dried over anhydrous sodium sulfate. The solution was concentrated under reduced pressure, then was purified by silica gel column chromatography (ethyl acetate/hexane) to obtain the 15-position stereoisomers of methyl (11R,12S,13E)-9-methyl-11,15-dihydroxy-16-phenyl-17,18,19,20-tetranol-7-thiaprosta-8,13-dienoate separately (less polar compounds: 75 mg, 39%; more polar compounds: 76 mg, 39%). $^1$H-NMR (270 MHz, δppm, CDCl$_3$): less polar compounds 1.20–1.80 (m, 6H) 1.81 (s, 3H) 1.85 (br.s, 1H) 2.19–2.30 (m, 1H) 2.31 (t, 2H, J=7.3 Hz) 2.40–2.53 (m, 1H) 2.55–2.74 (m, 2H) 2.78–2.95 (m, 2H) 3.2 (d, 1H, J=8.3 Hz) 3.66 (s, 3H) 3.92–4.03 (m, 1H) 4.30–4.42 (m, 1H) 5.44 (dd, 1H, J=15.5, 8,6 Hz) 5.65 (dd, 1H, J=15.5, 6.3 Hz) 7.18–7.36 (m, 5H) more polar compounds 1.35–1.71 (m, 6H) 1.82 (s, 3H) 2.00 (br.s, 1H) 2.22–2.33 (m, 1) 2.31 (t, 2H, J=7.3 Hz) 2.38–2.51 (m, 1H) 2.53–2.75 (m, 2H) 2.75–2.94 (m, 2H) 3.21 (d, 1H, J=7.3 Hz) 3.66 (s, 3H) 4.04–4.12 (m, 1H) 4.32–4.44 (m, 1H) 5.52 (dd, 1H, J=15.5, 8.3 Hz) 5.67 (dd, 1H, J=15.5, 6.3 Hz) 7.19–7.35 (m, 5H)

EXAMPLE 34

Synthesis of (11R,12S,13E)-9-methyl-11,15-dihydroxy-16-phenyl-17,18,19,20-tetranol-7-thiaprosta-8,13-dienoic acid

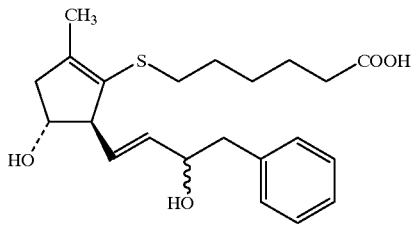

Of the two types of isomers of the methyl (11R,12S,13E)-9-methyl-11,15-dihydroxy-16-phenyl-17,18,19,20-tetranol-7-thiaprosta-8,13-dienoate obtained in Example 33, the more polar compound (30.6 mg, 0.076 mmol) was dissolved in an acetone (1 mL) then pH 8 phosphate buffer (10 mL) was added. To this was further added esterase containing solution (derived from pig's liver, made by Sigma Co., 10 drops). This was agitated at room temperature for 15 hours. Dilute hydrochloric acid was added to the reaction solution to make the solution pH 4. Further, the solution was made saturated by ammonium sulfate, then the desired product was extracted with ethyl acetate. The extract was washed with brine, then was dried over anhydrous sodium sulfate. The solution was concentrated under reduced pressure, then subjected to HPLC (normal bonded phase column; hexane/ethanol/acetic acid, 80:20:0.1) to obtain (11R,12S,13E)-9-methyl-11,15-dihydroxy-16-phenyl-17,18,19,20-tetranol-7-thiaprosta-8,13-dienoic acid (15 mg, 51%).

$^1$H-NMR (270 MHz, δppm, CDCl$_3$): 1.30–1.82 (m, 6H) 1.81 (s, 3H) 2.21–2.47 (m, 2H) 2.33 (t, 2H, J=7.3 Hz) 2.50–2.83 (m, 2H) 2.85–2.93 (m, 2H) 3.15–3.24 (m, 1H) 3.53 (br, 2H) 3.75 (s, 3H) 4.06 (dt, 1H, J=6.9, 3.3 Hz) 4.36 (dt, 1H, J=6.6, 6.6 Hz) 5.51 (dd, 1H, J=15.5, 7.9 Hz) 5.65 (dd, 1H, J=15.5. 6.6 Hz) 7.16–7.35 (m, 5H)

EXAMPLE 35

Synthesis of methyl (11R,12S,13E)-9-cyclopropyl-11,15-bis(tert-butyldimethylsiloxy)-16-phenyl-17,18,19,20-tetranol-7-thiaprosta-8,13-dienoate

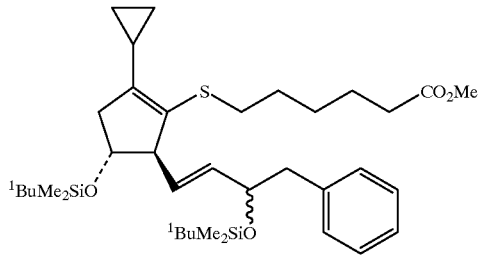

Cyclopropyl bromide (0.40 mL, 5.0 mmol) was disolved in 25 mL of ether and cooled to −78° C. To this was added 1.50M tert-butyllithium (0.35 mL, 5.3 mmol). This was agitated at −78° C. for 3 hours to give a cyclopropyllithium solution. This was added to a solution of CuCN (233 mg, 2.60 mmol) dissolved in 45 ml of dried ether at −78° C. This was agitated at −50° C. for 30 minutes, then again cooled to −78° C. Methyl (11R,12S,13E)-9-trifluoromethanesulfonyloxy-11,15-bis(tert-butyldimethylsiloxy)-16-phenyl-17,18,19,20-tetranol-7-thiaprosta-8,13-dienoate [synthesized using the racemate (1E)-1-iodo-3-(tert-butyldimethylsiloxy)-4-phenyl-1-butane as a starting material in accordance with the method of Example 4] in dry ether (2 mL) was added. This was agitated for 15 hours while gradually raising the temperature to room temperature. The reaction solution was poured into 30 ml of a mixture of saturated aqueous ammonium sulfate and concentrated ammonia water (9:1) to end the reaction. The mixture was separated, then the aqueous layer was extracted with ether (30 mL). The extract was combined with the organic layer and was washed with brine, then dried over anhydrous magnesium sulfate. This was concentrated under reduced pressure, then was purified by silica gel column chromatography (0.5% ethyl acetate/hexane), then was subjected to HPLC (normal bonded phase column; 1.5% ethyl acetate/hexane) to obtain methyl (11R,12S,13E)-9-cyclopropyl-11,15-bis(tert-butyldimethylsiloxy)-16-phenyl-17,18,19,20-tetranol-7-thiaprosta-8,13-dienoate (15-position stereomixture: 32 mg 10%).

$^1$N-NMR (270 MHz, δppm, CDCl$_3$): −0.23 (s, 3H) −0.10 (s, 3H) 0.02 (s, 6H) 0.45–0.60 (m, 2H) 0.64–0.75 (m, 2H) 0.81 (s, 9H) 0.86 (s, 9H) 1.20–1.69 (m, 6H) 1.97–2.11 (m, 1H) 2.18–2.80 (m, 6H) 2.30 (t, J=7.3 Hz, 2H) 3.09–3.17 (m, 1H) 3.6 (s, 3H) 4.91–4.03 (m, 1H) 4.19–4.30 (m, 1H) 5.33–5.45 (m, 1H) 5.58 (dd, J=15.5, 6.3 Hz, 1H) 7.13–7.30 (m, 5H)

EXAMPLE 36

Synthesis of methyl (11R,12S,13E)-9-cyclopropyl-11,15-dihydroxy-16-phenyl-17,18,19,20-tetranol-7-thiaprosta-8,13-dienoate

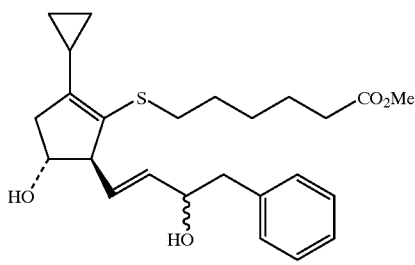

To a solution of ice-cooled acetonitrile (1 mL) and pyridine (0.25 mL) was added hydrogen fluoride-pyridine solution (0.25 mL). To this solution was added methyl (11R,12S,13E)-11,15-bis(tert-butyldimethylsiloxy)-9-cyclopropyl-16-phenyl-17,18,19,20-tetranol-7-thiaprosta-8,13-dienoate (32 mg, 0.049 mmol) in pyridine (0.25 mL). The ice bath was removed and the solution was agitated for 17 hours, while returning it to room temperature. The reaction solution was poured into a mixture of ethyl acetate and saturated aqueous sodium hydrogencarbonate. The desired produce was extracted from this mixed solution with ethyl acetate, was washed with brine, then was dried over anhydrous sodium sulfate. This was concentrated under reduced pressure, then subjected to HPLC (normal bonded phase column ZORBAX-SIL; 5% ethyl acetate/hexane) to obtain 15-position stereoisomers of methyl (11R,12S,13E)-9-cyclopropyl-11,15-dihydroxy-16-phenyl-17,18,19,20-tetranol-7-thiaprosta-8,13-dienoate separately (less polar compounds: 3 mg, 14%; more polar compounds: 6.9 mg, 33%).

$^1$H-NMR (270 MHz, δppm, CDCl$_3$): less polar (HPLC) compounds 0.47–0.65 (m, 2H) 0.66–0.78 (m, 2H) 1.23–2.09 (m, 8H) 2.25–2.40 (m, 1H) 2.31 (t, J=7.3 Hz, 2H) 2.41–2.68 (m, 2H) 2.76–2.93 (m, 2H) 3.15–3.26 (m, 1H) 3.66 (s, 3H) 3.97–4.06 (m, 1H) 4.31–4.44 (m, 1H) 5.53 (dd, J=15.5, 7.6 Hz, 1H) 5.68 (dd, J=15.5, 5.9 Hz, 1H) 7.18–7.36 (m, 5H) more polar (HPLC) compounds 0.46–0.65 (m, 2H) 0.66–0.78 (m, 2H) 1.32–2.08 (m, 8H) 2.23–2.38 (m, 1H) 2.31 (t, J=7.6 Hz, 2H) 2.43–2.71 (m, 2H) 2.86–2.95 (m, 2H) 3.12–3.24 (m, 1H) 3.66 (s, 3H) 3.83–3.95 (m, 1H) 4.31–4.43 (m, 1H) 5.44 (dd, J=15.5, 8.6 Hz, 1H) 5.66 (dd, J=15.5, 6.6 Hz, 1H) 7.15–7.36 (m, 5H)

EXAMPLE 37

Synthesis of methyl (13E,15S)-15-(tert-butyldimethylsiloxy)-9-trifluoromethanesulfonyloxy-16-phenyl-17,18,19,20-tetranol-7-thiaprosta-8,13-dienoate

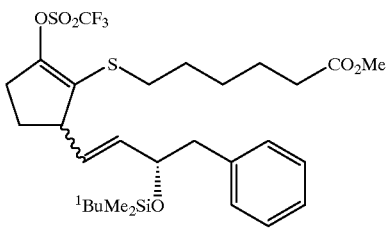

(1E,3S)-1-iodo-3-(tert-butyldimethylsiloxy)-4-phenyl-1-butene (250 mg) in ether (2.5 mL) was cooled to −78° C., then tert-butyllithium (1.50 mol/L, 0.858 mL) was added. This was agitated at −78° C. for 2 hours. Further, to this were added 1-hexynylcopper (I) (93 mg) and hexamethylphosphorus triamide (234 μl) in ether (3.5 mL). This was further agitated at −78° C. for a further 1 hour to give a copper reagent. To the copper reagent thus obtained was added drop-wise 2-(5-methoxycarbonylpentylthio)-2-cyclopenten-1-one (159 mg) in tetrahydrofuran (5.0 mL). This reaction mixture was agitated at −78° C. for 30 minutes, then the reaction temperature was raised and was agitated at −50° to −30° C. for 2 hours. To the conjugate adduct thus obtained was added at −50° C. N-phenyltrifluoromethanesulfonimide (620 mg) in tetrahydrofuran (6 mL). This was agitated for 1 hour, while gradually raising the reaction temperature to room temperature. The reaction solution was poured into saturated aqueous ammonium sulfate (100 m) to end the reaction. The mixture was separated, then the aqueous solution was extracted with ether. The extract was combined with the organic layer, then dried over anhydrous magnesium sulfate. This was concentrated under reduced pressure, then was purified by silica gel column chromatography (5% ethyl acetate/hexane) to obtain methyl (13E,15S)-15-(tert-butyldimethylsiloxy)-9-trifluoromethanesulfonyloxy-16-phenyl-17,18,19,20-tetranol-7-thiaprosta-8,13-dienoate (12-position stereomixture: 239 mg, 59%).

$^1$H-NMR (270 MHz, δppm, CDCl$_3$): −0.21 (s, 3/2H) −0.20 (s, 3/2H) −0.10 (s, 3/2H) −0.08 (s, 3/2H) 0.83 (s, 9H) 1.3–1.8 (m, 8H) 2.31 (t, 2H, J=7.4 Hz) 2.1–2.75 (m, 6H) 3.3 (br, 1H) 3.66 (s, 3H) 4.26 (t-like, 1H, J=6.1 Hz) 5.37–5.65 (m, 2H) 7.1–7.3 (m, 5H)

EXAMPLE 38

Synthesis of methyl (13E,15S)-15-(tert-butyldimethylsiloxy)-9-methyl-16-phenyl-17,18,19,20-tetranol-7-thiaprosta-8,13-dienoate

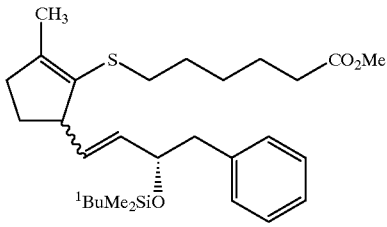

To tetrakistriphenylphosphine palladium prepared in advance in the reaction system from tris(dibenzylideneacetone)(chloroform)dipalladium(0) (65 mg, 0.063 mmol) and triphenylphosphine (131 mg, 0.51 mmol) were added methyl (13E,15S)-15-(tert-butyldimethylsiloxy)-9-trifluoromethanesulfonyloxy-16-phenyl-17,18,19,20-tetranol-7-thiaprosta-8,13-dienoate (239 mg, 0.38 mmol) in 1,2-dichloroethane (6.0 mL) and 1.02M trimethyl aluminum in hexane (0.550 mL, 0.57 mmol). This was agitated at 50° C. for 1 hour. Ether was added to dilute the reaction solution, then the solution was poured into 0.5N hydrochloric acid. The desired product was extracted with ether, was washed with brine, then was dried over anhydrous sodium sulfate. The solution was concentrated under reduced pressure, then was purified by silica gel column chromatography (5% ethyl acetate/hexane) to obtain methyl (13E,15S0-15-(tert-butyldimethylsiloxy)-9-methyl-16-phenyl-17,18,19,20-tetranol-7-thiaprosta-8,13-dienoate (12-position stereomixture: 144 mg, 76%).

$^1$H-NMR (270 MHz, δppm, CDCl$_3$): −0.22 (s, 5/4H) −0.20 (s, 7/4H) −0.13 (s, 5/4H) −0.19 (s, 7/4H) 0.80 (s, 15/4H) 0.81 (s, 21/4H) 1.2–1.7 (m, 8H) 1.78 (s, 3H) 2.30 (t, 2H, J=7.4 Hz) 2.00–2.65 (m, 4H) 2.74 (d-like, 2H, J=7.5 Hz) 3.28 (br, 1H) 3.66 (s, 3H) 4.27–4.3 (m, 1H) 5.37–5.53 (m, 2H) 7.1–7.35 (m, 5H)

EXAMPLE 39

Synthesis of methyl (13E,15S)-15-hydroxy-9-methyl-16-phenyl-17,18,19,20-tetranol-7-thiaprosta-8,13-dienoate

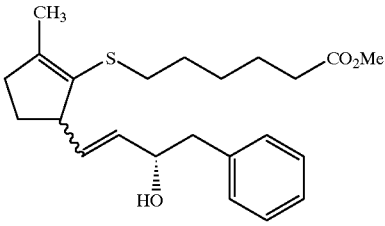

To a solution of ice-cooled acetonitrile (1 mL) and pyridine (0.25 mL) was added hydrogen fluoride-pyridine (0.25 mL). To this solution was added methyl (13E,15S)-15-(tert-butyldimethylsiloxy)-9-methyl-16-phenyl-17,18,19,20-tetranol-7-thiaprosta-8,13-dienoate (140 mg) in pyridine (0.25 mL). The ice bath was removed and the solution was agitated for 20 hours while returning it to room temperature. The reaction solution was poured into a mixture of ethyl acetate and saturated aqueous sodium hydrogencarbonate. The desired product was extracted from this mixed solution with ethyl acetate, was washed with brine, then was dried over anhydrous sodium sulfate. This was concentrated under reduced pressure and subjected to HPLC (reversed phase partition column InertsilPREP-ODS; 70% water/acetonitrile) to obtain 12-position stereoisomers of methyl (13E,15S-15-hydroxy-9-methyl-16-phenyl-17,18,19,20-tetranol-7thiaprosta-8,13-dienoate separately (less polar compounds: 36 mg; more polar compounds: 28 mg).

$^1$H-NMR (270 MHz, δppm, CDCl$_3$): less polar (HPLC) compounds 1.35–1.75 (m, 8H) 1.80 (s, 3H) 2.0–2.15 (m, 2H) 2.30 (t, 2H, J=7.6 Hz) 2.2–2.65 (m, 3H) 2.84 (ddd, 2H, J=6.6 Hz) 3.3 (br, 1H) 3.66 (s, 3H) 4.28–4.38 (m, 1H) 5.5–5.65 (m, 2H) 7.18–7.35 (m, 5H) more polar (HPLC) compounds 1.3–1.75 (m, 8H) 1.79 (s, 3H) 1.97–2.14 (m, 2H) 2.30 (t, 2H, J=7.5 Hz) 2.17–2.65 (m, 3H) 2.83 (d, 2H, J=24 Hz, 13.5 Hz, 6 Hz) 3.3 (br, 1H) 3.66 (s, 3H) 4.3–4.4 (m, 1H) 5.5–5.7 (m, 2H) 7.2–7.35 (m, 5H)

EXAMPLE 40

Synthesis of methyl (11R,12S)-9-trifluoromethanesulfonyloxy-11,15-bis(tert-butyldimethylsiloxy)-16-phenyl-17,18,19,20-tetranol-7-thiaprosta-8-enoate

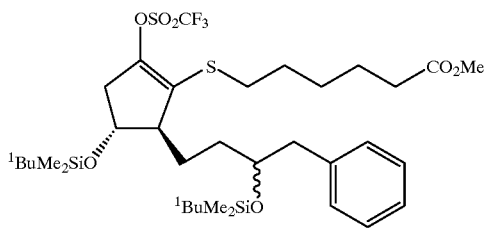

1-iodo-3-(tert-butyldimethylsiloxy)-4-phenyl-butane (702 mg) in ether (4.0 mL) was cooled to −78° C., then tert-butyllithium (1.50 mol/L, 2.40 mL) was added. This was agitated at −78° C. for 1.5 hours. Further, to this were added 1-hexynylcopper (I) (260 mg) and hexamethylposphorus triamide (654μl) in ether (10 mL). This was agitated at −78° C. for a further 1 hour to give copper reagent. To the copper reagent thus obtained was drop-wise added (4R)-tert-butyldimethyl-siloxy-2-(5-methoxycarbonylpentylthio)-2-cyclopenten-1-one (559 mg) in tetrahydrofuran (15 mL). This reaction mixture was agitated at −78° C. for 30 minutes, then the reaction temperature was raised and the solution was agitated at −50 to −30° C. for 30 minutes. To the obtained conjugate adduct was added at −50° C. N-phenyltrifluoromethanesulfonimide (1.45 g) in tetrahydrofuran (15 ml). The solution was agitated for 1 hour while raising the reaction temperature to room temperature. The reaction solution was poured into saturated aqueous ammonium sulfate (100 mL) to end the reaction. The mixture was separated, then the aqueous solution was extracted with ether. The extract was combined with the organic layer, then dried over anhydrous magnesium sulfate. This was concentrated under reduced pressure, then was purified by silica gel column chromatography (3% ethyl acetate/hexane) to obtain methyl (11R,12)-9-trifluoromethanesulfonyloxy-11,15-bis(tert-butyldimethylsiloxy)-16-phenyl-17,18,19,20-tetranol-7-thiaprosta-8-enoate (15-position stereomixture: 888 mg, 77%).

$^1$H-NMR (270 MHz, δppm, CDCl$_3$): −0.06–0.01 (m, 12H) 0.83 (s, 9H) 0.85 (s, 9H) 1.2–1.7 (m, 10H) 2.28 (t, 2H, J=7.6 Hz) 2.35–2.95 (m, 7H) 3.64 (s, 3H) 3.8 (m, 1H) 4.02 (br-t, 1H, J=6.3 Hz) 7.1–7.3 (m, 5H)

EXAMPLE 41

Synthesis of methyl (11R,12S)-11,15-bis(tert-butyldimethylsiloxy)-9-methyl-16-phenyl-17,18,19,20-tetranol-7-thiaprosta-8-enoate

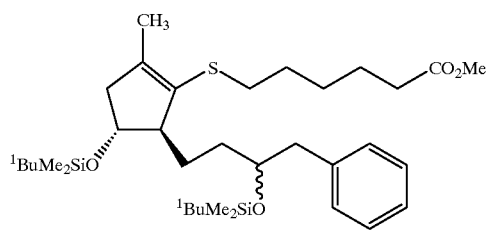

To tetrakistriphenylphosphine palladium prepared in advance in the reaction system from tris(dibenzylideneacetone)(chloroform)dipalladium(0) (95 mg, 0.091 mmol) and triphenylphosphine (191 mg, 0.72 mmol) were added methyl (11R,12S)-9-trifluoromethanesulfonyloxy-11,15-bis(tert-butyldimethylsiloxy)-16-phenyl-17,18,19,20-tetranol-7-thiaprosta-8-enoate (423 mg, 0.55 mmol) in 1,2-dichloroethane (10 mL) and 1.02M trimethylaluminum in hexane (0.830 mL, 0.83 mmol). This was agitated at 60° C. for 1 hour. Ether was added to dilute the reaction solution, then the solution was poured into 0.5N hydrochloric acid. The desired product was extracted with ether, was washed with brine, then was dried over anhydrous sodium sulfate. The solution was concentrated under reduced pressure, then was purified by silica gel column chromatography (3% ethyl acetate/hexane) to obtain methyl (11R,12S)-11,15-bis(tert-butyldimethylsiloxy)-9-methyl-16-phenyl-17,18,19,20-tetranol-7-thiaprosta-8-enoate (15-position stereomixture: 216 mg, 62%).

$^1$H NMR (270 MHz, δppm, CDCl$_3$): −0.08 (s, 3H) −0.57 (s, 3H) −0.01 (s, 3H) 0.01 (s, 3H) 0.83 (s, 9H) 0.84 (s, 9H) 1.2–1.7 (m, 10H) 1.76 (s, 3H) 2.1–2.75 (m, 7H) 2.28 (t, 2H, J=7.6 Hz) 3.65 (s, 3H) 3.75–3.85 (m, 1H) 3.95–4.05 (m, 1H) 7.1–7.3 (m, 5H)

EXAMPLE 42

Synthesis of methyl (11R,12S)-11, 15-dihydroxy-9-methyl-16-phenyl-17,18,19,20-tetranol-7-thiaprosta-8-enoate

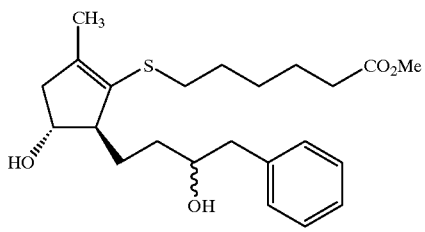

To a solution of ice-cooled acetonitrile (1.5 mL) and pyridine (0.4 mL)was added hydrogen fluoride-pyridine (0.4 mL). To this solution was added methyl (11R,12S)-11,15-bis(tert-butyldimethylsiloxy)-9-methyl-16-phenyl-17,18,19,20-tetranol-7-thiaprosta-8-enoate (214 mg) in pyridine (0.4 mL). The ice bath was removed and the solution was agitated for 20 hours while returning it to room temperature. The reaction solution was poured into a mixture of ethyl acetate and saturated aqueous sodium hydrogencarbonate. The desired product was extracted from this mixed solution with ethyl acetate, was washed with brine, then was dried over anhydrous sodium sulfate. This was concentrated under reduced pressure , then was purified by silica gel column chromatography (55% ethyl acetate/hexane) to obtain methyl (11R,12S)-11,15-dihydroxy-9-methyl-16-phenyl-17,18,19,20-tetranol-7-thiaprosta-8-enoate (15-position stereomixture: 117 mg, 85%).

$^1$H-NMR (270 MHz, δppm, CDCl$_3$): 1.2–2.15 (m, 12H) 2.30 (t, 2H, J=7.3 Hz) 2.2–2.9 (m, 7H) 3.65 (s, 1H) 3.75–3.95 (m, 1H) 4.1–4.2 (br, 1H) 7.15–7.35 (m, 5H)

EXAMPLE 43

Synthesis of (3S,4R)-4-(tert-butyldimethylsiloxy)-2-hexylthio-3-[(1E)-4-phenyl-3-(tert-butyldimethylsiloxy)-1-butenyl]-1-cyclopentenyltrifluoromethanesulfonate

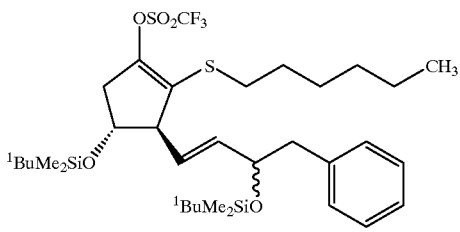

(1E)-1-iodo-3-(tert-butyldimethylsiloxy)-4-phenyl-1-butene (406 mg) in ether (3.0 mL) was cooled to −78° C., then tert-butyllithium (1.50 mol/L, 1.60 ml) was added. This was agitated at −78° C. for 1 hour. Further, to this were added 1-hexynylcopper (I) (174 mg) and hexamethylphosphorus triamide (436 µl) in ether (10 mL). This was further agitated for 1 hour at −78° C. to give a copper reagent. To the copper reagent thus obtained was added drop-wise (4R)-tert-butyldimethylsiloxy-2-(5-hexylthio)-2-cyclopenten-1-one (329 mg) in tetrahydrofuran (10 mL). This reaction mixture was agitated at −78° C. for 30 minutes, then the reaction temperature was raised and the solution was agitated at −50 to −30° C. for 2 hours. To the conjugate adduct thus obtained was added at −50° C. N-phenyltrifluoromethanesulfonimide (925 mg) in tetrahydrofuran (10 mL). This was then agitated for 18 hours, while raising the reaction temperature to room temperature. The reaction solution was poured into saturated aqueous ammonium sulfate (70 mL) to end the reaction. The mixture was separated, then the aqueous solution was extracted with ether. The extract was combined with the organic layer, then dried over anhydrous magnesium sulfate. This was concentrated under reduced pressure, then was purified by silica gel column chromatography (2% ethyl acetate/hexane) to obtain (3S,4R)-4-(tert-butyldimethylsiloxy)-2-hexylthio-3-[(1E)-4-phenyl-3-(tert-butyldimethylsiloxy)-1-butenyl]-1-cyclopentenyltrifluoromethanesulfonate (476 mg, 66%).

$^1$H-NMR (270 MHz, δppm, CDCl$_3$): −0.21 (s, 3/2H) −0.20 (s, 3/2H) −0.09 (s, 3/2H) −0.8 (s, 3/2H) 0.05 (s, 6H) 0.84 (s, 9/2H) 0.85 (s, 9/2H) 0.88 (s, 9H) 0.86 (t, 3H, J=8 Hz) 1.2–1.6 (m, 8H) 2.75 (d, 2H, J=6.6 Hz) 2.4–3.0 (m, 4H) 3.16 (d-like, 2H, J=7.9 Hz) 4.0 (br, 1H) 4.25–4.35 (m, 1H) 5.35–5.50 (m, 1H) 5.63–5.73 (m, 1H) 7.15–7.35 (m, 5H)

EXAMPLE 44

Synthesis of (3S,4R)-4-(tert-butyldimethylsiloxy)-2-hexylthio-3-[(1E)-4-phenyl-3-(tert-butyldimethylsiloxy)-1-butenyl]-1-methyl-1-cyclopentene

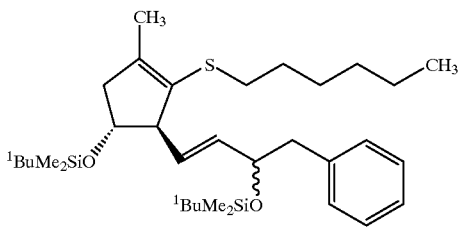

To tetrakistriphenylphosphine palladium prepared in advance in the reaction system from tris(dibenzylideneacetone)(chloroform)dipalladium(0) (68 mg, 0.065 mmol) and triphenylphosphine (138 mg, 0.52 mmol) were added (3S,4R)-4-(tert-butyldimethylsiloxy)-2-hexylthio-3-[(1E)-4-phenyl-3-(tert-butyldimethylsiloxy)-1-butenyl]-1-cyclopentenyltrifluoromethanesulfonate (470 mg, 0.65 mmol) in 1,2-dichloroethane (6 mL) and 1.02M trimethylaluminum in hexane (0.956 mL, 0.98 mmol). This was agitated at 50° C. for 1.5 hours. Ether was added to dilute the reaction solution, then the solution was poured into 0.5N hydrochloric acid. The desired product was extracted with ether, was washed with brine, then was dried over anhydrous sodium sulfate. The solution was concentrated under reduced pressure, then was purified by silica gel column chromatography (1% ethyl acetate/hexane) to obtain (3S,4R)-4-tert-butyldimethylsiloxy)-2-hexylthio-3-[(1E)-4-phenyl-3-(tert-butyldimethylsiloxy)-1-butenyl]-1-methyl-1-cyclopentene (314 mg, 83%).

$^1$H -NMR (270 MHz, δppm, CDCl$_3$): −0.24 (s, 3H) −0.23 (s, 3H) −0.11 (s, 3H) −0.10 (s, 3H) 0.81 (s, 9/2H) 0.83 (s, 9/2H) 0.87 (s, 9H) 0.86 (t, 3H, J=8 Hz) 1.2–1.7 (m, 8H) 1.79 (s, 3H) 2.20 (d, 1H, J=16.5 Hz) 2.32–2.46 (m, 1H) 2.51–2.69 (m, 2H) 2.75 (d, 2H, J=6.6 Hz) 3.13 (d, 1H, J=7.9 Hz) 3.95–4.05 (m, 1H) 4.19–4.29 (m, 1H) 4.34–4.45 (m, 1H) 5.54 (dd, 1H, J=15.6 Hz, 6.1 Hz) 7.1–7.3 (m, 5H)

EXAMPLE 45

Synthesis of (3S,4R)-2-hexylthio-4-hydroxy-3-[(1E)-4-phenyl-3-hydroxy-1-butenyl]-1-methyl-1-cyclopentene

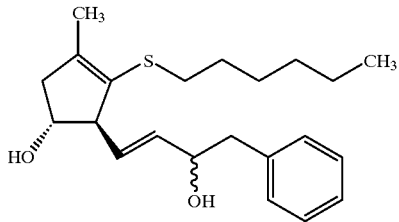

To a solution of ice-cooled acetonitrile (2 ml) and pyridine (0.5 mL) was added hydrogen fluoride-pyridine (0.5 mL). To this solution was added (3S,4R)-4-(tert-butyldimethylsiloxy)-2-hexylthio-3-[(1E)-4-phenyl-3-(tert-butyldimethylsiloxy)-1-butenyl]-1-methyl-1-cyclopentene (295 mg) in pyridine (1.5 mL). The ice bath was removed and the solution was agitated for 20 hours while returning it to room temperature. The reaction solution was poured into a mixture of ethyl acetate and saturated aqueous sodium hydrogencarbonate. The desired product was extracted from this mixed solution with ethyl acetate and was washed with brine, then was dried over anhydrous sodium sulfate. This was concentrated under reduced pressure, then was purified by silica gel column chromatography (30% ethyl acetate/hexane) to obtain stereoisomers of (3S,4R)-2-hexylthio-4-hydroxy-3-[(1E)-4-phenyl-3-hydroxy-1-butenyl]-1-methyl-1-cyclopentene separately (less polar compounds: 48.6 mg, 27%; more polar compounds: 53.5 mg, 30%).

$^1$H-NMR (270 MHz, δppm, CDCl$_3$): less polar compounds 0.88 (t, 3H, J=6.8 Hz) 1.15–1.55 (m, 8H) 1.69 (br, 1H) 1.81 (s, 3H) 2.03 (br, 1H) 2.2–2.90 (m, 6H) 3.14–3.24 (m, 1H) 4.06 (br, 1H) 4.34 (q-like, 1H, J=6.4 Hz) 5.53 (dd, 1H, J=15.6 Hz, 8.3 Hz) 5.64 (dd, 1H, J=15.6 Hz, 6.3 Hz) 7.15–7.35 (m, 5H) more polar compounds 0.88 (t, 3H, J=6.8 Hz) 1.15–1.55 (m, 8H) 1.67 (br, 1H) 1.81 (s, 3H) 1.85 (br, 1H) 2.25 (dd, 1H, J=16.8 Hz, 3.0 Hz) 2.38–2.52 (m, 1H) 2.53–2.74 (m, 2H) 2.85 (dd-like, 2H, J=6.8 Hz, 3.6 Hz) 3.18 (br-d, 1H, J=7.9 Hz) 3.92–4.02 (m, 1H) 4.35 (q-like, 1H, J=6.6 Hz) 5.45 (dd, 1H, J=15.5 Hz, 8.6 Hz) 5.65 (dd, 1H, J=15.5 Hz, 6.2 Hz) 7.15–7.35 (m, 5H)

EXAMPLE 46

Synthesis of methyl (11R,12S,13E)-11,15-bis(tert-butyldimethylsiloxy)-16-phenyl-17,18,19,20-tetranol-7-sulfinylprosta-8,13-dienoate

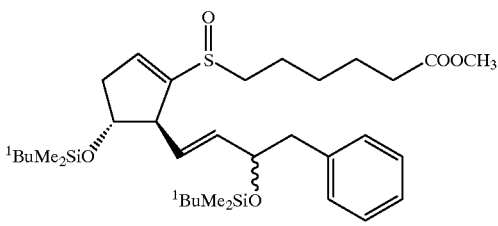

To a 30 mL flask was added methyl (11R,12S,13E)-11,15-bis(tert-butyldimethylsiloxy)-16-phenyl-17,18,19,20-tetranol-7-thiaprosta-8,13-dienoate (101 mg, 0.16 mmol) in dichloromethane (3 mL). This was ice-cooled, then m-chloroperbenzoic acid (36 mg, 0.21 mmol) was added. This was agitated for 5 hours under ice-cooling, then saturated aqueous sodium hydrogencarbonate (20 mL) was added and the resultant mixture was extracted with ethyl acetate (30 mL). The extract was dried over anhydrous magnesium sulfate, filtered, concentrated, then was purified by silica gel column chromatography (hexane/ethyl acetate 7:3) to obtain methyl (11R,12S,13E)-11,15-bis(tert-butyldimethylsiloxy)-16-phenyl-17,18,19,20-tetranol-7-sulfinylprosta-8,13-dienoate (78 mg, 77%) as a colorless oily substance.

$^1$H-NMR (270 MHz, δppm, CDCl$_3$): −0.25 (s, 3/4H) −0.24 (s, 3/4H) −0.23 (s, 3/4H) −0.22 (s, 3/4H) −0.13 (s, 3/4H) −0.10 (s, 3/2H) −0.09 (s, 3/4H) 0.04 (s, 3H) 0.05 (s, 3H) 0.82 (s, 9/4H) 0.83 (s, 9/2H) 0.84 (s, 9/4H) 0.87 (s, 9/4H) 0.87 (s, 9/2H) 0.88 (s, 9/4H) 1.25–1.85 (m, 6H) 2.32 (t, J=7.3 Hz, 2H) 2.33–2.85 (m, 7H) 3.02–3.11 (m, 1/2H) 3.35–3.44 (m, 1/2H) 3.65 (s, 3/2H) 3.66 (s, 3/2H) 4.12–4.35 (m, 2H) 5.34–5.52 (m, 1H) 5.55–5.73 (m, 1H) 6.38 (br.s, 1H) 7.10–7.30 (m, 5H)

EXAMPLE 47

Synthesis of methyl (11R,12S,13E)-11,15-dihydroxy-16-phenyl-17,18,19,20-tetranol-7-sulfinylprosta-8,13-dienoate

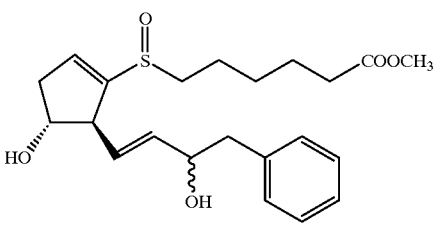

To a solution of ice-cooled acetonitrile (1 mL) and pyridine (0.25 mL) was added hydrogen fluoride-pyridine (0.25 mL). To this solution was added methyl (11R,12S,13E)-11,15-bis(tert-butyldimethylsiloxy)-16-phenyl-17,18,19,20-tetranol-7-sulfinylprosta-8,13-dienoate (20.1 mg, 0.033 mmol) in pyridine (0.25 mL). The ice bath was removed and the solution was agitated for 15 hours, while returning it to room temperature. The reaction solution was poured into a mixture of ethyl acetate and saturated aqueous sodium hydrogencarbonate. The desired product was extracted from this mixed solution with ethyl acetate, was washed with brine, then was dried over anhydrous sodium sulfate. This was concentrated under reduced pressure and subjected to HPLC (normal bonded phase column ZORBAX-SIL; hexane/ethanol/acetic acid, 80:20:0.1) to obtain methyl (11R,12S,13E)-11,15-dihydroxy-16-phenyl-17,18,19,20-tetranol-7-sulfinylprosta-8,13-dienoate (8.0 mg, 60%).

$^1$H-NMR (270 MHz, δppm, CDCl$_3$): 1.35–1.85 (m, 6H) 2.25–2.85 (m, 8H) 3.17–3.25 (s, 1/2H) 3.36–3.50 (s, 1/2H) 3.64 (s, 3/2H) 3.66 (s, 3/2H) 4.05–4.40 (m, 2H) 5.38–5.62 (m, 1H) 5.64–5.79 (m, 1H) 6.42 (br.s, 1H) 7.15–7.37 (m, 5H)

EXAMPLE 48

Synthesis of methyl (11R,12R,13E)-11,15-bis(tert-butyldimethylsiloxy)-9-trifluoromethanesulfonyloxy-16-phenyl-17,18,19,20-tetranolprosta-8,13-dienoate

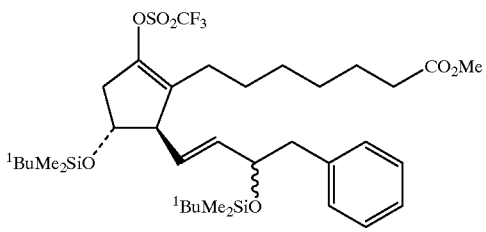

(1E)-1-iodo-3-(tert-butyldimethylsiloxy)-4-phenyl-1-butene (388 mg) in ether (3.0 mL) was cooled to −78° C., then tert-butyllithium (2.1 mol/L, 1.2 mL) was added. The solution was agitated at −78° C. for 1.5 hours. Further, to this were added 1-hexynylcopper (I) (144 mg) and hexamethylphosphorus triamide (327 μL) in ether (5.0 mL). The solution was agitated at −78° C. for a further 1.5 hours to give copper reagent. To the copper reagent thus obtained was drop-wise added (4R)-tert-butyldimethylsiloxy-2-(5-methoxycarbonylhexyl)-2-cyclopenten-1-one (256 mg) in tetrahydrofuran (5.0 ml). This reaction mixture was agitated at −78° C. for 1 hour, then the reaction temperature was raised to −40° C. The progress of the reaction was confirmed, then to the conjugate adduct thus obtained was added at −40° C. N-phenyltrifluoromethanesulfonimide in tetrahydrofuran (0.3M, 6.0 mL). This was agitated for 1 hour while gradually raising the reaction temperature to room temperature. The reaction solution was poured into saturated aqueous ammonium sulfate (10 mL) to end the reaction. The mixture was separated, then the aqueous solution was extracted with ether. The extract was combined with the organic layer, then dried over anhydrous magnesium sulfate. This was concentrated under reduced pressure, then was purified by silica gel column chromatography (1%–5% ethyl acetate/hexane) to obtain methyl (11R,12R,13E)-11,15-bis(tert-butyldimethylsiloxy)-9-trifluoromethanesulfonyloxy-16-phenyl-17,18,19,20-tetranolprosta-8,13-dienoate (15-position stereomixture: 308 mg, 57%).

$^1$H-NMR (270 MHz, δppm, CDCl$_3$): −0.24 (s, 3H) −0.12 (s, 3H) 0.04 (d, J=2.0 Hz, 6H) 0.81 (d, J=5.6 Hz, 9H) 0.87 (s, 9H) 1.15–1.41 (m, 8H) 1.56–1.66 (m, 1H) 2.32–2.48 (m, 2H) 2.29 (t, J=7.6 Hz, 2H) 2.75–2.92 (m, 1H) 2.29 (d, J=6.6 Hz, 2H) 2.94–3.04 (m, 1H) 3.66 (s, 3H) 3.94–4.05 (m, 1H) 4.19–4.29 (m, 1H) 5.23–5.35 (m, 1H) 5.44–5.56 (m, 5H) 7.13–7.30 (m, 5H)

EXAMPLE 49

Synthesis of methyl (11R,12R,13E)-11,15-bis(tert-butyldimethylsiloxy)-9-methyl-16-phenyl-17,18,19,20-tetranolprosta-8,13-dienoate

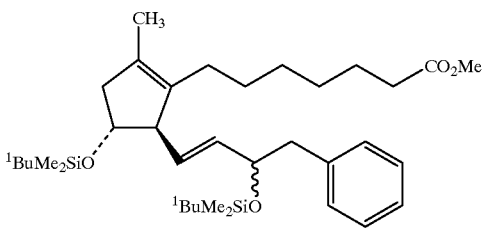

To tetrakistriphenylphosphine palladium prepared in advance in the reaction system from tris(dibenzylideneacetone)(chloroform)dipalladium(0) (85.4 mg, 0.082 mmol) and triphenylphosphine (172 mg, 0.65 mmol) were added methyl (11R,12R,13E)-11,15-bis(tert-butyldimethylsiloxy)-9-trifluoromethanesulfonyloxy-16-phenyl-17,18,19,20-tetranolprosta-8,13-dienoate (308 mg, 0.41 mmol) in 1,2-dichloroethane (8.0 mL) and 1.0M trimethylaluminum in hexane (0.7 mL, 0.7 mmol). This was agitated for 5 hours at 50° C. and for a further 15 hours at room temperature. Ether was added to dilute the reaction solution, then the solution was poured into 0.5N hydrochloric acid (30 mL). The desired product was extracted with ether, was washed with brine, then was dried over anhydrous sodium sulfate. The solution was concentrated under reduced pressure, then was purified by silica gel column chromatography (5% ethyl acetate/hexane) to obtain methyl (11R,12R,13E)-11,15-bis(tert-butyldimethylsiloxy)-9-methyl-16-phenyl-17,18,19,20-tetranolprosta-8,13-dienoate (15-position stereomixture: 75 mg, 30%).

$^1$H-NMR (270 MHz, δppm, CDCl$_3$): −0.24 (s, 3H) −0.12 (s, 3H) 0.04 (d, J=2.0 Hz, 6H) 0.81 (d, J=5.6 Hz, 9H) 0.87 (s, 9H) 1.15–1.41 (m, 8H) 1.56–1.66 (m, 1H) 1.62 (s, 3H) 2.12–2.24 (m, 1H) 2.29 (t, J=7.6 Hz, 2H) 2.42–2.58 (m, 1H) 2.29 (d, J=6.6 Hz, 2H) 2.94–3.04 (m, 1H) 3.66 (s, 3H) 3.94–4.05 (m, 1H) 4.19–4.29 (m, 1H) 5.23–5.35 (m, 1H) 5.44–5.56 (m, 1H) 7.13–7.30 (m, 5H)

EXAMPLE 50

Synthesis of methyl (11R,12R,13E)-11,15-dihydroxy-9-methyl-16-phenyl-17,18,19,20-tetranolprosta-8,13-dienoate

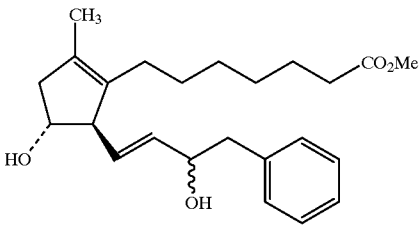

To a solution of ice-cooled acetonitrile (1 mL) and pyridine (0.2 mL) was added hydrogen fluoride-pyridine (0.25 mL). To this solution was added methyl (11R,12R,13E)-11,15-bis(tert-butyldimethylsiloxy)-9-methyl-16-phenyl-17,18,19,20-tetranolprosta-8,13-dienoate (74 mg) in pyridine (0.2 mL). The ice bath was removed and the solution was agitated for 15 hours, while returning it to room temperature. The reaction solution was poured into a mixture of ethyl acetate and saturated aqueous sodium hydrogencarbonate. The desired product was extracted from this mixed solution with ethyl acetate, was washed with brine, then was dried over anhydrous sodium sulfate. This was concentrated under reduced pressure, then was purified by silica gel column chromatography (50% ethyl acetate/hexane) to obtain 15-position stereoisomers of methyl (11R,12R,13E)-11,15-dihydroxy-9-methyl-16-phenyl-17,18,19,20-tetranolprosta-8,13-dienoate separately (less polar compounds: 15 mg; more polar compounds: 19 mg). Total yield 73%.

$^1$H-NMR (270 MHz, δppm, CDCl$_3$): less polar compounds 1.1–1.4 (m, 8H) 1.5–1.8 (m, 2H) 1.61 (s, 3H) 1.55–1.71 (m, 1H) 1.70–1.95, (m, 2H) 2.12–2.25 (m, 1H) 2.30 (t, J=7.2 Hz, 2H) 2.50–2.64 (m, 1H) 2.82 (d, J=6.3 Hz, 2H) 2.96–3.07 (m, 1H) 3.65 (s, 3H) 3.85–3.95 (m, 1H) 4.27–4.38 (m, 1H) 5.25–5.40 (m, 1H) 5.50–5.65 (m, 1H) 7.15–7.33 (m, 5H) more polar compounds 1.1–1.4 (m, 8H) 1.5–1.8 (m, 2H) 1.61 (s, 3H) 1.9–2.1 (m, 3H) 2.12–2.25 (m, 1H) 2.30 (t, J=7.2 Hz, 2H) 2.50–2.64 (m, 1H) 2.82 (d, J=6.3 Hz, 2H) 2.96–3.07 (m, 1H) 3.65 (s, 3H) 3.95–4.07 (m, 1H) 4.27–4.38 (m, 1H) 5.30–5.45 (m, 1H) 5.50–5.63 (m, 1H) 7.15–7.33 (m, 5H)

EXAMPLE 51

Synthesis of methyl (11R,12S,13E)-11,15-bis(tert-butyldimethylsiloxy)-9-trifluoromethanesulfonyloxy-16-phenyl-17,18,19,20-tetranol-3-oxa-7-thiaprosta-8,13-dienoate

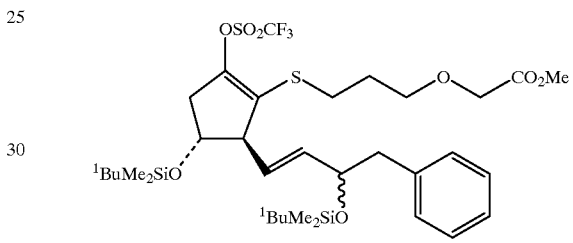

(1E)-1-iodo-3-(tert-butyldimethylsiloxy)-4-phenyl-1-butene (470 mg) in ether (3.0 mL) solution was cooled to −78° C., then tert-butyllithium (2.1 mol/L, 1.2 mL) was added. The solution was agitated at −78° C. for 1.5 hours. Further, to this were added 1-hexynylcopper (I) (175 mg) and hexamethylphosphorus triamide (390 µL) in an ether (6.0 mL). the resultant mixture was agitated at −78° C. for a further 1.5 hours to give a copper reagent. To the copper reagent thus obtained was added drop-wise (4R)-tert-butyldimethylsiloxy)-2-(3-(methoxycarbonylmethyloxy)propylthio)-2-cyclopenten-1-one (350 mg) in tetrahydrofuran (18 mL). This reaction mixture was agitated at −78° C. for 1 hour, then the reaction temperature was raised to −40° C. The progress of the reaction was confirmed, then to the resultant conjugate adduct was added at 40° C. N-phenyltrifluoromethane-sulfonimide in tetrahydrofuran (0.3M, 6.5 mL). This was agitated for 1 hour, while raising the reaction temperature to room temperature. The reaction solution was poured into saturated aqueous ammonium sulfate (10 mL) to end the reaction. The mixture was separated, then the aqueous layer was extracted with ether. The extract and the organic layer were combined and dried over anhydrous magnesium sulfate. This was concentrated under reduced pressure, then was purified by silica gel column chromatography (1%–5% ethyl acetate/hexane) to obtain methyl (11R,12S,13E)-11,15-bis(tert-butyldimethylsiloxy)9-trifluoromethanesulfonyloxy-16-phenyl-17,18,19,20-tetranol-3-oxa-7-thiaprosta-8,13-dienoate (15-position stereomixture: 268 mg, 37%).

$^1$H-NMR (270 MHz, δppm, CDCl$_3$):
−0.22 (s, 3H)
−0.09 (s, 3H)

0.05 (d, J=3.0 Hz, 6H)
0.79 (d, J=3.0 Hz, 9H)
0.82 (s, 9H)
1.7–1.9 (m, 1H)
2.38–2.45 (m, 1H)
2.55–2.92 (m, 2H)
2.70 (d, J=8.6 Hz, 2H)
3.09–3.16 (m, 1H)
3.52–3.60 (m, 2H)
3.70 (s, 3H)
3.93–3.98 (m, 1H)
4.02 (s, 2H)
4.22–4.30 (m, 1H)
5.38–5.44 (m, 1H)
5.57–5.68 (m, 1H)
7.08–7.22 (m, 5H)

EXAMPLE 52

Synthesis of methyl (11R,12S,13E)-11,15-bis(tert-butyldimethylsiloxy)-9-methyl-16-phenyl-17,18,19,20-tetranol-3-oxa-7-thiaprosta-8,13-dienoate

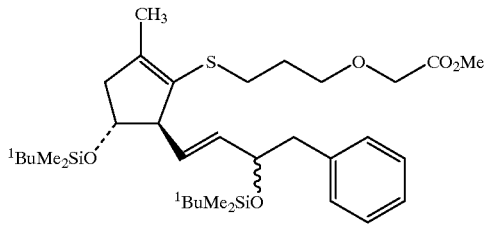

To tetrakistriphenylphosphine palladium prepared in advance in the reaction system from tris(dibenzylideneacetone) (chloroform) dipalladium(0) (108 mg, 0.104 mmol) and triphenrylphosphine (218 mg, 0.83 mmol) were added methyl (11R,12S,13E)-11,15-bis(tert-butyldimethylsoloxy)-9-trifluoromethanesulfonyloxy-16-phenyl-17,18,19,20-tetranol-3-oxa-7-thiaprosta-8,13-dieneoate (400 mg, 0.52 mmol) in 1,2-dichloroethane (8.0 mL) and 1.0M trimethylaluminum in hexane (0.85 mL, 0.7 mmol). This was agitated at 50° C. for 5 hours then at room temperature for 15 hours. Ether was added to dilute the reaction solution, then the solution was poured into 0.5N hydrochloric acid (30 mL). The desired product was extracted with ether, was washed with brine, then was dried over anhydrous sodium sulfate. The solution was concentrated under reduced pressure, then was purified by silica gel column chromatography (5% ethyl acetate/hexane) to obtain methyl (11R,12S,13E)-11,15-bis(tert-butyldimethylsiloxy)-9-methyl-16-phenyl-17,18,19,20-tetranol-3-oxa-7-thiaprosta-8,13-dienoate (15-position stereomixture: 120 mg, 36%).

$^1$H-NMR (270 MHz, δppm, CDCl$_3$):
–0.23 (s, 3H)
–0.10 (s, 3H)
0.03 (d, J=2.6 Hz, 6H)
0.78 (d, J=2.6 Hz, 9H)
0.82 (s, 9H)
1.65–1.86 (m, 1H)
1.76 (s, 3H)
2.13–2.32 (m, 1H)
2.42–2.68 (m, 2H)
2.71 (d, J=6.6 Hz, 2H)
3.07–3.12 (m, 1H)
3.47–3.60 (m, 2H)
3.71 (s, 3H)
3.92–4.01 (m, 1H)
4.03 (s, 2H)
4.13–4.22 (m, 1H)
5.25–5.48 (m, 1H)
5.53–5.48 (dd, J=15.5 Hz, 6.3 Hz, 1H)
7.05–7.22 (m, 5H)

EXAMPLE 53

Synthesis of methyl (11R,12S,13E)-11,15-dihyroxy-9-methyl-16-phenyl-17,18,19,20-tetranol-3-oxa-7-thiaprosta-8,13-dienoate

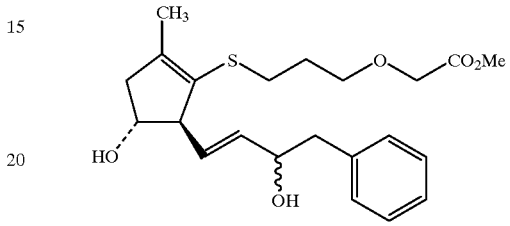

To a mixture of ice-cooled acetonitrile (1 mL) and pyridine (0.3 mL) was added hydrogen fluoride-pyridine (0.3 mL). to This solution was added methyl (11R,12S,13E)-11,15-bis(tert-butyldimethylsiloxy)-9-methyl-16-phenyl-17,18,19,20-tetranol-3-oxa-7-thiaprosta-8,13-dienoate (120 mg) in pyridine (0.3 mL). The ice bath was removed and the solution was agitated for 15 hours, while returning it to room temperature. The reaction solution was poured into a mixture of ethyl acetate and saturated aqueous sodium hydrogencarbonate. The desired product was extracted from this mixed solution with ethyl acetate, was washed with brine, then was dried over anhydrous sodium sulfate. This was concentrated under reduced pressure, then was purified by silica gel column chromatography (50% ethyl acetate/hexane) to obtain 15-position stereoisomers of methyl (11R,12S,13E)-11,15-dihydroxy-9-methyl-16-phenyl-17,18,19,20-tetranol-3-oxa-7-thiaprosta-8,13-diene acid separately (less polar compounds: 42 mg; more polar compounds: 28 mg). Total yield 89%.

$^1$H-NMR (270 MHz, δppm, CDCl$_3$):
less polar compounds
1.7–1.9 (s, 3H)
1.82 (s, 3H)
2.15–2.35 (m, 3H)
2.50–2.95 (m, 4H)
3.17–3.28 (m, 1H)
3.59 (t, J=6.9 Hz, 2H)
3.74 (s, 3H)
3.91–4.02 (m, 1H)
4.07 (s, 2H)
4.29–4.39 (m, 1H)
5.35–5.48 (m, 1H)
5.60–5.71 (m, 1H)
7.15–7.33 (m, 5H)
more polar compounds
1.7–1.9 (s, 2H)
1.82 (s, 3H)
2.15–2.35 (m, 3H)
2.50–2.95 (m, 4H)
3.17–3.28 (m, 1H)
3.59 (t, J=6.9 Hz, 2H)
3.74 (s, 3H)
4.0–4.1 (m, 1H)

4.07 (s, 2H)
4.29–4.39 (m, 1H)
5.30–5.45 (m, 1H)
5.60–5.71 (m, 1H)
7.15–7.33 (m, 5H)

EXAMPLE 54

Measurement of Inhibitory Activity of Cell Migration Caused by MCP-1

To evaluate the activity of the test compounds listed in the following table in inhibiting cell migration, the cell migration caused by the monocyte chemotactic protein MCP-1/MCAF was measured using human premonocyte-derived leukemia cells THP-1 (ATCCTIB203) as migrating cells and the method of FALK et al. (J. Immunol. Methods, vol. 33, pp. 239 to 247 (1980)) as follows. That is, to the upper chamber (200 μl) of a 96-well microchemotaxis chamber (made by Neuroprobe Co.) was added 2×10⁶/ml THP-1 cells (10% fetal calf serum (FCS) containing RPMI-1640 medium (made by Flow Laboratories Co.), while to the lower chamber (35 μl) was placed recombinant human MCP-1 (made by Peprotech Co.) diluted by the same solution to give a final concentration of 20 ng/ml. Between the two chambers, a polycarbonate filter (pore size 5 μm, PVP-free, made by Neuroprobe Co.) was affixed. Incubation was performed at 37° C. in the presence of 5% $CO_2$ for 2 hours. The filter was taken out and the cells migrating to the lower surface of the filter were immobilized and stained by a DiffQuick solution (made by Kokusai Shiyaku Co.) Next, a Breedmeter (made by Molecular Device Co.) was used for measurement at a measurement wavelength of 550 nm and the mean value of three wells was found and used as an indicator of the number of migrating cells. At this time, the test compound was added to the upper chamber together with THP-1 cells in various concentrations to find the cell migration inhibitory activity. The cell migration inhibition % was found by dividing the (number of migrating cells caused by MCP-1 added to the lower chamber in the case of addition of the test compound to the upper chamber)–(number of migrating cells in the case of no test compound added to the upper chamber and no MCP-1 added to the lower chamber) by (number of migrating cells caused by MCP-1 added to the lower chamber in the case of no test compound added to the upper chamber)–(number of migrating cells in the case of no test compound added to the upper chamber and no MCP-1 added to the lower chamber). The concentration of the compound exhibiting 50% inhibition was made the inhibition rate $IC_{50}$. The results are shown in the following tables.

TABLE 1

Cell Migration Inhibitory Activity

| Test compound | $IC_{50}(M)$ |
|---|---|
| (structure with $CO_2H$) | $7.2 \times 10^{-8}$ |
| (structure with $CO_2Me$) | $2.6 \times 10^{-8}$ |
| (structure with $CO_2Me$) | $4.5 \times 10^{-7}$ |

TABLE 1-continued

Cell Migration Inhibitory Activity

| Test compound | IC$_{50}$(M) |
|---|---|
| [structure with neopentyl group, S-linker to CO$_2$Me, cyclopentene, HO, HO, alkyl chain] | $6.0 \times 10^{-7}$ |
| [structure with CF$_3$ group, S-linker to CO$_2$Me, cyclopentene, HO, HO, alkyl chain] | $2.5 \times 10^{-6}$ |
| [structure with CHO group, S-linker to CO$_2$Me, cyclopentene, HO, HO, alkyl chain] | $1.9 \times 10^{-7}$ |

TABLE 2

Cell Migration Inhibitory Activity

| Test compound | IC$_{50}$(M) |
|---|---|
| [structure with CO$_2$Me on ring, S-linker to CO$_2$Me, HO, HO, alkyl chain] | $4.7 \times 10^{-7}$ |
| [structure with acetyl group, S-linker to CO$_2$Me, HO, HO, alkyl chain] | $2.1 \times 10^{-7}$ |
| [structure with cyclopentene, S-linker to CO$_2$Me, HO, HO, alkyl chain] | $1.3 \times 10^{-8}$ |

TABLE 2-continued

Cell Migration Inhibitory Activity

| Test compound | IC$_{50}$(M) |
|---|---|
| [structure with cyclopentene, S-linker to CO$_2$H, HO, HO, alkyl chain] | $1.5 \times 10^{-7}$ |
| [structure with cyclopentene, S-linker to CO$_2$Me, HO, HO, benzyl chain] | $3.8 \times 10^{-7}$ |

TABLE 3

Cell Migration Inhibitory Activity

| Test compound | | $IC_{50}(M)$ |
|---|---|---|
| [structure: cyclopentene with CH₃, S-(CH₂)₄-CO₂Me, OH, CH=CH-CH(OH)-CH₂-phenyl] | Less polar isomer | $2.1 \times 10^{-7}$ |
| [structure: cyclopentene with CH₃, S-(CH₂)₄-CO₂Me, OH, CH=CH-CH(OH)-CH₂-phenyl] | More polar isomer | $1.0 \times 10^{-8}$ |
| [structure: cyclopentene with CH₃, S-(CH₂)₄-CO₂H, OH, CH=CH-CH(OH)-CH₂-phenyl] | Compound of Ex. 34 | $1.6 \times 10^{-8}$ |
| [structure: cyclopentene with cyclopropyl, S-(CH₂)₄-CO₂Me, OH, CH=CH-CH(OH)-CH₂-phenyl] | Less polar isomer | $2.0 \times 10^{-7}$ |
| [structure: cyclopentene with CH₃, S-(CH₂)₄-CO₂Me, CH=CH-CH(OH)-CH₂-phenyl] | More polar isomer | $1.5 \times 10^{-8}$ |
| [structure: cyclopentene with CH₃, S-(CH₂)₄-CO₂Me, OH, CH₂-CH₂-CH(OH)-CH₂-phenyl] | | $1.2 \times 10^{-7}$ |

TABLE 4

Cell Migration Inhibitory Activity

| Test compound | | $IC_{50}(M)$ |
|---|---|---|
| [structure: cyclopentene with CH3, HO, linked to CO2Me chain and styryl-HO group] | More polar isomer | $6.5 \times 10^{-8}$ |
| [structure: cyclopentene with CH3, HO, S-propyl-O-CH2-CO2Me chain, styryl-HO group] | More polar isomer | $3.6 \times 10^{-7}$ |

EXAMPLE 55

Measurement of Inhibitory Activity of Cell Migration Caused by PDGF

To evaluate the activity of the test compounds listed in the following table to inhibit cell migration caused by PDGF, the migrating cells caused by human platelet derived growth factor (PDGF) were measured in the following way using the vascular smooth muscle cells derived from normal human arteries (made by Kurabo) and according to the method of MaCarthy et al. (J. Cell. Biol. 97, 772–777 (1983)). That is, a Transwell Chamber (Costar Co., registered trademark) was used to measure the inhibitory action. The chamber was divided into two layers, upper and lower, by a 8 µm pore size membrane filter (PVP-free polycarbonate filter, Nucleopore Co., registered trademark). The filter was precoated on its lower surface with 5 µg of rat tail collagen type 1 (Becton Dickinson Co.) To the upper chamber (100 µl) was added a 1.5×10⁶/ml suspension of cells (DMEM (made by Flow Laboratories Co.) containing 0.1% BSA (made by Nakalai Tesque Co.) In the lower chamber (600 µl) was placed the same solution diluted by human PDGF (made by Becton Dickinson) to give a final concentration of 10 ng/ml. At this time, the test compound was added in different concentrations to both the upper and lower chambers. The chambers were incubated at 37° C. under 5% $CO_2$ for 6 hours, then the filter was removed, fixed in 99.7% methanol, then stained with hematoxylin and eosin. The cells on the upper surface of the filter were removed by wiping with a cotton swab and the cells that had migrated to the lower surface of the filter were counted under a high output microscope (×200). Usually, five fields were counted per filter. The migrated cells were shown by the average cell count of five fields. The inhibition rate (%) was shown by the ratio of the count of the migrating cells in the case of treatment by the test compound to the count of migrating cells in the case of no treatment. The inhibition rate (%) of the test compounds at a concentration of 10–8M are shown in Table 5.

TABLE 5

Inhibitory Activity of Cell Migration Caused by PDGF

| Test compound | | $IC_{50}(M)$ |
|---|---|---|
| [structure: cyclopentene with CH3, HO, S-pentyl-CO2Me chain, styryl-HO group] | More polar isomer | $8.1 \times 10^{-8}$ |

TABLE 5-continued

Inhibitory Activity of Cell Migration Caused by PDGF

| Test compound | IC$_{50}$(M) |
|---|---|
| Compound of Ex. 34 | $7.3 \times 10^{-8}$ |

EXAMPLE 56

Thickening of Intima of Carotid Artery of Rat Due to Balloon Catheter

Test compound: Methyl (11R,12S,13E,15S,17R)-11,15-dihydroxy-17,20-dimethyl-7-thiaprosta-8,13-dienoato

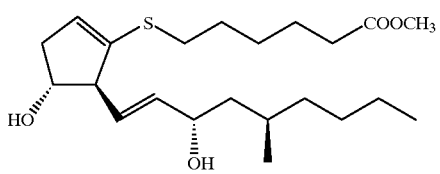

The test was performed in the following manner in accordance with the method of Crose et al. (Lab. Invest., vol. 49, p. 206, 1983). Male Wistar rats having a body weight of 300 to 350 g were used. The neck of each rat was opened under anesthesia by sodium pentobarbitol, then a balloon catheter (Fogarty, 2F) was inserted from the right external carotid artery, until the starting portion of the common carotid artery. The balloon was expanded by physiological saline to such an extent causing a light resistance, then the catheter was pulled out in that state up to the carotid artery to give trauma to the intima. This procedure was repeated three times, then the catheter was withdrawn and the external carotid artery was sewn up. After 14 days, the chest was opened under anesthesia by diethyl ether, refluxing was performed from the aorta by a Carnoa solution (methanol:chloroform:acetic acid=6:3:1), then the right common carotid artery was excised and immobilized by neutral formalin solution. The immobilized carotid artery was dyed by Elasticavan Gieson dye, then the areas of the Media and thickened portion of the Intima were measured by an image resolution device (LUZEX2D).

The test compound began to be administered subcutaneously at a rate of 3.2 μg/rat/hr using a miniosmotic pump buried in the back of the rat from 3 days before the surgery and was continued until 11 days after the surgery. The activity of the test compound in suppressing intima thickening was found from the following formula.

Intima thickening suppression rate (%)=(1-T/C)×100 wherein, T shows the ratio between the area of the thickened portion of the intima and the area of the media portion of the rats of the group administered the test compound, while C shows that of the control group (group administered solvent) [Intima/Media].

The test results are shown in Table 6.

TABLE 6

| | Activity Suppressing Thickening of Intima in Rats | | |
|---|---|---|---|
| Drug | No. of examples | Intima/media (Average ± standard error) | Suppression Rate (%) |
| Control | 12 | 0.935 ± 0.377 | |
| Test compound | 10 | 0.702 ± 0.241 | 25 |

As is clear from the test results, the test compounds suppressed the thickening of the intima of the veins.

EXAMPLE 57

Measurement of Inhibitory Activity of Platelet Aggregation in Rats

Wistar rats (male, approximately 400 g) were made to fast for 1 day, then the entire blood was taken from the abdominal artery under anesthesia by ether. To this was added a 3.8% aqueous solution of sodium citrate in a ⅒ amount followed by immediate mixture. This was centrifuged at 1000 rpm for 10 minutes. The top layer was used as the platelet rich plasma. The bottom layer was centrifuged at 3000 rpm for 10 minutes and the top layer was used as the platelet poor plasma. The platelet rich plasma was diluted by the platelet poor plasma to give a platelet count of $3.5 \times 10^8$/mm$^3$. This was used for the measurement. Note that the platelets were measured using an automatic blood cell counter MEK-4500 (Nihon Koden). The platelet aggregation was measured by measuring the turbidity using an NBS HEMATRACER 801 (M. C. Medical). 90 μl of the platelets were placed in cuvettes, then 5 μl of the different test compounds were added to give the target final concentration, then these were heated for 1 minute at 37° C., then 5 μl of an aqueous solution of 100 μM adenosine 2-phosphoric acid (M. C. Medical) was added to cause platelet aggregation. The activity inhibiting aggregation was found from the following formula:

Aggregation inhibiting rate (%)
={1-(maximum change in turbidity at time of addition of test compound)
÷(maximum change in turbidity at time of no addition of test compound)}
×100

The concentration of the compound exhibiting 50% inhibition was made the $IC_{50}$. The results are shown in Table 7.

TABLE 7

| Test compound | Activity Suppressing Platelet Aggregation (Rats) $IC_{50}(M)$ |
|---|---|
| (structure) | $4.5 \times 10^{-6}$ |
| (structure) | $7.6 \times 10^{-7}$ |
| (structure) | $2.2 \times 10^{-6}$ |

INDUSTRIAL APPLICABILITY

Drugs containing as their active ingredients the prostaglandins of the present invention and their enantiomers or mixtures of any ratio of the enantiomers or their pharmacologically allowable salts have an inhibitory activity on cell migration caused by chemokines, for example, MCP-1/MCAF and are useful as drugs for the prevention and treatment of diseases such as restenosis or reocclusion occurring after trauma to the intima of arteries in agioplasty etc., stenosis or occlusion caused primarily by formation of atherosclerosis at the coronary artery or carotid artery etc., and other diseases having as one of their characteristics the aggregation of monocytes in the blood at the leasion.

Further, the prostaglandins of the present invention have the characteristic biological action of prostaglandin derivatives of activity inhibiting platelet aggregation and are useful also as drugs for the prevention and treatment of diseases for which prostaglandin derivatives were conventionally considered useful such as thrombosis, cardiac infarction, and angina.

We claim:

1. A prostaglandin having the formula (I):

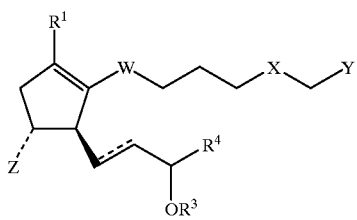

(I)

wherein $R^1$ indicates a $C_1$ to $C_{10}$ straight chain or branched alkyl group, a $C_3$ to $C_8$ cycloalkyl group, a cyano group, a formyl group, a carboxyl group, a $C_1$ to $C_5$ alkyloxy-carbonyl group, a $C_2$ to $C_7$ alkanoyl group, or a $C_1$ to $C_5$ alkyl group substituted with one or more halogen atoms or one or more substituted or unsubstituted phenyl groups, Z indicates a hydrogen atom or $OR^2$, $R^2$ and $R^3$ are the same or different and indicate a hydrogen atom, a tri $C_1$ to $C_7$ hydrocarbon silyl group, or a group forming an acetal bond with the oxygen atom of a hydroxy group, $R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group, Y indicates a $C_1$ to $C_5$ straight chain or branched alkyl group or $CO_2R^5$, $R^5$ indicates a hydrogen atom, a $C_1$ to $C_{10}$ straight chain or branched alkyl group, or a $C_2$ to $C_{10}$ straight chain or branched alkenyl group, or one equivalent cation, X indicates a methylene group or an oxygen atom, W indicates a sulfur atom, a sulfynyl group or a methylene group, and the bond represented by a solid line together with a broken line indicates a double bond or single bond, or an enantiomer thereof or any mixture of enantiomers at any ratio.

2. A prostaglandin as claimed in claim 1, wherein, in formula (I),

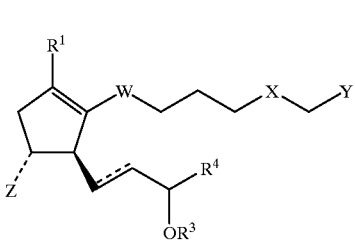

(I)

$R^1$ indicates a $C_1$ to $C_5$ straight chain or branched alkyl group, a cyclopropyl group, a cyano group, a formyl group, a methoxycarboxyl group, an acetyl group, a trifluoromethyl group or a phenethyl group, Z indicates a hydrogen atom or $OR^2$, $R^2$ and $R^3$ may be the same or different and indicate a hydrogen atom or a tert-butyldimethylsilyl group, $R^4$ indicates a $C_1$ to $C_8$ straight chain or branched alkyl group or a benzyl group, Y indicates a methyl group or $CO_2R^5$, $R^5$ indicates a hydrogen atom or a methyl group, X indicates a methylene group or an oxygen atom, W indicates a sulfur atom, a sulfinyl group or a methylene group, and the bond represented by a solid line together with a broken line indicates a double bond or single bond.

3. A prostaglandin having the formula (II):

$$\text{(II)}$$

wherein
- V indicates a sulfur atom or a sulfinyl group,
- Z indicates a hydrogen atom or $OR^2$,
- $R^2$ and $R^3$ are the same or different and indicate a hydrogen atom, a tri $C_1$ to $C_7$ hydrocarbon silyl group, or a group forming an acetal bond with the oxygen atom of a hydroxy group,
- $R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group,
- Y indicates a $C_1$ to $C_5$ straight chain or branched alkyl group or $CO_2R^5$,
- $R^5$ indicates a hydrogen atom, a $C_1$ to $C_{10}$ straight chain or branched alkyl group, or a $C_2$ to $C_{10}$ straight chain or branched alkenyl group, or one equivalent cation,
- X indicates a methylene group or an oxygen atom, and
- the bond represented by a solid line together with a broken line indicates a double bond or single bond, or
- an enantiomer thereof or any mixture of enantiomers at any ratio.

4. A prostaglandin as claimed in claim 3, wherein, in formula (II), $$\text{(II)}$$

wherein
- V indicates a sulfur atom or a sulfinyl group,
- Z indicates a hydrogen atom or $OR^2$,
- $R^2$ and $R^3$ may be the same or different and indicate a hydrogen atom or a tert-butyldimethylsilyl group,
- $R^4$ indicates a $C_1$ to $C_8$ straight chain or branched alkyl group or a benzyl group,
- Y indicates a methyl group or $CO_2R^5$,
- $R^5$ indicates a hydrogen atom or a methyl group,
- X indicates a methylene group or an oxygen atom, and
- the bond represented by a solid line together with a broken line indicates a double bond or single bond.

5. A prostaglandin having the formula (III):
wherein $$\text{(III)}$$

- $W^1$ indicates a sulfur atom or a methylene group,
- Z indicates a hydrogen atom or $OR^2$,
- $R^2$ and $R^3$ are the same or different and indicate a hydrogen atom, a tri $C_1$ to $C_7$ hydrocarbon silyl group, or a group forming an acetal bond with the oxygen atom of a hydroxy group,
- $R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group,
- Y indicates a $C_1$ to $C_5$ straight chain or branched alkyl group or $CO_2R^5$,
- $R^5$ indicates a hydrogen atom, a $C_1$ to $C_{10}$ straight chain or branched alkyl group, or a $C_2$ to $C_{10}$ straight chain or branched alkenyl group, or one equivalent cation,
- X indicates a methylene group or an oxygen atom, and
- the bond represented by a solid line together with a broken line indicates a double bond or single bond, or
- an enantiomer thereof or any mixtures of enantiomers at any ratio.

6. A process for producing a prostaglandin according to claim 5, comprising the steps of:
  (i) reacting
    (a) an organocopper compound prepared from an organolithium compound having the formula (IV):

$$\text{(IV)}$$

wherein
- $R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group, $R^{31}$ indicates a tri $C_1$ to $C_7$ hydrocarbon silyl group or a group forming an acetal bond with the oxygen atom of a hydroxy group, and the bond represented by a solid line together with a broken line indicates a double or a single bond and a copper reagent of the formula CuQ wherein Q indicates a 1-hexynyl group, a 1-pentynyl group, or a cyano group, with (b) a 2-cyclopentenone having the formula (V):

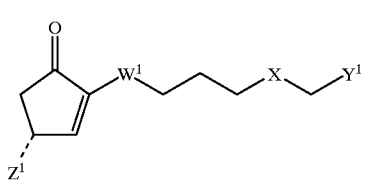

(V)

wherein $Z^1$ indicates a hydrogen atom or $OR^{21}$, $R^{21}$ indicates a tri $C_1$ to $C_7$ hydrocarbon silyl group or a group forming an acetal bond with the oxygen atom of a hydroxy group, $Y^1$ indicates a $C_1$ to $C_5$ straight chain or branched alkyl group or $CO_2R^{51}$, $R^{51}$ indicates a $C_1$ to $C_{10}$ straight chain or branched alkyl group or a $C_2$ to $C_{10}$ straight chain or branched alkenyl group, $W^1$ indicates a sulfur atom, a sulfynyl group or a methylene group, and X indicates a methylene group or an oxygen atom, or an enantiomer thereof or any mixture thereof at any ratio to obtain a reaction product; then (ii) reacting the reaction product of (i) with an sulfonimide having the formula (VI):

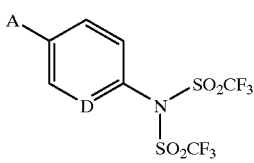

(VI)

wherein

A indicates a hydrogen atom or a chlorine atom and
D indicates a nitrogen atom or a methine group, to produce a compound having the formula (VII):

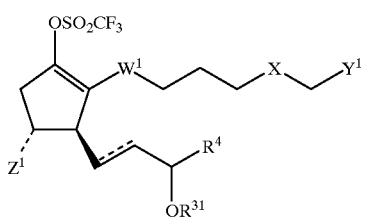

(VII)

wherein $R^{31}$, $R^4$, $W^1$, X, $Y^1$, $Z^1$ and the bond represented by a solid line together with a broken line have the same definitions set forth above, or an enantiomer thereof or any mixture of the enantiomers at any ratio and, (iii) further, optionally, removing the protective group and/or performing a hydrolysis reaction.

7. A process for producing a prostaglandin according to claim 1 or 2, comprising coupling a compound having the formula (VII)

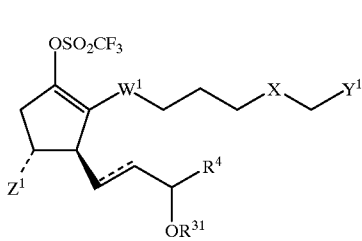

(VII)

wherein $R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group, $R^{31}$ indicates a tri $C_1$ to $C_7$ hydrocarbon silyl group or a group forming an acetal bond with the oxygen atom of a hydroxy group, $Z^1$ indicates a hydrogen atom or $OR^{21}$, $R^{21}$ indicates a tri $C_1$ to $C_7$ hydrocarbon silyl group or a group forming an acetal bond with the oxygen atom of a hydroxy group, $Y^1$ indicates a $C_1$ to $C_5$ straight chain or branched alkyl group or $CO_2R^{51}$, $R^{51}$ indicates a $C_1$ to $C_{10}$ straight chain or branched alkyl group or a $C_2$ to $C_{10}$ straight chain or branched alkenyl group, and $W^1$ indicates a sulfur atom, a sulfynyl group or a methylene group, and X indicates a methylene group or an oxygen atom, and the bond represented by a solid line together with a broken line indicates a double or a single bond, or an enantiomer or any mixture of enantiomers at any ratio and an organoboron compound having the formula (VIII):

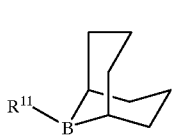

(VIII)

wherein $R^{11}$ indicates a $C_1$ to $C_{10}$ straight chain or branched alkyl group, or a $C_1$ to $C_5$ alkyl group substituted with one or more halogen atoms or one or more substituted or unsubstituted phenyl groups, an organolithium compound having the formula:

$(R^{12})_3Al$ wherein $R^{12}$ indicates a $C_1$ to $C_{10}$ straight chain or branched alkyl group or a $C_1$ to $C_5$ alkyl group substituted with a substituted or unsubstituted phenyl group an organozinc compound having the formula:

$R^{13}ZnI$ wherein $R^{13}$ indicates a $C_1$ to $C_{10}$ straight chain or branched alkyl group or a fluorine atom-substituted $C_1$ to $C_5$ alkyl group, an organotin compound having the formula:

$R^{14}SnBu_3$ wherein $R^{14}$ indicates a $C_1$ to $C_{10}$ straight chain or branched alkyl group or a $C_1$ to $C_5$ alkyl group substituted with a substituted or unsubstituted phenyl group and Bu represents a butyl group or a cyanide having the formula:

LCN wherein L indicates a sodium atom or a potassium atom in an inert gas atmosphere in the presence of a palladium catalyst to obtain a compound having the formula (I-1):

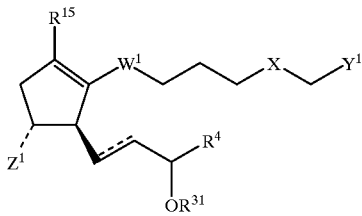

(I-1)

wherein $R^{15}$ indicates a $C_1$ to $C_{10}$ straight chain or branched alkyl group, a cyano group, or a $C_1$ to $C_5$ alkyl group substituted with one or more halogen atoms or substituted or unsubstituted phenyl groups, and $R^{31}$, $R^4$, $W^1$, X, $Y^1$, $Z^1$ and the bond represented by a solid line together with a broken line have the same definitions set forth above, or an enantiomer thereof or any mixture thereof at any ratio and, optionally, removing the protective group and/or performing a hydrolysis reaction.

8. A process for producing a prostaglandin according to claim 1 or 2 comprising:

carbonylating a compound having the formula (VII)

(VII)

wherein $R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group, $R^{31}$ indicates a tri $C_1$ to $C_7$ hydrocarbon silyl group or a group forming an acetal bond with the oxygen atom of a hydroxy group, $Z^1$ indicates a hydrogen atom or $OR^{21}$, $R^{21}$ indicates a tri $C_1$ to $C_7$ hydrocarbon silyl group or a group forming an acetal bond with the oxygen atom of a hydroxy group, $Y^1$ indicates a $C_1$ to $C_5$ straight chain or branched alkyl group or $CO_2R^{51}$, $R^{51}$ indicates a $C_1$ to $C_{10}$ straight chain or branched alkyl group or a $C_2$ to $C_{10}$ straight chain or branched alkenyl group, and $W^1$ indicates a sulfur atom, a sulfynyl group or a methylene group, and X indicates a methylene group or an oxygen atom, and the bond represented by a solid line together with a broken line indicates a double or a single bond, or an enantiomer or any mixture of enantiomers at any ratio in a carbon monoxide atmosphere in the presence of a palladium catalyst to obtain an intermediate, reacting the obtained intermediate with hydrogen gas, ammonium formate or formic acid and a tertiary amine salt to obtain a compound having the formula (I-2):

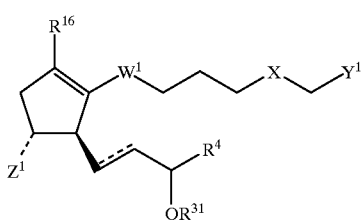

(I-2)

wherein $R^{16}$ is a formyl group and $R^{31}$, $R^4$, $W^1$, X, $Y^1$, $Z^1$ and the bond represented by a solid line together with a broken line have the same definitions set forth above, or an enantiomer thereof or any mixture of enantiomers at any ratio and, optionally, removing the protective group and/or applying a hydrolysis reaction.

9. A process for producing prostaglandin according to claim 1, comprising carbonylating a compound having the formula (VII)

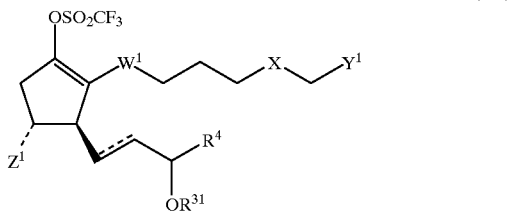
(VII)

wherein
- $R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group,
- $R^{31}$ indicates a tri $C_1$ to $C_7$ hydrocarbon silyl group or a group forming an acetal bond with the oxygen atom of a hydroxy group,
- $Z^1$ indicates a hydrogen atom or $OR^{21}$,
  - $R^{21}$ indicates a tri $C_1$ to $C_7$ hydrocarbon silyl group or a group forming an acetal bond with the oxygen atom of a hydroxy group,
- $Y^1$ indicates a $C_1$ to $C_5$ straight chain or branched alkyl group or $CO_2R^{51}$,
  - $R^{51}$ indicates a $C_1$ to $C_{10}$ straight chain or branched alkyl group or a $C_2$ to $C_{10}$ straight chain or branched alkenyl group, and
- $W^1$ indicates a sulfur atom, a sulfynyl group or a methylene group, and
- X indicates a methylene group or an oxygen atom, and
the bond represented by a solid line together with a broken line indicates a double or a single bond, or
an enantiomer thereof or any mixture of enantiomers at any ratio in the presence of a $C_1$ to $C_5$ alcohol or water in a carbon monoxide atmosphere and in the presence of a palladium catalyst
to obtain a compound having the formula (I-3):

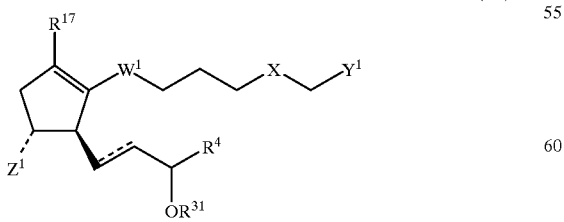
(I-3)

wherein
- $R^{17}$ indicates a carboxyl group or a $C_1$ to $C_5$ alkoxycarbonyl group and $R^{31}$, $R^4$, $W^1$, X, $Y^1$, $Z^1$ and the bond represented by a solid line together with a broken line have the same definitions set forth above, or
an enantiomer thereof or any mixture of enantiomers at any ratio and,
optionally, removing the protective group and/or applying a hydrolysis reaction.

10. A process for producing prostaglandin according to claim 1 or 2 comprising:
reacting a compound having the formula (VII)

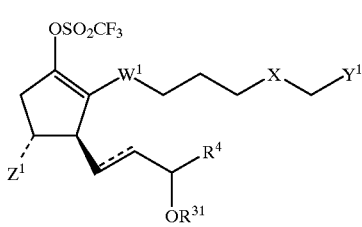
(VII)

- $R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group,
- $R^{31}$ indicates a tri $C_1$ to $C_7$ hydrocarbon silyl group or a group forming an acetal bond with the oxygen atom of a hydroxy group,
- $Z^1$ indicates a hydrogen atom or $OR^{21}$,
  - $R^{21}$ indicates a tri $C_1$ to $C_7$ hydrocarbon silyl group or a group forming an acetal bond with the oxygen atom of a hydroxy group,
- $Y^1$ indicates a $C_1$ to $C_5$ straight chain or branched alkyl group or $CO_2R^{51}$,
  - $R^{51}$ indicates a $C_1$ to $C_{10}$ straight chain or branched alkyl group or a $C_2$ to $C_{10}$ straight chain or branched alkenyl group, and
- $W^1$ indicates a sulfur atom, a sulfynyl group or a methylene group, and
- X indicates a methylene group or an oxygen atom, and
the bond represented by a solid line together with a broken line indicates a double or a single bond, or
an enantiomer thereof or any mixture of enantiomers at any ratio in a carbon monoxide atmosphere with
an organoboron compound having the formula (VIII')

(VIII')

wherein $R^{111}$ indicates a $C_1$ to $C_6$ straight chain or branched alkyl group,
an organolithium compound of $(R^{121})_3Al$ wherein $R^{121}$ indicates a $C_1$ to $C_6$ straight chain or branched alkyl group, or an organozinc compound having the formula:

$$R^{131}ZnI$$

wherein $R^{131}$ indicates a $C_1$ to $C_6$ straight chain or branched alkyl group, or an organotin compound having the formula:

$$R^{141}SnBu_3$$

wherein $R^{141}$ indicates a $C_1$ to $C_6$ straight chain or branched alkyl group and Bu represents a butyl group in the presence of a palladium catalyst to obtain an alkanoylated compound having the formula (I-4):

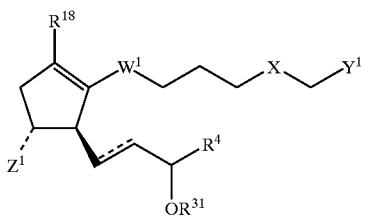

(I-4)

wherein $R^{18}$ indicates a carboxyl group or a $C_2$ to $C_7$ alkanoyl group, and $R^{31}$, $R^4$, $W^1$, $X$, $Y^1$, $Z^1$ and the bond represented by a solid line together with a broken line have the same definitions set forth above, or
an enantiomer thereof or any mixture of enantiomers at any ratio and, optionally, removing the protective group and/or applying a hydrolysis reaction.

11. A process for producing a prostaglandin according to claim 3 or 4 comprising:
reducing a compound having the formula (VII'):

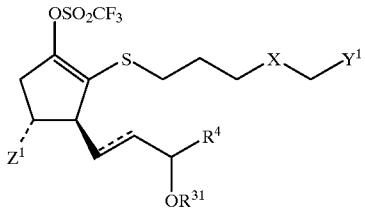

(VII')

$R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group,
$R^{31}$ indicates a tri $C_1$ to $C_7$ hydrocarbon silyl group or a group forming an acetal bond with the oxygen atom of a hydroxy group,
$Z^1$ indicates a hydrogen atom or $OR^{21}$,
$R^{21}$ indicates a tri $C_1$ to $C_7$ hydrocarbon silyl group or a group forming an acetal bond with the oxygen atom of a hydroxy group, $Y^1$ indicates a $C_1$ to $C_5$ straight chain or branched alkyl group or $CO_2R^{51}$,
$R^{51}$ indicates a $C_1$ to $C_{10}$ straight chain or branched alkyl group or a $C_2$ to $C_{10}$ straight chain or branched alkenyl group, and
X indicates a methylene group or an oxygen atom, and the bond represented by a solid line together with a broken line indicates a double or a single bond, or
an enantiomer thereof or any mixture of enantiomers at any ratio in the presence of a palladium catalyst using formic acid and further, optionally, removing the protective group and/or applying a hydrolysis reaction.

12. A process for producing a prostaglandin according to claim 1, wherein $R^1$ is a $C_3$ to $C_8$ cycloalkyl group or $C_1$ to $C_{10}$ straight chain or branched alkyl group, comprising the steps of:
(i) reacting (a) a compound having the formula (VII)

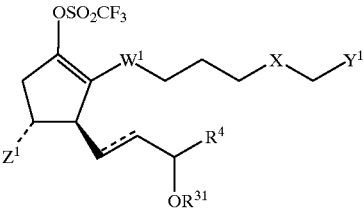

(VII)

wherein
$R^4$ indicates a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, or a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group,
$R^{31}$ indicates a tri $C_1$ to $C_7$ hydrocarbon silyl group or a group forming an acetal bond with the oxygen atom of a hydroxy group,
$Z^1$ indicates a hydrogen atom or $OR^{21}$,
$R^{21}$ indicates a tri $C_1$ to $C_7$ hydrocarbon silyl group or a group forming an acetal bond with the oxygen atom of a hydroxy group,
$Y^1$ indicates a $C_1$ to $C_5$ straight chain or branched alkyl group or $CO_2R^{51}$,
$R^{51}$ indicates a $C_1$ to $C_{10}$ straight chain or branched alkyl group or a $C_2$ to $C_{10}$ straight chain or branched alkenyl group, and
$W^1$ indicates a sulfur atom, a sulfynyl group or a methylene group, and
X indicates a methylene group or an oxygen atom, and the bond represented by a solid line together with a broken line indicates a double or a single bond, or
an enantiomer thereof or any mixture of enantiomers at any ratio with (b) an organocopper compound having the formula:

$$(R^{19})_2CuLi \text{ or } (R^{19})_2Cu(CN)Li_2$$

wherein $R^{19}$ indicates a $C_3$ to $C_8$ cycloalkyl group or $C_1$ to $C_{10}$ straight chain or branched alkyl group to obtain a compound having the formula (I-5):

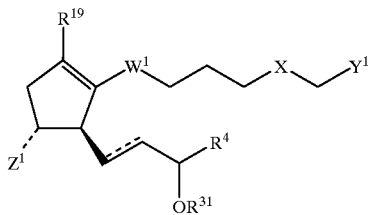
(I-5)

wherein $R^{19}$ indicates a $C_3$ to $C_8$ cycloalkyl group or $C_1$ to $C_{10}$ straight chain or branched alkyl group and $R^{31}$, $R^4$, $W^1$, X, $Y^1$, $Z^1$ and the bond represented by a solid line together with a broken line have the same definitions as set forth above, or an enantiomer thereof or any mixture of enantiomers at any ratio and, optionally, (ii) removing the protective group and/or applying a hydrolysis reaction.

13. A pharmaceutical composition for inhibiting cell migration caused by a chemokine comprising, as its active ingredient, an effective amount to inhibit cell migration of a prostaglandin having the formula (IX):

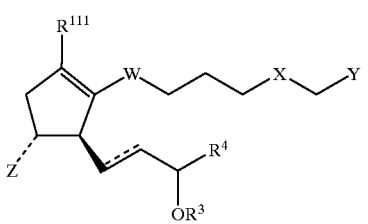
(IX)

wherein $R^{111}$ indicates a hydrogen atom, a $C_1$ to $C_{10}$ straight chain or branched alkyl group, a $C_3$ to $C_8$ cycloalkyl group, a cyano group, a formyl group, a carboxyl group, a $C_1$ to $C_5$ alkyl oxycarbonyl group, a $C_2$ to $C_7$ alkanoyl group, or a $C_1$ to $C_5$ alkyl group substituted with one or more halogen atoms or substituted or unsubstituted phenyl groups, Z indicates a hydrogen atom or $OR^2$, $R^2$ and $R^3$ are the same or different and indicate a hydrogen atom, a tri $C_1$ to $C_7$ hydrocarbon silyl group, or a group forming an acetal bond with the oxygen atom of a hydroxy group, $R^4$ is a $C_1$ to $C_8$ straight chain or branched alkyl group, a $C_2$ to $C_8$ straight chain or branched alkenyl group, a $C_2$ to $C_8$ straight chain or branched alkynyl group, a substituted or unsubstituted phenyl group, a substituted or unsubstituted $C_3$ to $C_8$ cycloalkyl group, and further a straight chain or branched ($C_1$ to $C_5$ alkyl group, $C_2$ to $C_5$ alkenyl group, or a $C_2$ to $C_5$ alkynyl group) each substituted with a $C_1$ to $C_5$ alkoxy group, a substituted or unsubstituted phenyl group, a substituted or unsubstituted phenoxy group, a substituted or unsubstituted $C_3$ to $C_8$ cycloalkyl group, or a substituted or unsubstituted heterocyclic group, Y indicates a $C_1$ to $C_5$ straight chain or branched alkyl group or $CO_2R^5$, $R^5$ indicates a hydrogen atom, a $C_1$ to $C_{10}$ straight chain or branched alkyl group, a $C_2$ to $C_{10}$ straight chain or branched alkenyl group, or one equivalent cation, X indicates a methylene group or an oxygen atom, W indicates a sulfur atom, a sulfynyl group or a methylene group, and the bond represented by a solid line together with a broken line indicates a double bond or single bond, or an enantiomer thereof or any mixture of enantiomers at any ratio.

* * * * *